US012447202B2

(12) United States Patent
Roberts et al.

(10) Patent No.: US 12,447,202 B2
(45) Date of Patent: Oct. 21, 2025

(54) ARTHROSPIRA PLATENSIS ORAL VACCINE DELIVERY PLATFORM

(71) Applicant: LUMEN BIOSCIENCE, INC., Seattle, WA (US)

(72) Inventors: James Roberts, Seattle, WA (US); Michael A. Tasch, Seattle, WA (US); Tracy Saveria, Seattle, WA (US)

(73) Assignee: Lumen Bioscience, Inc., Seattle, WA (US)

(*) Notice: Subject to any disclaimer, the term of this patent is extended or adjusted under 35 U.S.C. 154(b) by 919 days.

(21) Appl. No.: 17/056,306

(22) PCT Filed: May 17, 2019

(86) PCT No.: PCT/US2019/032998
§ 371 (c)(1),
(2) Date: Nov. 17, 2020

(87) PCT Pub. No.: WO2019/222711
PCT Pub. Date: Nov. 21, 2019

(65) Prior Publication Data
US 2021/0213124 A1 Jul. 15, 2021

Related U.S. Application Data

(60) Provisional application No. 62/672,891, filed on May 17, 2018.

(51) Int. Cl.
*A61K 39/015* (2006.01)
*A61K 39/00* (2006.01)
*A61P 37/04* (2006.01)

(52) U.S. Cl.
CPC ............ *A61K 39/015* (2013.01); *A61K 39/00* (2013.01); *A61P 37/04* (2018.01); *A61K 2039/51* (2013.01); *A61K 2039/542* (2013.01); *A61K 2039/545* (2013.01); *C12N 2730/10034* (2013.01); *C12N 2750/14334* (2013.01)

(58) Field of Classification Search
CPC .......... A61K 2039/523; A61K 2039/64; A61K 39/00; A61K 39/015; A61K 38/00; A61K 45/06; A61K 35/748; A61K 9/0053; A61K 2039/542; A61K 2039/51; C12N 2750/14334; C12N 2730/10034; C12N 1/12; C12N 1/20; C12N 1/205; C12N 15/74; C12N 15/79; C12N 9/1029; C12N 1/125; C12N 1/06; C12N 2770/20034; C12N 15/86; C12N 15/70; A23L 33/17; A23L 33/18; A23L 33/30; A23L 33/175; A23L 33/40; A23L 33/195; A23L 2/66; A23L 33/105; A23L 17/60; A23L 33/135; A23L 33/155; A23L 11/33; A23L 29/06; A23L 5/25; A23L 7/107; A23L 31/00; A23L 31/10; A23L 2/52; A23L 33/10; A23L 33/11; A23L 33/15; A23L 7/00; A23L 7/115; A23L 33/00; A23V 2002/00; A23V 2200/30; A23V 2250/202; A23V 2200/09; Y02A 50/30
See application file for complete search history.

(56) References Cited

U.S. PATENT DOCUMENTS

| | | | |
|---|---|---|---|
| 2,326,657 | A | 8/1943 | Johnston |
| 4,751,180 | A | 6/1988 | Cousens et al. |
| 4,873,192 | A | 10/1989 | Kunkel |
| 4,935,233 | A | 6/1990 | Bell et al. |
| 5,429,939 | A | 7/1995 | Misawa et al. |
| 5,589,581 | A | 12/1996 | Misawa et al. |
| 5,661,017 | A | 8/1997 | Dunahay et al. |
| 5,684,238 | A | 11/1997 | Ausich et al. |
| 5,811,273 | A | 9/1998 | Misawa et al. |
| 5,910,433 | A | 6/1999 | Kajiwara et al. |
| 5,972,690 | A | 10/1999 | Misawa et al. |
| 6,087,152 | A | 7/2000 | Hohmann et al. |
| 6,124,113 | A | 9/2000 | Hohmann et al. |
| 6,150,130 | A | 11/2000 | Misawa et al. |
| 6,207,409 | B1 | 3/2001 | Hohmann et al. |
| 6,214,575 | B1 | 4/2001 | Yano et al. |
| 6,291,204 | B1 | 9/2001 | Pasamontes et al. |
| 6,306,639 | B1 | 10/2001 | Woods et al. |
| 6,528,314 | B1 | 3/2003 | Le Mouellic et al. |
| 6,677,134 | B2 | 1/2004 | Pasamontes et al. |
| 6,929,928 | B2 | 8/2005 | Cheng et al. |
| 6,969,595 | B2 | 11/2005 | Brzostowicz et al. |
| 6,989,472 | B1 | 1/2006 | Carol et al. |
| 7,063,957 | B2 | 6/2006 | Chen |
| 7,064,196 | B2 | 6/2006 | Cheng et al. |
| 7,070,952 | B2 | 7/2006 | Cheng et al. |
| 7,074,604 | B1 | 7/2006 | Tang et al. |
| 7,091,031 | B2 | 8/2006 | Cheng et al. |
| 7,118,896 | B2 | 10/2006 | Kalscheuer et al. |

(Continued)

FOREIGN PATENT DOCUMENTS

| | | | |
|---|---|---|---|
| CN | 1177002 | A | 3/1998 |
| CN | 1528902 | A | 9/2004 |

(Continued)

OTHER PUBLICATIONS

Elizabeth A. Specht et al. Front Microbiol. Published on Feb. 17, 2014, vol. 5—2014 | https://doi.org/10.3389/fmicb.2014.00060.*

(Continued)

*Primary Examiner* — Bao Q Li
(74) *Attorney, Agent, or Firm* — COOLEY LLP

(57) ABSTRACT

The present disclosure provides oral antigenic compositions comprising a recombinant *Spirulina* comprising at least one exogenous antigenic epitope. Oral antigenic compositions of the present disclosure can be used as vaccines. Oral antigenic compositions of the present disclosure can be used to induce a protective immune response to infectious microorganism, tumor antigens, or self-antigens.

12 Claims, 26 Drawing Sheets

Specification includes a Sequence Listing.

(Continued)

(56) References Cited

U.S. PATENT DOCUMENTS

| | | | |
|---|---|---|---|
| 7,157,619 | B1 | 1/2007 | Lassner et al. |
| 7,176,000 | B2 | 2/2007 | Glazer et al. |
| 7,217,537 | B2 | 5/2007 | Miller, Jr. et al. |
| 7,223,909 | B2 | 5/2007 | Hauptmann et al. |
| 7,232,665 | B2 | 6/2007 | Cheng et al. |
| 7,232,666 | B2 | 6/2007 | Sharpe et al. |
| 7,252,964 | B2 | 8/2007 | Giraud et al. |
| 7,252,985 | B2 | 8/2007 | Cheng et al. |
| 7,288,387 | B2 | 10/2007 | Cheng et al. |
| 7,291,482 | B2 | 11/2007 | Cheng et al. |
| 7,385,123 | B2 | 6/2008 | Sauer et al. |
| 7,393,671 | B2 | 7/2008 | Cheng et al. |
| 7,422,873 | B2 | 9/2008 | Stead et al. |
| 7,425,625 | B2 | 9/2008 | Tang et al. |
| 7,427,593 | B1 | 9/2008 | Dahlqvist et al. |
| 7,498,026 | B2 | 3/2009 | Dahlqvist et al. |
| 7,504,236 | B2 | 3/2009 | Miller, Jr. et al. |
| 7,522,162 | B2 | 4/2009 | Cubicciotti |
| 7,695,931 | B2 | 4/2010 | Nishida et al. |
| 7,695,932 | B2 | 4/2010 | Stephanopoulos et al. |
| 7,741,070 | B2 | 6/2010 | Stephanopoulos et al. |
| 7,794,696 | B2 | 9/2010 | Van et al. |
| 7,794,969 | B1 | 9/2010 | Reppas et al. |
| 7,999,151 | B2 | 8/2011 | Choi et al. |
| 8,030,022 | B2 | 10/2011 | Tanaka et al. |
| 8,110,670 | B2 | 2/2012 | Hu et al. |
| 8,394,614 | B2 | 3/2013 | Roberts et al. |
| 8,394,621 | B2 | 3/2013 | Roberts et al. |
| 8,569,014 | B2 | 10/2013 | Tanaka et al. |
| 8,835,137 | B2 | 9/2014 | Roberts et al. |
| 9,029,120 | B2 | 5/2015 | Roberts et al. |
| 9,040,264 | B2 | 5/2015 | Kristof et al. |
| 9,523,096 | B2 | 12/2016 | Roberts et al. |
| 9,914,907 | B2 | 3/2018 | Roberts et al. |
| 10,131,870 | B2 * | 11/2018 | Takeuchi ............... C12N 15/74 |
| 10,336,982 | B2 | 7/2019 | Takeuchi et al. |
| 10,415,012 | B2 | 9/2019 | Takeuchi et al. |
| 10,415,013 | B2 | 9/2019 | Takeuchi et al. |
| 10,563,168 | B2 | 2/2020 | Roberts et al. |
| 10,654,901 | B2 | 5/2020 | Roberts et al. |
| 10,760,045 | B2 | 9/2020 | Roberts et al. |
| 10,787,488 | B2 | 9/2020 | Roberts et al. |
| 11,174,294 | B2 | 11/2021 | Roberts et al. |
| 11,279,912 | B2 | 3/2022 | Roberts et al. |
| 12,065,638 | B2 | 8/2024 | Takeuchi et al. |
| 12,252,513 | B2 | 3/2025 | Roberts et al. |
| 2003/0003528 | A1 | 1/2003 | Brzostowicz et al. |
| 2003/0104379 | A1 | 6/2003 | Lagarias et al. |
| 2003/0148319 | A1 | 8/2003 | Brzostowicz et al. |
| 2003/0233675 | A1 | 12/2003 | Cao et al. |
| 2004/0077068 | A1 | 4/2004 | Brzostowicz et al. |
| 2004/0078846 | A1 | 4/2004 | Desouza et al. |
| 2004/0219629 | A1 | 11/2004 | Cheng et al. |
| 2004/0224383 | A1 | 11/2004 | Cheng et al. |
| 2005/0003474 | A1 | 1/2005 | Desouza et al. |
| 2005/0260699 | A1 | 11/2005 | Desouza et al. |
| 2005/0281839 | A1 | 12/2005 | Belay et al. |
| 2006/0053513 | A1 | 3/2006 | Steiger et al. |
| 2006/0059584 | A1 | 3/2006 | Klebsattel et al. |
| 2006/0088550 | A1 | 4/2006 | Bachmann et al. |
| 2006/0099670 | A1 | 5/2006 | Matuschek et al. |
| 2006/0099710 | A1 | 5/2006 | Donnelly et al. |
| 2006/0121468 | A1 * | 6/2006 | Allnutt ..................... C12N 7/00 435/6.12 |
| 2006/0121557 | A1 | 6/2006 | Hoshino et al. |
| 2006/0137043 | A1 | 6/2006 | Puzio et al. |
| 2006/0185038 | A1 | 8/2006 | De Block |
| 2006/0234333 | A1 | 10/2006 | Matuschek et al. |
| 2007/0059790 | A1 | 3/2007 | Miller, Jr. et al. |
| 2007/0065900 | A1 | 3/2007 | Dicosimo et al. |
| 2007/0065901 | A1 | 3/2007 | Dicosimo et al. |
| 2007/0065902 | A1 | 3/2007 | Dicosimo et al. |
| 2007/0065903 | A1 | 3/2007 | Dicosimo et al. |
| 2007/0269859 | A1 | 11/2007 | Lassner et al. |
| 2008/0107652 | A1 | 5/2008 | Durvasula et al. |
| 2008/0124755 | A1 | 5/2008 | Louie et al. |
| 2008/0160592 | A1 | 7/2008 | Dahlqvist et al. |
| 2008/0193970 | A1 | 8/2008 | Fardoux et al. |
| 2008/0301839 | A1 | 12/2008 | Ravanello |
| 2009/0035832 | A1 | 2/2009 | Koshland, Jr. |
| 2009/0142322 | A1 | 6/2009 | Ye |
| 2009/0155864 | A1 | 6/2009 | Bauer et al. |
| 2009/0175911 | A1 | 7/2009 | Cutting et al. |
| 2009/0197321 | A1 | 8/2009 | Chiou et al. |
| 2009/0203070 | A1 | 8/2009 | Devroe et al. |
| 2009/0215179 | A1 | 8/2009 | Gressel et al. |
| 2009/0220537 | A1 | 9/2009 | Tindle et al. |
| 2009/0226582 | A1 | 9/2009 | Ide et al. |
| 2009/0298143 | A1 | 12/2009 | Roessler et al. |
| 2010/0068776 | A1 | 3/2010 | Woods et al. |
| 2010/0081178 | A1 | 4/2010 | Roberts et al. |
| 2010/0184169 | A1 | 7/2010 | Roberts et al. |
| 2010/0251601 | A1 | 10/2010 | Hu et al. |
| 2010/0255551 | A1 | 10/2010 | Roberts et al. |
| 2011/0053216 | A1 | 3/2011 | Vermaas |
| 2011/0072714 | A1 | 3/2011 | Gaertner |
| 2011/0129474 | A1 | 6/2011 | Shoemaker et al. |
| 2011/0184152 | A1 | 7/2011 | Adams et al. |
| 2011/0244532 | A1 | 10/2011 | Hu et al. |
| 2011/0250659 | A1 | 10/2011 | Roberts et al. |
| 2011/0250663 | A1 | 10/2011 | Schirmer et al. |
| 2011/0252501 | A1 | 10/2011 | Abad et al. |
| 2011/0277190 | A1 | 11/2011 | Abad |
| 2012/0115208 | A1 | 5/2012 | Ellison et al. |
| 2012/0142082 | A1 | 6/2012 | Sharpe et al. |
| 2012/0252080 | A1 | 10/2012 | Kristof et al. |
| 2013/0039889 | A1 | 2/2013 | McDonagh et al. |
| 2013/0058962 | A1 | 3/2013 | Shoemaker et al. |
| 2013/0078686 | A1 | 3/2013 | Holtzapple et al. |
| 2013/0143284 | A1 | 6/2013 | Roberts et al. |
| 2013/0171677 | A1 | 7/2013 | Bryant et al. |
| 2013/0224811 | A1 | 8/2013 | Holtzapple et al. |
| 2013/0230537 | A1 | 9/2013 | Hussack et al. |
| 2013/0344549 | A1 | 12/2013 | Roberts et al. |
| 2014/0004580 | A1 | 1/2014 | Roberts et al. |
| 2014/0011264 | A1 | 1/2014 | Duhring et al. |
| 2014/0030785 | A1 | 1/2014 | Kallas et al. |
| 2014/0325710 | A1 | 10/2014 | Abad et al. |
| 2014/0356867 | A1 | 12/2014 | Peter et al. |
| 2015/0024442 | A1 | 1/2015 | Roberts et al. |
| 2015/0329868 | A1 | 11/2015 | Hickman et al. |
| 2016/0046902 | A1 | 2/2016 | Roberts et al. |
| 2017/0240872 | A1 | 8/2017 | Guo et al. |
| 2017/0240944 | A1 | 8/2017 | Heinnickel et al. |
| 2017/0298319 | A1 | 10/2017 | Takeuchi et al. |
| 2018/0051057 | A1 | 2/2018 | Roberts et al. |
| 2018/0134755 | A1 | 5/2018 | Roberts et al. |
| 2018/0222945 | A1 | 8/2018 | Roberts et al. |
| 2018/0305660 | A1 | 10/2018 | Takeuchi et al. |
| 2018/0312801 | A1 | 11/2018 | Takeuchi et al. |
| 2019/0002820 | A1 | 1/2019 | Takeuchi et al. |
| 2019/0062763 | A1 | 2/2019 | Roberts et al. |
| 2019/0093066 | A1 | 3/2019 | Roberts et al. |
| 2020/0017822 | A1 | 1/2020 | Takeuchi et al. |
| 2020/0172859 | A1 | 6/2020 | Roberts et al. |
| 2020/0392189 | A1 | 12/2020 | Roberts et al. |
| 2021/0047610 | A1 | 2/2021 | Roberts et al. |
| 2021/0338751 | A1 | 11/2021 | Roberts et al. |
| 2022/0135627 | A1 | 5/2022 | Roberts et al. |
| 2024/0002481 | A1 | 1/2024 | Roberts |
| 2024/0150440 | A1 | 5/2024 | Roberts et al. |
| 2025/0075170 | A1 | 3/2025 | Takeuchi et al. |

FOREIGN PATENT DOCUMENTS

| | | | |
|---|---|---|---|
| CN | 1608132 | A | 4/2005 |
| CN | 1843150 | A | 10/2006 |
| CN | 101173214 | A | 5/2008 |
| CN | 103382482 | A | 11/2013 |
| CN | 103820459 | A | 5/2014 |
| CN | 104311649 | A | 1/2015 |
| CN | 104450766 | A | 3/2015 |
| CN | 104479010 | A | 4/2015 |
| CN | 104480133 | A | 4/2015 |

(56) References Cited

FOREIGN PATENT DOCUMENTS

CN 108495685 A 9/2018
CN 112094342 A 12/2020
EP 0157253 A1 10/1985
EP 0393690 A1 10/1990
EP 0872554 A2 10/1998
EP 1854889 A1 11/2007
JP H06253863 A 9/1994
JP H1156360 A 3/1999
JP 200424232 1/2004
JP 2006075097 A 3/2006
JP 2006191919 A 7/2006
JP 2006520254 A 9/2006
JP 3874897 B2 1/2007
JP 2011512841 A 4/2011
JP 2015535224 A 12/2015
JP 2017526372 A 9/2017
JP 6253863 B1 12/2017
KR 100788479 B1 12/2007
KR 100845582 B1 7/2008
KR 20090046376 A 5/2009
KR 20100051306 A 5/2010
SG 187250 A1 * 3/2013 ........... A01N 1/0221
TW 200811098 A 3/2008
WO WO-9839457 A1 9/1998
WO WO-9963055 A1 12/1999
WO WO-0241833 A2 5/2002
WO WO-02097137 A1 12/2002
WO WO-2004003143 A2 * 1/2004 ............. A61K 39/12
WO WO-2004029234 A1 4/2004
WO WO-2004087892 A1 10/2004
WO WO-2006078050 A2 7/2006
WO WO-2006096392 A2 9/2006
WO WO-2007136762 A2 11/2007
WO WO-2008119082 A2 10/2008
WO WO-2008130437 A2 10/2008
WO WO-2009009391 A2 1/2009
WO WO-2009010826 A2 1/2009
WO WO-2009036095 A1 3/2009
WO WO-2009042950 A1 4/2009
WO WO-2009062190 A2 5/2009
WO WO-2009076559 A1 6/2009
WO WO-2009089185 A1 7/2009
WO WO-2009098089 A2 8/2009
WO WO-2009111513 A1 9/2009
WO WO-2009140696 A2 11/2009
WO WO-2010006312 A2 1/2010
WO WO-2010017245 A1 2/2010
WO WO-2010019813 A2 2/2010
WO WO-2010021711 A1 2/2010
WO WO-2010022090 A1 2/2010
WO WO-2010027516 A2 3/2010
WO WO-2010033921 A2 3/2010
WO WO-2010036951 A2 4/2010
WO WO-2010042664 A2 4/2010
WO WO-2010044960 A1 4/2010
WO WO-2010048568 A1 4/2010
WO WO-2010062480 A2 6/2010
WO WO-2010062707 A1 6/2010
WO WO-2010075440 A1 7/2010
WO WO-2010075483 A2 7/2010
WO WO-2010078584 A1 7/2010
WO WO-2010104763 A1 9/2010
WO WO-2010118410 A1 10/2010
WO WO-2010126891 A1 11/2010
WO WO-2010130725 A1 11/2010
WO WO-2011008535 A1 1/2011
WO WO-2011008565 A1 1/2011
WO WO-2011011568 A2 1/2011
WO WO-2011018116 A1 2/2011
WO WO-2011029013 A2 3/2011
WO WO-2011038132 A1 3/2011
WO WO-2011038134 A1 3/2011
WO WO-2011052003 A1 5/2011
WO WO-2011059745 A1 5/2011
WO WO-2011127069 A1 10/2011
WO WO-2011127118 A1 10/2011
WO WO-2012017199 A1 2/2012
WO WO-2012033870 A1 3/2012
WO WO-2012087963 A1 6/2012
WO WO-2012087982 A2 6/2012
WO WO-2013116517 A2 8/2013
WO WO-2014013489 A1 1/2014
WO WO-2014063253 A1 5/2014
WO WO-2014164232 A1 10/2014
WO WO-2014164566 A2 10/2014
WO WO-2016040499 A1 3/2016
WO WO-2016044336 A1 3/2016
WO WO-2016073562 A1 5/2016
WO WO-2016172438 A1 10/2016
WO WO-2017011273 A1 1/2017
WO WO-2017066468 A1 4/2017
WO WO-2017139687 A1 8/2017
WO WO-2019222711 A1 11/2019
WO WO-2020018586 A1 1/2020
WO WO-2022140696 A1 6/2022

OTHER PUBLICATIONS

Ruma Ariria Soni et al. Trends in Food Science &Technology, vol. 69, Part A, Nov. 2017, pp. 157-171.*

David Dauvillée et al. PloS One 2010, vol. 5, issue 12, e15424, pp. 1-8.*

Macete et al. Tropical Medicine and International Health 2007, vol. 12, No. 1, pp. 37-46.*

Wilipedia printer by Feb. 28, 2024, pp. 1-2.*

Barzegari et al. "The Search for a Promising Cell Factory System for Production of Edible Vaccine," Human Vaccines & Immunotherapeutics 10(8):2497-2502 (2014).

International Search Report and Written Opinion issued by the International Searching Authority for Application No. PCT/US2019/032998, dated Aug. 5, 2019, 9 pages.

A935Y7—UniProtKB Database—2008, 2 pages.

Adir et al. "Structure of c-Phycocyanin from the Thermophilic Cyanobacterium *Synechococcus vulcan* us at 2.5 A: Structural Implications for Thermal Stability in Phycobilisome Assembly", 2001, vol. 313, p. 71-81.

Agarwal et al., "Gastrointestinal and Liver Manifestations of COVID-19," J Clin Exp Hepatol. May-Jun. 2020; 10(3): 263-265. Published online Apr. 1, 2020.

Akiyama, et al., "Nucleotide Sequence of Plasmid pAG1 of Marine Cyanobacterium *Synechococcus* sp. PCC7002", DNA Res., 1998, vol. 5, pp. 127-129.

Altschul et al., Basic Local Alignment Search Tool, Journal of molecular biology, Oct. 1990, pp. 403-410.

Alvarez et al., "Triacylglycerols in prokaryotic microorganisms," Appl. Microbial. Biotechnol. 60:367-376, 2002.

Alvey et al., "Attachment of noncognate chromophores to CpcA of *Synechocystis* sp. PCC 6803 and *Synechococcus* sp. PCC 7002 by heterologous expression in *Escherichia coli*.," Biochemistry 50(22):4890-4902 (2011).

Alvey et al., "Effects of Modified Phycobilin Biosynthesis in the Cyanobacterium *Synechococcus* sp. Strain PCC 7002,"Journal of Bacteriology, 193(7):1663-1671 (2011).

Alvin, J. W and Lacy, D.B., Clostridium difficile toxin glucosyltransferase domains in complex with a non-hydrolyzable UDP-glucose analogue. J Struct Bioi. Jun. 2017;198(3):203-209. doi: 10.1016/j.jsb.2017.04.006. Epub Apr. 19, 2017. PMID: 28433497; PMCID:PMC5534367. (Year: 2017).

Ambati et al., "Astaxanthin: Sources, Extraction, Stability, Biological Activities and its Commercial Applications—a Review", Marine Drugs, Jan. 2014, vol. 12, 25 pgs.

Andersen K, et.al., "Neutralization of Clostridium difficile Toxin B Mediated by Engineered Lactobacilli That Produce Single-Domain Antibodies", Infection and Immunity, Nov. 2015, vol. 84 No. 2, pp. 395-406.

Angermayr, et al., "Engineering a cyanobacterial cell factory for production of lactic acid," (2012) Applied and Environmental Microbiology 78: 7098-7106 (2012).

(56) References Cited

OTHER PUBLICATIONS

Anonymous: UPI0000000F3D, Jul. 23, 2007 (Jul. 23, 2007),Retrieved from the Internet: URL:https://www.uniprot.org/uniparcUPI0000000F3D [retrieved on Nov. 8, 2018], 3 pages.
Anonymous: UPI0000000F3E, Jan. 23, 2007 (Jan. 23, 2007), Retrieved from the Internet: URL:https://www.uniprot.org/uniparc/UPI0000000F3E [retrieved on Nov. 8, 2018], 3 pages.
Anonymous: UPI00001BA0B6, Oct. 1, 2003 (Oct. 1, 2003), XP055522054,Retrieved from the Internet: URL:https://www.uniprot.org/uniparc/UPI00001BA0B6 [retrieved on Nov. 8, 2018], 2 pages.
Anonymous: UPI00001BA0C5, Oct. 1, 2003 (Oct. 1, 2003), Retrieved from the Internet: URL:https://www.uniprot.org/uniparc/UPI00001BA0C5[retrieved on Nov. 8, 2018], 2 pages.
Anonymous: UPI00001BA0CB, Oct. 1, 2003 (Oct. 1, 2003), Retrieved from the Internet: URL:https://www.uniprot.org/uniparc/UPI00001BA0CB[retrieved on Nov. 8, 2018], 2 pages.
"Appln. Environ. Microbiol.," American Society for Microbiology, Jun. 15, 2012, 14 pages.
"Arthrospira platensis NIES-39 ," Taxonomy Browser, https://www.ncbi.nlm.nih.gov/Taxonomy/Browser/wwwtax.cgi?id=696747, 2023, pp. 1-2.
Assiri et al., "Epidemiological, demographic, and clinical characteristics of 47 cases of Middle East respiratory syndrome coronavirus disease from Saudi Arabia: a descriptive study," Lancet Infect Dis Sep. 2013;13(9):752-61.
Bailey, et al., "Photoprotection in Cyanobacteria: Regulation of Light Harvesting", Photochemistry and Photobiology, vol. 84, No. 6, Nov. 1, 2008, pp. 1410-1420.
Ballicora et al., "ADP-Glucose Pyrophosphorylase, a Regulatory Enzyme for Bacterial Glycogen Synthesis", Microbiology and Molecular Biology Reviews, Jun. 2003, vol. 67, No. 2, 14 pgs.
Barrera., et al. "Algal chloroplast produced camelid VHH antitoxins are capable of neutralizing botulinum neurotoxin." Plant biotechnology journal 13.1 (2015): 117-124. (Year: 2015).
Beckmann, et al., "Improvement of light to biomass conversion by de-regulation of light-harvesting protein translation in Chlamydomonas reinhardtii", Journal of Biotechnology, vol. 142, No. 1, Jun. 1, 2009, Elsevier Science Publishers, pp. 70-77.
Bhattacharya et al., "Evaluation of Three Spirulina Species Grown Under Similar Conditions for Their Growth and Biochemicals," Journal of the Science of Food and Agriculture, 2005, vol. 85, pp. 333-336.
Biswas, Avijit, "Identification and characterization of enzymes involved in the biosynthesis of different phycobiliproteins in cyanobacteria" ( 2011). University of New Orleans Theses and Dissertations. 446. Retrieved from the Internet Nov. 19, 2018: URL:https://scholarworks.uno.edu/cgi/viewcontent.cgi?referer=https://www.bing.com/&httpsredir=l&article=1244&context=td, 211 pages.
Blot et al., "Phycourobilin in Trichromatic Phycocyanin from Oceanic Cyanobacteria Is Formed Post-translationally by a Phycoerythrobilin Lyase-Isomerase," J. Biol. Chem., 284(14):9290-8 (2009).
Bouvier-Nave, et al., "Expression in yeast and tobacco of plant cDNAs encoding acyl CoA: diacylglycerol acyltransferase", Eur. J. Biochem, 2000, vol. 267, pp. 85-96.
Buikema et al., "Expression of the Anabaena hetR gene from a copper-regulated promoter leads to heterocyst differentiation under repressing conditions," Proc. Natl. Acad. Sci. USA, 98:2729-2734 (2001).
Burgers et al., "Structure of smAKAP and its regulation by PKA-mediated phosphorylation," FEBS J. 283(11):2132-2148 (2016).
Buschiazzo et al., "Crystal structure of Glycogen Synthase: Homologous Enzymes Catalyze Glycogen Synthesis and Degradation", The EMBO Journal, Jul. 2004, vol. 23, No. 16, 10 pgs.
Cai Y.A., et al., "Recombinant Phycobiliproteins: Recombinant C-Phycocyanins Equipped with Affinity Tags, Oligomerization, and Biospecific Recognition Domains," Analytical Biochemistry, Mar. 2001, vol. 290(2), pp. 186-204.
Cao Breeding and characterization of amino acid-analogue-resistant mutants of Arthrospira platensis. World Journal of Microbiology and Biotechnology, Rapid Communications of Oxford 30. 423-428 (2013).
Chen, et al., "Structure of the full-length Clostridium difficile toxin B." Nature structural & molecular biology 26.8 (2019): 712-719. (Year: 2019).
Christensen et al., "Lipid domains of mycobacteria studied with fluorescent molecular probes," Molecular Microbiology V 31(5):1561-1572, 1999.
Christie, "Coenzyme A and Acyl Carrier Protein: Structure, Occurrence, Biology and Analysis", retrieved on Sep. 14, 2012, at lipidlibrary.aocs.org, Scottish Crop Research Institute, Feb. 24, 2011, pp. 1-4.
Chung et al., "Insertional inactivation studies of the csmA and csmC genes of the green sulfur bacterium Chlorobium vibrioforme 8327: the chlorosome protein CsmA is required for viability but CsmC is dispensable," FEMS Microbiol. Lett., 1998; 164: 353-361.
Chungjatupornchai et al., "Isolation and Characterization of Synechococcus PCC7942 Promoters: tRNApro Gene Functions as a Promoter" Current Microbiology 38: 210-216, 1999.
Coates et al., "Characterization of Cyanobacterial Hydrocarbon Composition and Distribution of Biosynthetic Pathways", PLOS one, vol. 9, Jan. 2014, pp. 1-12.
Cohen et al., "Construction of biologically functional bacterial plasmids in vitro," Proc. Natl. Acad Sci. US.A. 70:3240-3244 (Nov. 1973).
Coleman et al., "Physiological and Nutritional Regulation of Enzymes of TriacylglycerolSynthesis," Annu. Rev. Nutr. 20:77-103, Jan. 1, 2000.
Cooper, et al., "Evolution of Thermal Dependence of Growth Rate of *Escherichia coli* Populations during 20,000 Generations in a Constant Environment", Evolution, vol. 55, No. 5, 2001, pp. 889-896.
Courchesne, et al., "Enhancement of lipid production using biochemical, genetic and transcription factor engineering approaches", Journal of Biotechnology, Elsevier Science Publishers, Amsterdam, NL, vol. 141, No. 1-2, Apr. 20, 2009, pp. 31-41.
Crawford et al., "Protocol and Reagents for Pseudotyping Lentiviral Particles with SARS-COV-2 Spike Protein for Neutralization Assays," Viruses. May 6, 2020;12(5):513, 15 pages.
Dahlqvist, et al., "Phospholipid:diacylglycerol acyltransferase: An enzyme that catalyzes the acyl-CoA-independent formation of triacylglycerol in yeast and plants." Proc Natl Acad Sci USA (2000); 97 (12): 6487-6492.
Daniel et al., "Induction of a Novel Class of Diacylglycerol Acyltransferases and Triacylglycerol Accumulation in *Mycobacterium tuberculosis* as It Goes into a Dormancy-Like State in Culture" Journal of Bacteriology 186(15): 5017-5030, Aug. 2004.
Database Uniprot entry P00308. C-phycocyanin-1 alpha chain. [online]. Oct. 24, 2015 [retrieved Nov. 17, 2016). Available on the internet: , 2 pages.
Database Uniprot entry P00312. C-phycocyanin-1 beta chain. [online]. Jun. 24, 2015, 6 pages retrieved Nov. 17, 2016). Available on the internet: , 3 pages.
Daum et al., "Biochemistry, Cell Biology and Molecular Biology of Lipids of *Saccharomyces cerevisiae*," Yeast 14:1471-1510, 1998.
David et al. "High-Resolution Crystal Structures of Trimeric and Rod Phycocyanin," Journal of Molecular Biology 405(1):201-213 (2010).
Davis et al., "Overproduction of Acetyl-CoA Carboxylase Activity Increases the Rate of Fatty Acid Biosynthesis in *Escherichia coli*," The Journal of Biological Chemistry 275(37):28593-28598, Sep. 15, 2000.
De Philippis et al., "Exocellular polysaccharides from cyanobacteriaand their possible applications," FEMS Microbiol. Reviews, 1998; 22:151-175.
Dehghani J, et.al., "Stable transformation of Spirulina (Arthrospira) platensis: a promising microalga for production of edible vaccines", Applied Microbiology and Biotechnology, Nov. 2018, vol. 102 No. 21, pp. 9267-9278.

(56) References Cited

OTHER PUBLICATIONS

Devereux et al. "A comprehensive set of sequence analysis programs for the VAX" Nucleic Acids Research 12(1):387-395 (Jan. 11, 1984).
Dobrikova AG et al, "Effect of partial or complete elimination of light-harvesting complexes on the surface electric properties and the functions of cyanobacterial photosynthetic membranes", Physiologia Plantarum, 2013, 147(2):248-260 Epub Jun. 22, 2012.
Dong et al, "Four Different Methods Comparison for Extraction of Astaxanthin from Green Alga *Haematococcus dluvialis*", The Scientific World Journal, vol. 2014, Jan. 2014, Article ID 694305, 6 pgs.
Dorne et al., "Do thylakoids really contain phosphatidylcholine?" Proc. Natl. Acad. Sci. USA, vol. 87, Jan. 1990, pp. 71-74.
Ducat et al. "Engineering Cyanobacteria to Generate High Value Products", Review, Special Issue—Applied Microbiology, Trends in Biotechnology, Feb. 2011, vol. 29, No. 2, 9 pgs.
Duran et al., "The efficient functioning of photosynthesis and respiration in *Synechocystis* sp. PCC 6803 strictly requires the presence of either cytochrome c6 or plastocyanin," J. of Biol. Chem., 2004; 279:7229-7233.
Espinosa et al., "Cross-talk and Regulatory Interactions Between the Essential Response Regulator Rpab and Cyanobacterial Circadian Clock Output," Proceedings of the National Academy of Sciences, 12(7):2198-2203 (2015).
Extended European Search Report for Application No. EP21194272.7, mailed on Dec. 13, 2021, 12 pages.
Extended European Search Report for European Application No. EP20834359 dated Jun. 30, 2023,7 pages.
Fang et al., "Rapid mutation of Spirulina platensis by a new mutagenesis system of atmospheric and room temperature plasmas (ARTP) and generation of a mutant library with diverse phenotypes," PLoS ONE 8, e77046, pp. 1-12 (Oct. 2013).
Fass, D., "Disulfide bonding in protein biophysics." Annu Rev Biophys (2012); 41: 63-79. Epub Dec. 20, 2011.
Fen Wang, "Construction and Transformation of Spirulina platensis Expression Vector" (Chinese Language), Chinese Master's Theses Full-text Database—Basic Sciences, Issue 9, 56 pages including English translation (2009).
Fu et al., "Mass-Spectral Identification and Purification of Phycoerythrobilin and Phycocyanobilin," J. Biochem. 179:1-6 (1979).
Fujisawa et al, "Genomic Structure of an Economically Important Cyanobacterium, Arthrospira (Spirulina) Platensis NIES-39", DNA Research 17, Advance Access Publication Mar. 2010, pp. 85-103.
Fukui et al. "Relationship between color development and protein conformation in the phycocyanin molecule", 2004, Dyes and Pigments, vol. 63, p. 89-94.
Gao, et al., "A Novel Cyanophage with a Cyanobacterial Nonbleaching Protein A Gene in the Genome", Journal of Virology, Jan. 2012, vol. 86, No. 1, pp. 236-245.
GenBank, Accession No. BX569694.1, Feb. 2015, www.ncbi.nlm.nih.gov.
GenBank Accession No. CP000100. Synechococcus elongatus PCC 7942, complete genome (Dec. 2007), 3 pages.
Giallourou et al., "A novel mouse model of Campylobacter jejuni enteropathy and diarrhea," PLoS Pathog. 14(3): e1007083, pp. 1-23 (2018).
Gibson, et al., "Enzymatic assembly of DNA molecules up to several hundred kilobases." Nature Methods (Apr. 12, 2009); 6(5): 343-345.
Glazer et al. "Fluorescent tandem phycobiliprotein conjugates", Sep. 1983, Biophysical Journal, vol. 43, p. 383-386.
Gormley et al., "Pathogen cross-transmission via building sanitary plumbing systems in a full scale pilot test-rig," PLOS ONE Feb. 10, 2017, 13 pages.
Gribskov and Burgess, "Sigma factors from *E. coli*, B. subtilis, phage SP01, and phage T4 are homologous proteins", Nucleic Acids Res. Aug. 26, 1986; 14(16): 6745-63.
Gu et al., "COVID-19: Gastrointestinal Manifestations and Potential Fecal-Oral Transmission," Gastroenterology. May 2020;158(6):1518-1519. Epub Mar. 3, 2020.
Hallmann et al., "Gene replacement by homologous recombination in the multicellular green alga *Volvox carteri*," Proc. Natl. Acad. USA, 1997; 94:7469-7474.
Han et al., "Digestive Symptoms in COVID-19 Patients With Mild Disease Severity: Clinical Presentation, Stool Viral RNA Testing, and Outcomes," Am J Gastroenterol. Jun. 2020;115(6):916-923.
Han et al., "The Cellular Functions of the Yeast Lipin Homolog Pahlp are Dependent on Its Phosphatidate Phosphatase Activity" The Journal of Biological Chemistry 282(51): 37026-37035, Dec. 21, 2007.
Han et al., "The *Saccharomyces cerevisiae* Lipin Homolog Is a Mg2+-dependent Phosphatidate Phosphatase Enzyme" The Journal of Biological Chemistry 281(14): 9210-9218, Apr. 7, 2006.
Harker et al, "Biosynthesis of Ketocarotenoids in Transgenic Cyanobacteria Expressing the Algal Gene for B-C-4-Oxygenase, crtO", FEBS Letters 404, Jan. 1997, 6 pgs.
Harwood, "Recent advances in the biosynthesis of plant fatty acids", Biochimica et Biophysica ACTA (BBA)—Lipids and Lipid Metabolism, vol. 1301, No. 1-2, May 1, 1996, pp. 7-56.
Hasunuma et al. "Overexpression of flv3 improves photosynthesis in the cyanobacterium *Synechocystis* sp. PCC6803 by enhancement of alternative electron flow," Biotechnology for Biofuels (Dec. 2014) 7:493, pp. 1-10.
He et al., "The high light-inducible polypeptides in Synechocystis PCC6803. Expression and function in high light," J. Biol. Chem., 2001; 276:306-314.
Herranen et al., "Regulation of photosystem I reaction center genes in Synechocystis sp. strain PCC 6803 during Light acclimation," Plant Cell Physiol., 2005; 46:1484-1493.
Hickman et al, "Glycogen Synthesis is a Required Component of the Nitrogen Stress Response in Synechococcus Elongatus PCC 7942", Algal Research, Feb. 2013, pp. 98-106.
Hiroaki Kato et al: "Interactions Between Histidine Kinase NblS and the Response Regulators RpaB and SrrA are Involved in the Bleaching Process of the Cyanobacterium *Synechococcus elongatus* PCC 7942",Plant and Cell Physiology 52(12):2115-2122 (2011).
Hobbs, et al., "Cloning of a cDNA encoding diacylglycerol acyltransferase from *Arabidopsis thaliana* and its functional expression." FEBS Lett (1999); 452 (3): 145-149.
Hofvander et al., "A prokaryotic acyl-CoA reductase performing reduction of fatty acyl-CoA to fatty alcohol", Elsevier B. B., FEBS Letters, Federation of European Biochemical Societies, 2011, 585, 6 pages.
Hu et al., "Microalgal triacylglycerols as feedstocks for biofuel production: perspectives and advances", The Plant Journal, vol. 54, 2008, pp. 621-639.
Imamura et al., "Growth Phase-dependent Activation of Nitrogen-related Genes by a Control Network of Group 1 and Group 2 Factors in a Cyanobacterium," J. Biol. Chem., 281:2668-2675 (2006).
Imashimizu et al, "Thymine at-5 Is Crucial for cpc Promoter Activity of *Synechocystis* sp. Strain PCC 6714", Journal of Bacteriology, Nov. 2013, vol. 185, No. 21, 4 pgs.
International Search Report and Written Opinion issued by the International Searching Authority for Application No. PCT/US2020/040794, dated Oct. 19, 2020, 15 pages.
International Search Report and Written Opinion issued by the International Searching Authority for Application No. PCT/US2022/013529, mailed May 6, 2022, 9 pages.
Ip et al. "pH-induced conformational changes of AcrA, the membrane fusion protein of *Escherichia coli* multidrug efflux system," Journal of Biological Chemistry 278(50):50474-50482 (2003).
Iwai et al., "Improved genetic transformation of the thermophilic cyanobacterium, *Thermosynechococcus elongatus* BP-1," Plant Cell Physiol., 2004; 45:171-175.
Jako, et al., "Seed-Specific Over-Expression of an *Arabidopsis* cDNA Encoding a Diacylglycerol Acyltransferase Enhances Seed Oil Content and Seed Weight." Plant Physiol (2001); 126 (2): 861-874.

(56) References Cited

OTHER PUBLICATIONS

Jakobiak et al., "The bacterial paromomycin resistance gene, aphH, as a dominant selectable marker in Volvox carteri," Protist, 2004 155:381-393.
Jantaro et al, "Suppression of the Lethality of High Light to a Quadruple HLI Mutant by the Inactivation of the Regulatory Protein PfsR in Synechocystis PCC 6803", Journal of Biological Chemistry, vol. 281, No. 41, Oct. 2006, 10 pgs.
Jeamton et al., Overcoming Intrinsic Restriction Enzyme Barriers Enhances Transformation Efficiency in Arthrospira platensis CI. Plant and Cell Physiology 58, 822-830 (2017).
Jiang et al., "Inhibition of Fatty Acid Synthesis in *Escherichia coli* in the Absence of Phospholipid Synthesis and Release of Inhibition by Thioesterase Action," Journal of Bacteriology 176(10):2814-2821, 1994.
Jin et al, "Crystal Structure of Potato Tuber ADP-Glucose Pyrophosphorylase", The EMBO Journal, Feb. 2005, vol. 24, No. 4, 11 pgs.
Joet et al., "Involvement of a plastid terminal oxidase in plastoquinone oxidation as evidenced by expression of the *Arabidopsis thaliana* enzyme in tobacco," J Biol Chem. (2002) 277:31623-31630.
Jung et al., "Candidate Genes for the Phycoerythrocyanin Subunit Lyase. Biochemical Analysis of pecE and pecF Interposon Mutants," J. Biol. Chem., 270, 12877-12884 (1995).
Kaczmarzyk et al., "Fatty Acid Activation in Cyanobacteria Mediated by Acyl-Acyl Carrier Protein Synthetase Enables Fatty Acid Recycling," Plant Physiology, vol. 152, Mar. 2010, pp. 1598-1610.
Kahn et al., "rpbA controls transcription of the constitutive phycocyanin gene set in Fremyella diplosiphon," J. Bacterial. 179(24): 7695-7704 (1997).
Kaiser et al., "Fatty Aldehydes in Cyanobacteria Are a Metabolically Flexible Precursor for a Diversity of Biofuel Products", PLOS ONE, vol. 8, No. 3, Mar. 11, 2013, 11 pages.
Kalscheuer and Steinbchel, "A Novel Bifunctional Wax Ester Synthase/Acyl-CoA:Diacylglycerol Acyltransferase Mediates Wax Ester and Triacylglycerol Biosynthesis in Acinetobacter calcoaceticus ADP1." The Journal of Biological Chemistry (2002); 278 (10): 8075-8082.
Kalscheuer, et al., "Analysis of Storage Lipid Accumulation in Alcanivorax borkumensis: Evidence for Alternative Triacylglycerol Biosynthesis Routes in Bacteria", Journal of Bacteriology, vol. 189, No. 3, Feb. 2007, pp. 918-928.
Kalscheuer et al., "Microdiesel: *Escherichia coli* engineered for fuel production," Microbiology 152:2529-2536, 2006.
Kalscheuer et al., "Neutral Lipid Biosynthesis in Engineered *Escherichia coli*: Jojoba Oil-Like Wax Esters and Fatty Acid Butyl Esters," Applied and Environmental Microbiology 72(2):1373-1379, 2006.
Karradt, et. al., "NblA, a Key Protein of Phycobilisome Degradation, Interacts with ClpC, a HSP100 Chaperone Partner of a Cyanobaceterial Clp Protease", The Journal of Biological Chemistry vol. 283, No. 47, Nov. 21, 2008, 18 pages.
Kawata et al., "Transformation of Spirulina platensis strain CI (*Arthrospira* sp. PCC9438) with Tn5 transposase-transposon DNA-cation liposome complex," Marine Biotechnology. 6, 355-363 (2004).
Khan Z, et.al., "Nutritional and therapeutic potential of Spirulina", Current Pharmaceutical Biotechnology, Oct. 2005, vol. 6 No. 5, pp. 373-379.
Khozin-Goldberg, et al., "Unraveling algal lipid metabolism: Recent advances in gene identification", Biochimie, Masson, Paris, FR, vol. 93, No. 1, Jan. 1, 2011, pp. 91-100.
Kim et al., "Infection and Rapid Transmission of SARS-CoV-2 in Ferrets," Kim et al., 2020, Cell Host & Microbe 27, 704-709. May 13, 2020.
Kindle et al., Stable nuclear transformation of Chlamydomonas using the Chlamydomonas gene for nitrate reductase, J. Cell Biol., 1989; 109:2589-2601, retrieved from jcb.rupress.org on Nov. 6, 2018.
Kirst et al., "Maximizing photosynthetic efficiency and culture productivity in cyanobacteria upon minimizing the phycobilisome light-harvesting antenna size," Biochim Biophys Acta 1837(10):1653-1654 (2014).
Klanchui et al., Systems Biology and Metabolic Engineering of Arthrospira Cell Factories. Computational and Structural Biotechnology Journal 3(4):e201210015-8, pp. 1-8 (Oct. 2012).
Koksharova et al., "Genetic tools for cyanobacteria," Appl. Micrbiol. Biotechnol. 58:123-137, 2002.
Kurreck, Antisense Technologies, Eur. J. Biochem 2003 270_1628-1644.
Kwon, et al., "Reduced light-harvesting antenna: Consequences on cyanobacterial metabolism and photosynthetic productivity", Algal Research, vol. 2, No. 3, May 24, 2013, pp. 188-195.
Larter, "The Navy is locking down staff at boot camp for up to 90 days," Navy Times, 4 pages, Mar. 25, 2020.
Lazar, E. et al., "Transforming Growth Factor α: Mutation of Aspartic Acid 47 and Leucine 48 Results in Different Biological Activities," Molecular and Cellular Biology, 8(3):1247-1252 (1988).
Lea-Smith, et al., "Phycobilisome-Deficient Strains of *Synechocystis* sp. PCC 6803 Have Reduced Size and Require Carbon-Limiting Conditions to Exhibit Enhanced Productivity," Plant Physiology, vol. 165(2), Jun. 2014, pp. 705-714.
Lenski, et al., "Evolutionary Response of Escherichia coli to Thermal Stress", The American Naturalist, vol. 142, Supplement: Evolutionary Responses to Environmental Stress, 1993, pp. S47-S64.
Leung et al., "Enteric involvement of severe acute respiratory syndrome-associated coronavirus infection," Gastroenterology. Oct. 2003;125(4):1011-1017.
Li et al., "Characterization of *Synechocystis* sp. Strain PCC 6803 and Deltanbl Mutants under Nitrogen-Deficient Conditions", Arch Microbial Jun. 29, 2002, vol. 178, No. 4, pp. 256-266.
Li et al., "Role of air distribution in SARS transmission during the largest nosocomial outbreak in Hong Kong," Indoor Air. Apr. 2005;15(2):83-95. doi: 10.1111/j.1600-0668.2004.00317.x.
Li et al., "Substantial undocumented infection facilitates the rapid dissemination of novel coronavirus (SARS-CoV-2)," Science 2020, 6 pages.
Liang et al, "Carotenoid Biosynthesis in Cyanobacteria: Structural and Evolutionary Scenarios Based on Comparative Genomics", Intl Journal of Biological Sciences, Aug. 2006, 2(4), pp. 197-207.
Liu et al., "CO2-limitation-inducible Green Recovery of fatty acids from cyanobacterial biomass," PNAS Early Edition, www.pnas.org/cgi/doi/10.1073/pnas.1103016108, 2011. (4 pages). es.
Liu et al., "Fatty acid production in genetically modified cyanobacteria," PNAS Early Edition, www.pnas.org/cgi/doi/10.1073/pnas.1103014108, 2011. (6 pages).
Liu et al., "Production and secretion of fatty acids in genetically engineered cyanobacteria," Proc Natl Acad Sci U S A . Jul. 2, 2010, 6 pages.
Lu et al., "Molecular Cloning and Characterization of the pgm Gene Encoding Phosphoglucomutase of *Escherichia coli*", Journal of Bacteriology, Sep. 1994, vol. 176, No. 18, 6 pgs.
Ludwig et al., "Transformation and gene replacement in the facultatively chemoheterotrophic, unicellular cyanobacterium *Synechocystis* sp. PCC6714 by electroporation.," Appl. Microbiol. Biotechnol., 2008; 78:729-735.
Luque et al., "Convergence of two global transcriptional regulators o nitrogen induction of the stress acclimation gene nblA i the cyanobacterium *Synechococcus* sp. PCC 7942," (Molecular Microbiology (2001), 41(4), 937-947).
Lykidis et al., "Genomic prospecting for microbial biodiesel production," U.S. Department of Energy Office of Science, Biological and Environmental Research Program and the University of California, Lawrence Berkeley National Laboratory, 2008. 39 pages.
Maccoll, "Allophycocyanin and energy transfer," Biochima et Biophys Acta. 1657:73-81 (2004).
Macintyre, et al., "Photoacclimation of Photosynthesis Irradiance Response Curves and Photosynthetic Pigments in Microalgae and Cyanobacteria", Journal of Phycology, vol. 38, No. 1, Feb. 1, 2002, pp. 17-38.

(56) References Cited

OTHER PUBLICATIONS

Maddox et al, "Elevated Serum Levels in Human Pregnancy of a Molecule Immunochemically Similar to Eosinophil Granule Major Basic Protein", Journal Exp. Med, vol. 158, Oct. 1983, 16 pgs.
Maeda et al., "cis-acting sequences required for NtcB-dependent, nitrite-responsive positive regulation of the nitrate assimilation operon in the cyanobacterium *Synechococcus* sp. strain Pcc 7942,"J. Bacterial.; 180:4080-4088 (1998).
Makino et al, "Characterization of Cyanobacterial Carotenoid Ketolase CrtW and Hydroxylase CrtR by Complementation Analysis in *Escherichia coli*", Pant Cell Physiology, Oct. 2008, vol. 49, No. 12, 12 pgs.
Mali, et al., "RNA-Guided Human Genome Engineering via Cas9", Science, Feb. 15, 2013, vol. 339(6121), pp. 823-826.
Marin et al., J. Bacteriol., "Salt-Dependent Expression of Glucosylglycerol-Phosphate Synthase, Involved in Osmolyte Synthesis in the Cyanobacterium*Synechocystis* sp. Strain PCC 6803," 2002; 184:2870-2877.
Marin et al., "Osmotic stress in *Synechocystis* sp. PCC 6803: low tolerance towards nonionic osmotic stress results from lacking activation of glucosylglycerol accumulation," Microbiology, 152, p. 2023-2030, Mar. 13, 2006.
Marin et al., Plant Physiol., "Gene Expression Profiling Reflects PhysiologicalProcesses in Salt Acclimation of *Synechocystis*sp. Strain PCC 6803," 2004; 136:3290-3300.
Martelli et al. "Thermal stability improvement of blue colorant C-Phycocyanin from Spirulina platensis for food industry applications," Process Biochemistry 49(1):154-159 (2014).
Mary et al., "Effects of high light on transcripts of stress-associated genes for the cyanobacteria *Synechocystis* sp. PCC 6803 and Prochlorococcus MED4 and MIT9313," Microbiol., 2004; 150:1271-1281.
Matsui et al., "Microbial Interactions Affecting the Natural Transformation of Bacillus Subtilis in a Model Aquatic Ecosystem," FEMS Microbiology Ecology 45(3):211-218 (2003).
Mcdonald et al., "Flexibility In Photosynthetic Electron Transport: The Physiological Role of Plastoquinol Terminal Oxidase (PTOX)," Biochimica et Biophysica Acta (BBA)—Bioenergetics 1807(8):pp. 954-967 (2011).
Mell et al., Natural Competence and the Evolution of DNA Uptake Specificity. Journal of Bacteriology 196:1471-1483 (2014).
Mendez-Alvarez et al., "Transformation of Chlorobium limicola by a plasmid that confers the ability to utilize thiosufate," J. Bacterial., 176:7395-7397 (1994).
Mermet-Bouvier et al., "A Conditional Expression Vector for the Cyanobacteria *Synechocystis* sp. Strains PCC6803 and PCC6714 or *Synechococcus* sp. Strains PCC7942 and PCC6301" Current Microbiology 28: 145-148, 1994.
Mermet-Bouvier et al., "Transfer and Replication ofRSFI0IO-Derived Plasmids in Several Cyanobacteria of the Genera *Synechocystis* and *Synechococcus*," Current Microbiology 27:323-327, 1993.
Miao, et al., "Changes in Photosynthesis and Pigmentation in an agp Deletion Mutant of the Cyanobacterium *Synechocystis* sp.", Biotechnology Letters, Mar. 2003, vol. 25, No. 5, pp. 391-396.
Mongold et al., "Evolutionary Adaptation to Temperature. IV. Adaptation of *Escherichia coli* at a Niche Boundary," Evolution, vol. 50, No. 1, 1996, pp. 35-43.
Moran, "Synechococcus vulcan US J.J.Copeland 1936" page from Algae Base, last updated Apr. 6, 2021. G.M. Guiry in Guiry, M.D. & Guiry, G.M. AlgaeBase. World-wide electronic publication, National University of Ireland, Galway. www.algaebase.org; searched on Oct. 11, 2023. pg. 1-2.
Morgan-Kiss et al., "The *Escherichia coli*fadK (ydiD) Gene Encodes an Anerobically Regulated Short Chain Acyl-CoA Synthetase," The Journal of Biological Chemistry 279(36):37324-37333, 2004.
Moronta-Barrios, et al., "In vivo features of signal transduction by the essential response regulator RpaB from Synechococcus elongatus PCC 7942", Microbiology, vol. 158, No. 5, 2012, pp. 1229-1237.
Muramatsu et al., "Characterization of high-light-responsive promoters of the psaAB genes in *Synechocystis* sp. PCC 6803," Plant Cell Physiol., 47:878-890 (2006).
Nakajima et al., "Improvement of microalgal photosynthetic productivity by reducing the content of light harvesting pigment", Journal of Applied Phycology, Kluwer Academic Publishers, Apr. 1, 1999, pp. 195-201.
Nakajima, et al., "Improvement of photosynthesis in dense microalgal suspension by reduction of light harvesting pigments", Journal of Applied Phycology, vol. 9, Dec. 1, 1997, pp. 503-510.
Nakajima, et al., "Reduced photoinhibition of a phycocyanin-deficient mutant of Synechocystis PCC 6714", Journal of Applied Phycology, vol. 10, No. 5, Jan. 1, 1998, pp. 447-452.
Nakamura et al., "Plastidic Phosphatidic Acid Phosphatases Identified in a Distinct Subfamily of Lipid Phosphate Phosphatases with Prokaryotic Origin," The Journal of Biological Chemistry 282(39):29013-29021, 2007.
NCBI Gene ID 951909 "glgc glucose-1-phosphate adenylyltransferase [*Synechocystis* sp. PCC 6803]" Aug. 2003 downloaded from http://www.ncbi.nlm.nih.gov/gene on Jun. 2, 2011, 2 pages.
NCBI Reference Sequence NC_016640.1, dated Jun. 11, 2013, 1 page.
NCBI taxonomy, 2 pages; https://www.ncbi.nlm.nih.gov/Taxonomy/Browser/wwwtax.cgi?mode=Info&id=118562&1vl=3&1in=f&keep=1 &srchmode=1&unlock; accessed Jul. 19, 2023 (Year: 2023).
Nedbal et al., "A photobioreactor system for precision cultivation of photoautotrophic microorganisms and for high-content analysis of suspension dynamics," Biotechnol. Bioeng., 2008; 100:902-910.
Niederholtmeyer, et al., "Engineering cyanobacteria to synthesize and export hydrophilic products," (2010) Applied and Environmental Microbiology 76: 3462-3466.
Nishizuka, "Intracellular Signaling by Hydrolysis of Phospholipids and Activation of Protein Kinase C" Science 258: 607-614, Oct. 23, 1992.
Page, et al., "Reduction of Photoautotrophic Productivity in the Cyanobacterium *Synechocystis* sp. Strain PCC 6803 bl Phycobilisome Antenna Truncation", Applied and Environmental Microbiology, vol. 78, No. 17, Sep. 1, 2012, pp. 5349-6351.
Perrineau, et al., "Evolution of Salt Tolerance in a Laboratory Reared Population of Chlamydomonas Reinhardtii", Environmental Microbiology, vol. 16, No. 6, 2014, pp. 1755-1766.
Perrone et al., "The Chlamydomonas IDA7 Locus Encodes a 140-kDaDynein Intermediate Chain Required to Assemble the I1 Inner Arm Complex," Molecular Biology of the Cell vol. 9, 3351-3365 (1998).
Qi et al., "Application of the Synechococcus nirA Promoter to Establlish an Inducible Expression System for Engineering the Synechocystis Tocopherol Pathway", Applied and Environmental Microbiology, Oct. 2005, vol. 71, No. 10, 7 pgs.
Qiu et al., "Metabolic engineering of Aeromonas hydrophila for the enhanced production of poly(3-hydroxybutyrate-co-3-hydroxyhexanoate)," Appl. Mircobiol. Biotechnol. 69:537-542, 2006.
Quintana, et al., "Renewable energy from Cyanobacteria: energy production optimization by metabolic pathway engineering," Appl Microbiol Biotechnol 91:471-490 (2011).
Radakovits et al., "Genetic Engineering of Algae for Enhanced Biofuel Production", Eukaryotic Cel, vol. 9, No. 4, Apr. 2010, pp. 486-501.
Ramey et al., Genome Engineering in Cyanobacteria: Where We Are and Where We Need To Go, ACS Synthetic Biol. 4:1186-96 (2015).
Rastogi et al. "Physico-chemical factors affecting the in vitro stability of phycobiliproteins from Phormidium rubidum A09DM", Apr. 29, 2015, Bioresource Technology, vol. 190, p. 219-226.
Riazi et al. Pentavalent Single-Domain Antibodies Reduce Campylobacter jejuni Motility and Colonization in Chickens. PLoS One 8(12):e83928, pp. 1-12 (2013).
Ronen-Tarazi et al, "The Genomic Region of rbcLS in *Synechococcus* sp. PCC 7942 Contains Genes Involved in the Ability to Grow Under Low CO2 Concentration and in Chlorophyll Biosynthesis", Plant Physiol., vol. 108, Aug. 1995, 9 pgs.

(56) References Cited

OTHER PUBLICATIONS

Rosales-Mendoza S., "Algae-based biopharmaceuticals", Cham: Springer, 2016, 172 pages.
Rothan and Byrareddy "The epidemiology and pathogenesis of coronavirus disease (COVID-19) outbreak," J Autoimmun. May 2020;109:102433 5 pages. Epub Feb. 26, 2020.
Ruffing, "Engineered cyanobacteria Teaching an old bug new tricks", Bioengineered Bugs, vol. 2, No. 3, May 1, 2011, Sandia National Laboratories, pp. 136-149.
Ruffing, et al., "Physiological Effects of Free Fatty Acid Production in Genetically Engineered Synechococcus elongatus PCC 7942", Biotechnology and Bioengineering, vol. 109, No. 9, Sep. 9, 2012, pp. 2190-2199.
Saerens et al., "Identification of a Universal VHH Framework to Graft Non-canonical Antigen-binding Loops of Camel Single-domain Antibodies", J. Mol. Biol. (2005) 352, 597-607.
Saha et al., "Cytosolic Triacylglycerol Biosynthetic Pathway in Oilseeds. Molecular Cloning and Expression of Peanut Cytosolic Diacylglycerol Acyltransferase" Plant Physiology 141: 1533-1543, Aug. 2006.
Samartzidou et al., "Transcriptional and posttranscriptional control of mRNA from lrtA, a light-repressed transcript in *Synechococcus* sp. PCC 7002," Plant Physiol., 1998; 117:225-234.
Sato, et. al., "sll1961 is a novel regulator of phycobilisome degradation during nitrogen starvation in the yanobacterium *Synechocystis* sp PCC 6803", FEBS Letters 582, 2008, 4 pages.
Schirmer et al., "Microbial Biosynthesis of Alkanes," Science, vol. 329, Jul. 30, 2010, pp. 559-562.
Sendersky, et. al., "NblC, a novel component required for pigment degradation during starvation in Synechococcus DCC 7942", Molecular Microbiology 58(3), Sep. 22, 2005, 11 pages.
SEQ ID: WP_178888959.1, dated Jun. 7, 2022, 1 page.
Sharp and Li, "The codon Adaptation Index—a measure of directional synonymous codon usage bias, and its potential applications." Nucleic Acids Res (1987); 15(3): 1281-1295.
Singh et al., "Bioactive Compounds from Cyanobacteria and Microalgae: An Overview," Critical Reviews in Biotechnology 25:73-95, 2005.
Skruglewicz, et al., Edible Algae System—(Growing Spirulina in space). Steps to Growing Spirulina Algae. Blog post (online). Element 14. Oct. 17, 2020 [retrieved on Apr. 1, 2022]. Retrieved from the Internet: https://community.element14.com/challenges-projects/design-challenges/1-meter-of-pi/b/blog/posts/blog-1-eas---steps-to-growing-spirulina-algae], 11 pages.
Smith, T.F. and Waterman, M.S., "Comparison of Biosequences," Advances in Applied Mathematics 2(4), Dec. 1981, pp. 482-489.
Song, et al., "Exploitation of Oil-bearing Microalgae for Biodiesel," Chinese Journal of Biotechnology, vol. 24, No. 1, Mar. 1, 2008, pp. 341-348, retrieved on Mar. 1, 2008.
Sorger et al., "Triacylglycerol biosynthesis in yeast," Appl Microbiol Biotechnol, vol. 61, 2003, pp. 289-299.
Steinbrenner et al., "Transformation of the Green Alga *Haematococcus pluvialis* with a Phytoene Desaturase for Accelerated Astaxanthin Biosynthesis," Appl Environ. Microbiol., 2006; 72:7477-7484.
Stoveken, et al., "Bacterial Acyltransferases as an Alternative for Lipase-Catalyzed Acylation for the Production of Oleochemicals and Fuels," Angew. Chem Int. Ed. 47:3688-3694 (2008).
Stoveken, et al., "The Wax Ester Synthase/Acyl Coenzyme A:Diacylglycerol Acyltransferase from *Acinetobacter* sp. Strain ADP1: Characterization of a Novel Type of Acyltransferase." J Bacteriol (2005); 187 (4): 1369-1376.
Su et al. Structural insights into the cold adaptation of the photosynthetic pigment-protein C-phycocyanin from an Arctic cyanobacterium. Biochimica et Biophysica Acta 1858:325-335 (2017).
Sun et al., "Functional complementation of a nitrate reductase defective mutant of a green alga *Dunaliella viridis* by introducing the nitrate reductase gene," (2006) Gene, 377: 140-149 (2006).
Suzuki, et al., "Carbohydrate Metabolism in Mutants of the Cyanobacterium *Synechococcus elongatus* PCC 7942 Defective in Glycogen Synthesis", Applied and Environmental Microbiology, vol. 76, No. 10, May 15, 2010, pp. 3153-3159.
Swanson, et al., "Characterization of Phycocyanin Produced by cpcE and cpcF Mutants and Identification of an Identification of an Intergenic Suppressor of the Defect in Bilin Attachment", The Journal of Biological Chemistry, vol. 267, No. 23, The American Society for Biochemistry and Molecular Biology, Inc., 1992, pp. 16146-16154.
Tan et al., "Establishment of a Micro-Particle Bombardment Transformation System for Dunaliella salina," J. Microbiol., 2005; 43:361-365.
Taton et al. The circadian clock and darkness control natural competence in cyanobacteria. Nature Communications 11(1688) pp. 1-11 (Apr. 2020).
Tilzer et al., "Light-Dependence of Photosynthesis and Growth in Cyanobacteria: Implications for their Dominance in Eutropic Lakes," N. England J. Marine and Freshwater Research. 1987. 21: 401-412).
Toyomizu et al., "Effective transformation of the cyanobacterium *Spirulina platensis* using electroporation," J Applied Phycology. 13, 209-214 (2001).
Uniprot, Accession No. 054715, 2015, www.uniprot.org., 3 pages.
UniProt Accession No. A0A0D2CT51 (A0A0D2CT51_9EURO), Apr. 29, 2015 [online]. [Retrieved on Apr. 6, 2022], 8 pages, Retrieved from the InternetURL:https://www.uniprot.org/uniprot/AOAOD2CT51.
UniProt Accession No. A0A510UPM1 (A0A510UPM1_9CELL), Oct. 16, 2019 [online]. 8 pages, [Retrieved on Apr. 6, 2022]. Retrieved from the Internet URL:https://www.uniprot.org/uniprot/AOA510UPM1.
Uniprot, Accession No. Q7U4P2, 2015, www.uniprot.org., 1 page.
Van Heeke et al., "The N-terminal Cysteine of Human Asparagine Synthetase is Essential for Glutamine-dependent Activity" The Journal of Biological Chemistry 264(33): 19475-19477, Nov. 25, 1989.
Voelker et al., "Alteration of the Specificity and Regulation of Fatty Acid Synthesis of *Escherichia coli* by Expression of a Plant Medium-Chain Acyl-Acyl Carrier Protein Thioesterase," Journal of Bacteriology 176(23):7320-7327, 1994.
Wada et al., "Temperature-Induced Changes in the Fatty Acid Composition of the Cyanobacterium, *Synechocystis* PCC6803", Plant Physiology, American Society of Plant Physiologists, Rockville, MD, US, vol. 92, Jan. 1, 1990, pp. 1062-1069.
Waditee et al., "Overexpression of a Na+/H+ antiporter confers salt tolerance on a freshwater cyanobacterium, making it capable of growth in sea water," PNAS 99(6):4109-4114 (2002).
Waltermann et al., "Key enzymes for biosynthesis of neutral lipid storage compounds in prokaryotes: Properties, function and occurrence of wax ester synthases/acyl-CoA:diacylglycerol acyltransferases", Biochimie 89, 2007, pp. 230-242.
Waltermann et al., "Mechanism of lipid-body formation in prokaryotes: how bacteria fatten up," Molecular Microbiology 55(3):750-763, 2005.
Waltermann et al., "Neutral Lipid Bodies in Prokaryotes: Recent Insights into Structure, Formation, and Relationship to Eukaryotic Lipid Depots," Journal of Bacteriology 187(11):3607-3619, 2005.
Wang, "Conditional Investigation on the Electroporation to Transformation for Spirulina platensis" (Chinese Language), High-tech Communication, Issue 10, 13 pages including English translation (2002).
Wang, et al., "Using a novel lysin to help control Clostridium difficile infections." Antimicrobial Agents and Chemotherapy 59.12 (2015): 7447-7457. (Year: 2015).
Welch et al., "Design Parameters to Control Synthetic Gene Expression in Escherichia coli," PLoS One, Sep. 2009, vol. 4, Issue 9, e7002, 10 pages.
Welch et al., "You're one in a googol: optimizing genes for protein expression," J. of the Royal Society, Interface 6 (Suppl 4):S467-S476 (2009).
WHO, WHO issues consensus document on the epidemiology of SARS, Wkly Epidemiol Rec (WER) 78 (43), 2003: 373-375.
Wirth et al., "Transformation of various species of gram-negative bacteria belonging to 11 different genera bv electroporation," Mal. Gen. Genet. 216:175-177, 1989.
Wrapp et al., "Cryo-EM Structure of the 2019-nCOV Spike in the Prefusion Conformation," bioRxiv, 30 pages. Feb. 15, 2020.

(56) References Cited

OTHER PUBLICATIONS

Wu, et al., "Modification of carbon partitioning to enhance PHB production in *Synechocystis* sp. PCC6803", Enzyme Microb. Technol., 2002, vol. 30, pp. 710-715.
Xiao et al., "Evidence for Gastrointestinal Infection of SARS-CoV-2," Gastroenterol May 2020;158(6):1831-1833, and Supplementary Material pp. E1-E3. Epub Mar. 3, 2020.
Xiaohuan Zheng, "Expression of Human Epidermal Growth Factor hEGF in Spirulina" (Chinese Language), Chinese Master's Theses Full-text Database—Basic Sciences, vol. 12, 9 pages including English translation (2009).
Xu et al., "Characteristics of pediatric SARS-CoV-2 infection and potential evidence for persistent fecal viral shedding," Nat Med, Mar. 13, 2020, 9 pages.
Xu, "Guidelines for Experiments on Marine Organisms" (Chinese), Ocean Press, Jun. 2004, 5 pages (Non-English).
Xue et al., "A New Strategy for Lipid Production by Mix Cultivation of Spirulina Platensis and Rhodotorula Glutinis," Applied Biochemistry and Biotechnology 160(2):498-500 (2010).
Yen et al., "DGAT enzymes and triacylglycerol biosynthesis," Journal of Lipid Research, 49: 2283-2301 (2008).
Yeo et al., "Enteric involvement of coronaviruses: is faecal-oral transmission of SARS-CoV-2 possible?," Lancet Gastroenterol Hepatol. Apr. 2020;5(4):335-337.
Yiwei Zhu, "Construction of luxAB Expression Vector of Spirulina platensis and Electroporation Transformation" (Chinese Language), Chinese Master's Theses Full-text Database-Basic Sciences, Issue S2, 28 pages including English translation (2011).
Yoskikawa, et al., "Single-Laboratory Validation of a Method for the Determination of C-Phycocyanin and Allophycocyanin in Spirulina (Arthrospira) Supplements and Raw Materials by Spectrophotometry", J_ AOAC Int., 2008 Vol. 91 (3), pp. 524-529.
Yu et al., "Production of Eicosapentaenoic Acid by a Recombinant Marine Cyanobacterium, *Synechococcus* sp." Lipids 35(10): 1061-1064, 2000.
Zhang et al., "Crystal Structure of the Carboxyltransferase Domain of Acetyl-Coenzyme a Carboxylase" Science 299: 2064-2067, Mar. 28, 2003.
Zhang et al., "Molecular and serological investigation of 2019-nCoV infected patients: implication of multiple shedding routes," Emerg Microbes Infect. Feb. 17, 2020;9(1):386-389.
Zhang et al., "Molecular effect of FadD on the regulation and metabolism of fatty acid in *Escherichia coli*," FEMS Microbiol. Lett. 259:249-253, 2006.
Zhang et al., "Optimum Conditions for Transformation of *Synechocystis* sp. PCC 6803," J. Microbiol., 2007; 45(5):241-245.
Zhang et al., "Study on the Expression of Transthymosin Gene Spirulina and Its Immune-Enhancing Activity" (Chinese), Fujian Journal of Agriculture, vol. 20, Issue 4, pp. 228-232, published on Dec. 31, 2005).
Zhao et al., "Novel activity of a phycobiliprotein lyase: both the attachment of phycocyanobilin and the isomerization to phycoviolobilin are catalyzed by the proteins PecE and PecF encoded by the phycoerythrocyaninoperon," FEBS Lett., 469:9-13 (2000).
Zhenlian Ke, "Establishment of Transformation and Expression System of Spirulina platensis" (Chinese Language), Chinese Doctor's and Master's Theses Full-text Database (Master's)-Basic Sciences, Issue 1, 41 pages including English translation (2002).
Zhou et al., "The cpcE and cpcF Genes of *Synechococcus* sp. PCC 7002," J. Biol. Chem., 267:16138-16145 (1992).
Durdakova et al., Microalgae/cyanobacteria: the potential green future of vitamin B12 production. Critical Reviews in Food Science and Nutrition, 13 pages.https://doi.org/10.1080/10408398.2022.2130156 (Oct. 12, 2022).
Georgianna and Mayfield, "Exploiting diversity and synthetic biology for the production of algal biofuels," Nature 488(7411):329-35 (Aug. 16, 2012).
Lawson et al., "Proposal to restrict the genus Clostridium Prazmowski to Clostridium butyricum and related species," International Journal of Systematic and Evolutionary Microbiology 66:1009-1016 (2016).
U.S. Appl. No. 12/605,204, filed Oct. 23, 2009, U.S. Pat. No. 8,394,621, Mar. 12, 2013.
U.S. Appl. No. 12/645,228, filed Dec. 22, 2009, U.S. Pat. No. 8,835,137, Sep. 16, 2014.
U.S. Appl. No. 12/794,536, filed Jun. 4, 2010, U.S. Pat. No. 8,394,614, Mar. 12, 2013.
U.S. Appl. No. 13/080,496, filed Apr. 5, 2011, U.S. Pat. No. 8,980,613, Mar. 17, 2015.
U.S. Appl. No. 13/761,025, filed Feb. 6, 2013, U.S. Pat. No. 9,029,120, May 12, 2015.
U.S. Appl. No. 13/995,912, filed Dec. 19, 2011.
U.S. Appl. No. 13/995,925, filed Dec. 19, 2011, U.S. Pat. No. 9,523,096, Dec. 20, 2016.
U.S. Appl. No. 14/376,387, filed Jan. 31, 2013.
U.S. Appl. No. 14/383,853, filed Mar. 4, 2013.
U.S. Appl. No. 14/775,606, filed Mar. 10, 2014, U.S. Pat. No. 9,914,907, Mar. 13, 2018.
U.S. Appl. No. 15/510,028, filed Sep. 9, 2015, U.S. Pat. No. 10,131,870, Nov. 20, 2018.
U.S. Appl. No. 15/511,602, filed Sep. 15, 2015.
U.S. Appl. No. 15/519,499, filed Oct. 14, 2015.
U.S. Appl. No. 15/569,022, filed Apr. 22, 2016, U.S. Pat. No. 10,654,901, May 19, 2020.
U.S. Appl. No. 15/743,114, filed Jul. 7, 2016, U.S. Pat. No. 10,787,488, Sep. 29, 2020.
U.S. Appl. No. 15/879,993, filed Jan. 25, 2018, U.S. Pat. No. 10,563,168, Feb. 18, 2020.
U.S. Appl. No. 16/025,785, filed Jul. 2, 2018, U.S. Pat. No. 10,415,012, Sep. 17, 2019.
U.S. Appl. No. 16/025,789, filed Jul. 2, 2018, U.S. Pat. No. 10,336,982, Jul. 2, 2019.
U.S. Appl. No. 16/076,788, filed Feb. 10, 2017.
U.S. Appl. No. 16/122,250, filed Sep. 5, 2018, U.S. Pat. No. 10,415,013, Sep. 17, 2019.
U.S. Appl. No. 16/570,520, filed Sep. 13, 2019.
U.S. Appl. No. 16/791,550, filed Feb. 14, 2020, U.S. Pat. No. 10,760,045, Sep. 1, 2020.
U.S. Appl. No. 16/874,023, filed May 14, 2020, U.S. Pat. No. 11,174,294, Nov. 16, 2021.
U.S. Appl. No. 16/999,395, filed Aug. 21, 2020, U.S. Pat. No. 11,279,912, Mar. 22, 2022.
U.S. Appl. No. 17/032,323, filed Sep. 25, 2020.
U.S. Appl. No. 17/246,837, filed May 3, 2021.
U.S. Appl. No. 17/260,693, filed Jul. 16, 2019.
U.S. Appl. No. 18/268,844, filed Dec. 23, 2021.
U.S. Appl. No. 18/355,696, filed Jul. 20, 2023.
Algal Resources, vol. 11 No. 1, 2, 2018, p. 58(S02), 8 pages including English machine pages.
Jester et al., "Expression and manufacturing of protein therapeutics in spirulina," bioRxiv, 25 pages (Jan. 27, 2021).
Mohd et al., "Agrobacterium: a potent human pathogen," Reviews in Medical Microbiology. 24(4):94-97 (Oct. 2013).
Pourseif et al., "A domain-based vaccine construct against SARS-CoV-2, the causative agent of COVID-19 pandemic: development of self-amplifying mRNA and peptide vaccines," Bioimpacts. 11(1):65-84. (2021). Epub Dec. 10, 2020.
Proceedings of General Meeting of the Japanese Society for Immunology, vol. 31, 2001, p. 240 (3-B-W17-45-O/P), 8 pages including English machine translation.
Zhang et al., Transformation of Cyanobacteria *Synechococcus* sp. PCC7942 and the expression of thymosin $\alpha1$ using homologous recombination plasmid pUTK, Marine Science, vol. 25, Issue 6, 8 pages including English machine translation (Jun. 30, 2001).
Alterman et al., Inhibition of Rumen Methanogens by a Novel Archaeal Lytic Enzyme Displayed on Tailored Bionanoparticles, Frontiers in Microbiology 9:9:2378, pp. 1-14 (Oct. 9, 2018).
Bach, Horacio, et al. "*Escherichia coli* maltose-binding protein as a molecular chaperone for recombinant intracellular cytoplasmic single-chain antibodies." Journal of molecular biology 312.1 (2001): 79-93. (Year: 2001).
Dixon et al., "Green microalgae biomolecule separations and recovery." Bioresources and Bioprocessing 5.1 (2018): 1-24. (Year: 2018).

(56) References Cited

OTHER PUBLICATIONS

Jester B.W., et al., "Development of Spirulina for the Manufacture and Oral Delivery of Protein Therapeutics," Nature Biotechnology, 2022, vol. 40, pp. 956-964.
Kawata Y et al., "Development of Host Vector Systems for Microalgae III, Transformation of Spirulina Platensis," Bulletin of the Osaka National Research Institute AIST, 1994, vol. 45 No. 2, p. 35-40, (16 pages including English Machine Translation).
Kumar et al., "Growth and biopigment accumulation of cyanobacterium *Spirulina platensis* at different light intensities and temperature." Brazilian Journal of Microbiology 42 (2011): 1128-1135. (Year: 2011).
Lin, L. P., "Microstructure of Spray-Dried and Freeze-Dried Microalgal Powders," Food Structure: vol. 4, No. 2, Article 17 (1985).
Maccoll, "Cyanobacterial Phycobilisomes," Journal of Structural Biology, vol. 124:311-334 (1998).
Muyldermans "Nanobodies: Natural Single-Domain Antibodies" Annual Review of Biochemistry, 2013;82(1):775-797.
Puzorjov et al. "Phycobiliproteins from extreme environments and their potential applications", published online Mar. 19, 2020, Journal of Experimental Botany, vol. 71, Issue 13, p. 3827-3842.
Ryan M.P., et al., "*Brevundimonas* spp: Emerging global opportunistic pathogens," Virulence 9(1):480-493 (2018).
Solomon, Katie, The host immune response to Clostridium difficile infection, Therapeutic Advances in Infectious Disease 1(1):19-35 (2013).
Uniprot, A0A2A2HE75_9EURY, Accession: A0A2AHE75, 2 pages, Feb. 22, 2023 [retrieved Nov. 21, 2024]. Retrieved from the Internet URL: rest.uniprot.org/unisave/A0A2A2HE75?format=txt&versions=14.

* cited by examiner

Murine Malaria (Plasmodium yoelii) Vaccine Construct: Sequence

IHNV Vaccine Construct II – E1E2: Schematic

IHNV Vaccine Construct I – E1E2: Sequence

SEQ ID NO: 30 (amino acid sequence)
SEQ ID NO: 51 (nucleotide sequence)

IHNV Vaccine Construct II – DIII: Schematic

Canine Parvovirus Vaccine Construct I – 2L21 x2: Schematic

Canine Parvovirus Vaccine Construct I - 2L21 x2: Sequence

SEQ ID NO: 28 (amino acid sequence)
SEQ ID NO: 49 (nucleotide sequence)

Canine Parvovirus Vaccine Construct II – 3L17 x4: Schematic

Canine Parvovirus Vaccine Construct II – 3L17 x4: Sequence

Human Malaria (Plasmodium falciparum) Vaccine Construct: Schematic

Human Malaria (Plasmodium falciparum) Vaccine Construct: Sequence

SEQ ID NO: 26 (amino acid sequence)
SEQ ID NO:

Engineering a Stable, Antigenic RSV F Protein for Vaccine Use

PDB 5e0i
Human HepB core trimer of dimers
C-terminal distance 21-21A

Engineering a Stable, Antigenic RSV F Protein for Vaccine Use

PDB 5e0i
"Canyon" from C-term to tip of spike ~33A deep

Engineering a Stable, Antigenic RSV F Protein for Vaccine Use

PDB 5e0i
“Canyon” exit ~27A wide

Engineering a Stable, Antigenic RSV F Protein for Vaccine Use

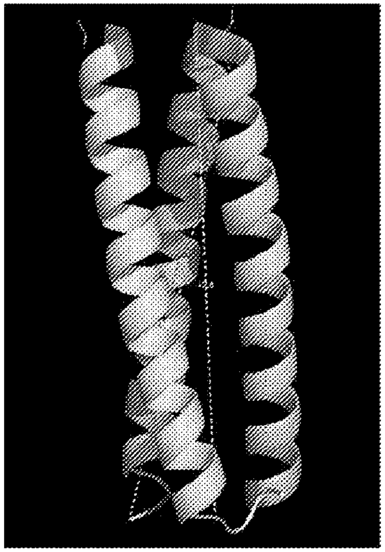

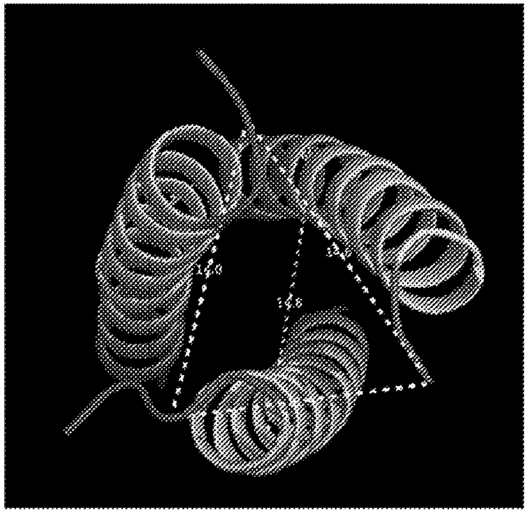

N-Term (red) ~12 A
C-Term (magenta or blue) ~10-12A

Length 43A
Width ~15A

E.Coli codon: CGTATGAAGCAGATAGAGGACAAGATCGA
GGAAATCCTGTCGAAAATCTATCACATTGA
AAATGAGATTGCACGGATAAAGAAATTGAT
TGGTGAAAGA (SEQ ID NO:55)

Spirulina: CGCATGAAACAAATTGAAGATAAAATCGA
AGAGATTCTGAGCAAGATCTATCACATTG
AAAACGAGATTGCTCGTATCAAAAAATTG
ATCGGTGAACGT (SEQ ID NO:56)

PDB: 1GCM (GCN4-pII coiled-coil trimerization domain). DEFINITION Chain A, Gcn4 Leucine Zipper Core Mutant P-Li. ACCESSION 1GCM_A
RMKQIEDKIEEILSKIYHIENEIARIKKLIGER (SEQ ID NO:57)

FIG. 14

Engineering a Stable, Antigenic RSV F Protein for Vaccine Use

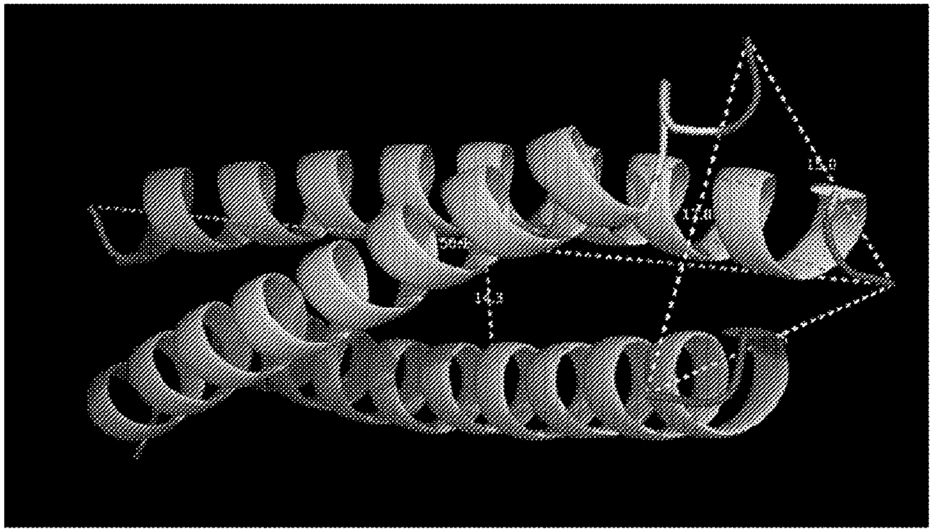

N-Term (red) 14A
C-Term (magenta or blue) ~15-17A

Length 50A
Width ~14A

E. coli: CGTTTACTGCAGCGGATCAAGCAGCAGGAGGATAAACTGGAAGAGACACTGTCTAAGATCTACCATCTGGAGAATGAAATAGCAAGAGTTAAAAAACTGGGAGAGCGC (SEQ ID NO:58)

PDB: 1ce0 (GCN4-pII coiled-coil trimerization domain with mutations from HIV gp41).
RLLQRIKQQEDKLEETLSKIYHLENEIARVKKLGER (SEQ ID NO:60)

Spirulina: CGTTTGCTGCAACGTATTAAGCAACAGGAAGATAAGTTGGAGGAAACTCTGAGCAAGATCTACCACTTGGAAAACGAAATCGCTCGTGTTAAAAAACTGGGCGAGCGT (SEQ ID NO:59)

FIG. 15

Engineering a Stable, Antigenic RSV F Protein for Vaccine Use

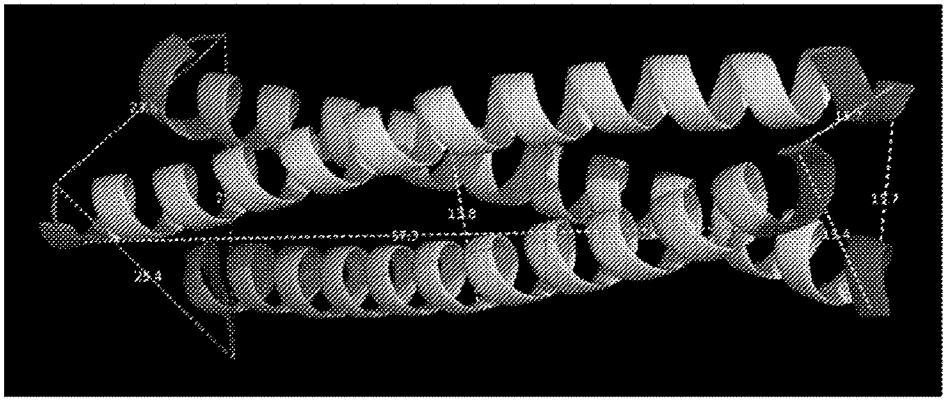

PDB: 2zfc (N-terminal HIV gp41-derived).
QARQLVSGLVQQQNNILRALEATQHAVQALVWGVKQLQARVLALERYIK
(SEQ ID NO:63)

N-Term (red) 24A
C-Term (blue) ~15-16A

Length 57A
Width ~14A

E. coli:
GTGTCGGGGCTTGTACAGCAACAGAACAATATA
CTACGCGCGTTAGAAGCAACCCAGCATGCCGTG
CAGGCCCTGGTGTGGGGCGTAAAGCAGCTTCA
GGCCAGAGTATTAGCACTGGAGCGGTACATTAA
G (SEQ ID NO:61)

Spirulina:
GTGTCCGGCTTGGTGCAACAACAAAACAACATC
CTGCGTGCTCTGGAAGCTACCCAACACGCTGTT
CAAGCCCTGGTGTGGGGTGTTAAACAACTGCAA
GCTCGTGTTTTGGCTTTGGAACGCTACATTAAG
(SEQ ID NO:62)

FIG. 16

GCN4 coiled coil domain linked to N-terminus WHcAg

Axial view Oblique view Lateral view

Juxtaposing GCN4-pII trimerization coiled-coil domain onto the Hepatitis B core protein VLP Three HepB core dimers (PDB: 5wre) shown in green:yellow pairs, with relevant N-termini in magenta
GCN4-derived trimer domain (PDB: 1gcm) shown in cyan, with C-termini in Blue, N-termini in red

SEQUENCE LISTING

<160> NUMBER OF SEQ ID NOS: 70

<210> SEQ ID NO 1
<211> LENGTH: 65
<212> TYPE: PRT
<213> ORGANISM: Artificial Sequence
<220> FEATURE:
<223> OTHER INFORMATION: oligomerization domain

<400> SEQUENCE: 1

```
Ser Ala Gly Ala His Ala Gly Trp Glu Thr Pro Glu Gly Cys Glu Gln
1               5                   10                  15

Val Leu Thr Gly Lys Arg Leu Met Gln Cys Leu Pro Asn Pro Glu Asp
            20                  25                  30

Val Lys Met Ala Leu Glu Val Tyr Lys Leu Ser Leu Glu Ile Glu Gln
        35                  40                  45

Leu Glu Leu Gln Arg Asp Ser Ala Arg Gln Ser Thr Leu Asp Lys Glu
    50                  55                  60

Leu
65
```

<210> SEQ ID NO 2
<211> LENGTH: 55
<212> TYPE: PRT
<213> ORGANISM: Artificial Sequence
<220> FEATURE:
<223> OTHER INFORMATION: oligomerization domain

<400> SEQUENCE: 2

```
Trp Val Ile Pro Glu Gly Cys Gly His Val Leu Ala Gly Arg Lys Val
1               5                   10                  15

Met Gln Cys Leu Pro Asn Pro Glu Asp Val Lys Met Ala Leu Glu Val
            20                  25                  30

Tyr Lys Leu Ser Leu Glu Ile Glu Leu Leu Glu Ile Gln Arg Asp Lys
        35                  40                  45

Ala Arg Asp Pro Ala Met Asp
    50                  55
```

<210> SEQ ID NO 3
<211> LENGTH: 52
<212> TYPE: PRT
<213> ORGANISM: Artificial Sequence
<220> FEATURE:
<223> OTHER INFORMATION: oligomerization domain

<400> SEQUENCE: 3

```
Trp Glu Tyr Ala Glu Gly Cys Glu Gln Val Val Lys Gly Lys Lys Leu
1               5                   10                  15

Met Gln Cys Leu Pro Thr Pro Glu Glu Val Arg Leu Ala Leu Glu Val
            20                  25                  30

Tyr Lys Leu Tyr Leu Glu Ile Gln Lys Leu Glu Leu Gln Lys Asp Glu
        35                  40                  45

Ala Lys Gln Ala
    50
```

<210> SEQ ID NO 4
<211> LENGTH: 58
<212> TYPE: PRT
<213> ORGANISM: Artificial Sequence
<220> FEATURE:
<223> OTHER INFORMATION: oligomerization domain

<400> SEQUENCE: 4

```
Trp Val Val Pro Ala Gly Cys Glu Gln Val Ile Ala Gly Arg Glu Leu
1               5                   10                  15

Thr Gln Cys Leu Pro Ser Val Glu Asp Val Lys Met Ala Leu Glu Leu
            20                  25                  30

Tyr Lys Leu Ser Leu Glu Ile Glu Leu Leu Glu Leu Gln Lys Asp Lys
        35                  40                  45

Ala Lys Lys Ser Thr Leu Glu Ser Pro Leu
    50                  55
```

<210> SEQ ID NO 5
<211> LENGTH: 16
<212> TYPE: PRT
<213> ORGANISM: Artificial Sequence
<220> FEATURE:
<223> OTHER INFORMATION: tandem linked antigenic epitope

<400> SEQUENCE: 5

```
Asn Ala Asn Pro Asn Ala Asn Pro Asn Ala Asn Pro Asn Ala Asn Pro
1               5                   10                  15
```

<210> SEQ ID NO 6
<211> LENGTH: 4
<212> TYPE: PRT
<213> ORGANISM: Plasmodium falciparum

<400> SEQUENCE: 6

```
Asn Ala Asn Pro
1
```

<210> SEQ ID NO 7
<211> LENGTH: 4
<212> TYPE: PRT
<213> ORGANISM: Plasmodium falciparum

<400> SEQUENCE: 7

```
Asn Val Asp Pro
1
```

<210> SEQ ID NO 8
<211> LENGTH: 4
<212> TYPE: PRT
<213> ORGANISM: Plasmodium falciparum

<400> SEQUENCE: 8

```
Asn Pro Asp Pro
1
```

<210> SEQ ID NO 9
<211> LENGTH: 40
<212> TYPE: PRT
<213> ORGANISM: Plasmodium falciparum

<400> SEQUENCE: 9

```
Lys Leu Lys Gln Pro Gly Asp Gly Asn Pro Asp Pro Asn Ala Asn Pro
1               5                   10                  15

Asn Val Asp Pro Asn Ala Asn Pro Asn Val Asp Pro Asn Ala Asn Pro
            20                  25                  30

Asn Val Asp Pro Asn Ala Asn Pro
        35                  40
```

<210> SEQ ID NO 10

<211> LENGTH: 20
<212> TYPE: PRT
<213> ORGANISM: Plasmodium falciparum

<400> SEQUENCE: 10

Glu Tyr Leu Lys Lys Ile Gln Asn Ser Leu Ser Thr Glu Trp Ser Pro
1 5 10 15

Cys Ser Val Thr
20

<210> SEQ ID NO 11
<211> LENGTH: 60
<212> TYPE: PRT
<213> ORGANISM: Plasmodium falciparum

<400> SEQUENCE: 11

Asn Ala Asn Pro Asn Ala Asn Pro Asn Ala Asn Pro Asn Ala Asn Pro
1 5 10 15

Asn Ala Asn Pro Asn Ala Asn Pro Asn Ala Asn Pro Asn Ala Asn Pro
20 25 30

Asn Ala Asn Pro Asn Ala Asn Pro Asn Ala Asn Pro Asn Ala Asn Pro
35 40 45

Asn Ala Asn Pro Asn Ala Asn Pro Asn Ala Asn Pro
50 55 60

<210> SEQ ID NO 12
<211> LENGTH: 35
<212> TYPE: PRT
<213> ORGANISM: Plasmodium falciparum

<400> SEQUENCE: 12

Gly Asp Gly Asn Pro Asp Pro Asn Ala Asn Pro Asn Val Asp Pro Asn
1 5 10 15

Ala Asn Pro Asn Val Asp Pro Asn Ala Asn Pro Asn Val Asp Pro Asn
20 25 30

Ala Asn Pro
35

<210> SEQ ID NO 13
<211> LENGTH: 91
<212> TYPE: PRT
<213> ORGANISM: Plasmodium falciparum

<400> SEQUENCE: 13

Gly Asp Gly Asn Pro Asp Pro Asn Ala Asn Pro Asn Val Asp Pro Asn
1 5 10 15

Ala Asn Pro Asn Val Asp Pro Asn Ala Asn Pro Asn Val Asp Pro Asn
20 25 30

Ala Asn Pro Asn Ala Asn Pro Asn Ala Asn Pro Asn Ala Asn Pro Asn
35 40 45

Ala Asn Pro Asn Ala Asn Pro Asn Ala Asn Pro Asn Ala Asn Pro Asn
50 55 60

Ala Asn Pro Asn Ala Asn Pro Asn Ala Asn Pro Asn Ala Asn Pro Asn
65 70 75 80

Ala Asn Pro Asn Ala Asn Pro Asn Ala Asn Pro
85 90

<210> SEQ ID NO 14
<211> LENGTH: 112
<212> TYPE: PRT

<213> ORGANISM: Plasmodium falciparum

<400> SEQUENCE: 14

Asp Gly Asn Asn Glu Asp Asn Glu Lys Leu Arg Lys Pro Lys His Lys
1 5 10 15

Lys Leu Lys Gln Pro Gly Asp Gly Asn Pro Asp Pro Asn Ala Asn Pro
20 25 30

Asn Val Asp Pro Asn Ala Asn Pro Asn Val Asp Pro Asn Ala Asn Pro
35 40 45

Asn Val Asp Pro Asn Ala Asn Pro Asn Ala Asn Pro Asn Ala Asn Pro
50 55 60

Asn Ala Asn Pro Asn Ala Asn Pro Asn Ala Asn Pro Asn Ala Asn Pro
65 70 75 80

Asn Ala Asn Pro Asn Ala Asn Pro Asn Ala Asn Pro Asn Ala Asn Pro
85 90 95

Asn Ala Asn Pro Asn Ala Asn Pro Asn Ala Asn Pro Asn Ala Asn Pro
100 105 110

<210> SEQ ID NO 15
<211> LENGTH: 7
<212> TYPE: PRT
<213> ORGANISM: Plasmodium falciparum

<400> SEQUENCE: 15

His Pro Ser Asp Gly Lys Cys
1 5

<210> SEQ ID NO 16
<211> LENGTH: 4
<212> TYPE: PRT
<213> ORGANISM: Plasmodium falciparum

<400> SEQUENCE: 16

Asp Arg Tyr Ile
1

<210> SEQ ID NO 17
<211> LENGTH: 6
<212> TYPE: PRT
<213> ORGANISM: Plasmodium falciparum

<400> SEQUENCE: 17

Thr Arg Pro His Gly Arg
1 5

<210> SEQ ID NO 18
<211> LENGTH: 58
<212> TYPE: PRT
<213> ORGANISM: Plasmodium yoelii

<400> SEQUENCE: 18

Gln Gly Pro Gly Ala Pro Gln Gly Pro Gly Ala Pro Gln Gly Pro Gly
1 5 10 15

Ala Pro Gln Gly Pro Gly Ala Pro Gln Gly Pro Gly Ala Pro Gln Gly
20 25 30

Pro Gly Ala Pro Gln Glu Pro Pro Gln Gln Pro Pro Gln Gln Pro Pro
35 40 45

Gln Gln Pro Pro Gln Gln Pro Pro Gln Gln
50 55

<210> SEQ ID NO 19
<211> LENGTH: 15
<212> TYPE: PRT
<213> ORGANISM: Plasmodium yoelii

<400> SEQUENCE: 19

Asn Glu Asp Ser Tyr Val Pro Ser Ala Glu Gln Ile Leu Glu Phe
1 5 10 15

<210> SEQ ID NO 20
<211> LENGTH: 66
<212> TYPE: PRT
<213> ORGANISM: Plasmodium falciparum

<400> SEQUENCE: 20

Glu Glu Gly Asn Ala Asn Pro Asn Ala Asn Pro Asn Ala Asn Pro Asn
1 5 10 15

Ala Asn Pro Asn Ala Asn Pro Asn Ala Asn Pro Asn Ala Asn Pro Asn
20 25 30

Ala Asn Pro Asn Ala Asn Pro Asn Ala Asn Pro Asn Ala Asn Pro Asn
35 40 45

Ala Asn Pro Asn Ala Asn Pro Asn Ala Asn Pro Asn Ala Asn Pro Gly
50 55 60

Glu Glu
65

<210> SEQ ID NO 21
<211> LENGTH: 21
<212> TYPE: PRT
<213> ORGANISM: Canine parvovirus

<400> SEQUENCE: 21

Ser Asp Gly Ala Val Gln Pro Asp Gly Gly Gln Pro Ala Val Arg Asn
1 5 10 15

Glu Arg Ala Thr Gly
20

<210> SEQ ID NO 22
<211> LENGTH: 17
<212> TYPE: PRT
<213> ORGANISM: Canine parvovirus

<400> SEQUENCE: 22

Asp Gly Ala Val Gln Pro Asp Gly Gly Gln Pro Ala Val Arg Asn Glu
1 5 10 15

Arg

<210> SEQ ID NO 23
<211> LENGTH: 41
<212> TYPE: PRT
<213> ORGANISM: Artificial Sequence
<220> FEATURE:
<223> OTHER INFORMATION: IHNV E1+E2 epitopes

<400> SEQUENCE: 23

Asp Asp Glu Asn Arg Gly Leu Ile Ala Tyr Pro Thr Ser Ile Arg Ser
1 5 10 15

Leu Ser Val Gly Gly Ser Gly Gly Ser Asp Leu Ile Ser Val Val Tyr
20 25 30

Asn Ser Gly Ser Glu Ile Leu Ser Phe
35 40

<210> SEQ ID NO 24
<211> LENGTH: 108
<212> TYPE: PRT
<213> ORGANISM: Artificial Sequence
<220> FEATURE:
<223> OTHER INFORMATION: IHNV DIII epitope

<400> SEQUENCE: 24

Asp Asp Glu Asn Arg Gly Leu Ile Ala Tyr Pro Thr Ser Ile Arg Ser
1 5 10 15

Leu Ser Val Gly Asn Asp Gly Gly Ser Gly Gly Ser Ser Gln Glu Ile
20 25 30

Lys Ala His Leu Phe Val Asp Lys Ile Ser Asn Arg Val Val Lys Ala
35 40 45

Thr Ser Tyr Gly His His Pro Trp Gly Leu His Gln Ala Cys Met Ile
50 55 60

Glu Phe Cys Gly Gln Gln Trp Ile Arg Thr Asp Leu Gly Asp Leu Ile
65 70 75 80

Ser Val Val Tyr Asn Ser Gly Ser Glu Ile Leu Ser Phe Pro Lys Cys
85 90 95

Glu Asp Lys Thr Val Gly Pro Ala Glu Gly Gly Gly
100 105

<210> SEQ ID NO 25
<211> LENGTH: 242
<212> TYPE: PRT
<213> ORGANISM: Artificial Sequence
<220> FEATURE:
<223> OTHER INFORMATION: P. yoelii CSP B cell epitope in monomer WHcAg

<400> SEQUENCE: 25

Met Asp Ile Asp Pro Tyr Lys Glu Phe Gly Ser Ser Tyr Gln Leu Leu
1 5 10 15

Asn Phe Leu Pro Leu Asp Phe Phe Pro Asp Leu Asn Ala Leu Val Asp
20 25 30

Thr Ala Thr Ala Leu Tyr Glu Glu Glu Leu Thr Gly Arg Glu His Cys
35 40 45

Ser Pro His His Thr Ala Ile Arg Gln Ala Leu Val Cys Trp Asp Glu
50 55 60

Leu Thr Lys Leu Ile Ala Trp Met Ser Ser Asn Ile Thr Ser Gln Gly
65 70 75 80

Pro Gly Ala Pro Gln Gly Pro Gly Ala Pro Gln Gly Pro Gly Ala Pro
85 90 95

Gln Gly Pro Gly Ala Pro Gln Gly Pro Gly Ala Pro Gln Gly Pro Gly
100 105 110

Ala Pro Gln Glu Pro Pro Gln Gln Pro Pro Gln Gln Pro Pro Gln Gln
115 120 125

Pro Pro Gln Gln Pro Pro Gln Gln Glu Gln Val Arg Thr Ile Ile Val
130 135 140

Asn His Val Asn Asp Thr Trp Gly Leu Lys Val Arg Gln Ser Leu Trp
145 150 155 160

Phe His Leu Ser Cys Leu Thr Phe Gly Gln His Thr Val Gln Glu Phe
165 170 175

Leu Val Ser Phe Gly Val Trp Ile Arg Thr Pro Ala Pro Tyr Arg Pro
180 185 190

Pro Asn Ala Pro Ile Leu Ser Thr Leu Pro Glu His Thr Val Ile Asn
195 200 205

Glu Asp Ser Tyr Val Pro Ser Ala Glu Gln Ile Leu Glu Phe Glu Gln
    210                 215                 220

Lys Leu Ile Ser Glu Glu Asp Leu Glu Gln Lys Leu Ile Ser Glu Glu
225                 230                 235                 240

Asp Leu

<210> SEQ ID NO 26
<211> LENGTH: 384
<212> TYPE: PRT
<213> ORGANISM: Artificial Sequence
<220> FEATURE:
<223> OTHER INFORMATION: P. falciparum CSP B cell epitope in tandem
      WHcAg dimer

<400> SEQUENCE: 26

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205

Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Glu Glu Gly Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Ala Asn Pro Asn Ala Asn Pro Asn Ala Asn Pro Asn Ala Asn Pro
        275                 280                 285

Asn Ala Asn Pro Asn Ala Asn Pro Asn Ala Asn Pro Asn Ala Asn Pro
    290                 295                 300

Gly Glu Glu Glu Gln Val Arg Thr Ile Ile Val Asn His Val Asn Asp
305                 310                 315                 320

```
Thr Trp Gly Leu Lys Val Arg Gln Ser Leu Trp Phe His Leu Ser Cys
                325                 330                 335

Leu Thr Phe Gly Gln His Thr Val Gln Glu Phe Leu Val Ser Phe Gly
            340                 345                 350

Val Trp Ile Arg Thr Pro Ala Pro Tyr Arg Pro Pro Asn Ala Pro Ile
        355                 360                 365

Leu Ser Thr Leu Pro Glu His Thr Val Ile His His His His His His
    370                 375                 380


<210> SEQ ID NO 27
<211> LENGTH: 656
<212> TYPE: PRT
<213> ORGANISM: Artificial Sequence
<220> FEATURE:
<223> OTHER INFORMATION: P. falciparum CSP B cell epitope + Salmonella
      fliC sequences in tandem WHcAg dimer

<400> SEQUENCE: 27

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205

Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Glu Glu Gly Ala Gln Val Ile Asn Thr Asn Ser Leu Ser Leu Leu
                245                 250                 255

Thr Gln Asn Asn Leu Asn Lys Ser Gln Ser Ala Leu Gly Thr Ala Ile
            260                 265                 270

Glu Arg Leu Ser Ser Gly Leu Arg Ile Asn Ser Ala Lys Asp Asp Ala
        275                 280                 285

Ala Gly Gln Ala Ile Ala Asn Arg Phe Thr Ala Asn Ile Lys Gly Leu
```

```
    290                 295                 300

Thr Gln Ala Ser Arg Asn Ala Asn Asp Gly Ile Ser Ile Ala Gln Thr
305                 310                 315                 320

Thr Glu Gly Ala Leu Asn Glu Ile Asn Asn Asn Leu Gln Arg Val Arg
                325                 330                 335

Glu Leu Ala Val Gln Ser Ala Asn Ser Thr Asn Ser Gln Ser Asp Leu
            340                 345                 350

Asp Ser Ile Gln Ala Glu Ile Thr Gln Arg Leu Asn Glu Ile Asp Arg
        355                 360                 365

Val Ser Gly Gln Thr Gln Phe Asn Gly Val Lys Val Leu Ala Gln Asp
    370                 375                 380

Asn Thr Leu Thr Ile Gln Val Gly Ala Asn Asp Gly Glu Thr Ile Asp
385                 390                 395                 400

Ile Asp Leu Lys Gln Ile Asn Ser Gln Thr Leu Gly Leu Asp Thr Leu
                405                 410                 415

Asn Val Gln Gly Ser Asn Ala Asn Pro Asn Ala Asn Pro Asn Ala Asn
            420                 425                 430

Pro Asn Ala Asn Pro Asn Ala Asn Pro Asn Ala Asn Pro Asn Ala Asn
        435                 440                 445

Pro Asn Ala Asn Pro Asn Ala Asn Pro Asn Ala Asn Pro Asn Ala Asn
    450                 455                 460

Pro Asn Ala Asn Pro Asn Ala Asn Pro Asn Ala Asn Pro Asn Ala Asn
465                 470                 475                 480

Pro Gly Ser Thr Thr Thr Glu Asn Pro Leu Gln Lys Ile Asp Ala Ala
                485                 490                 495

Leu Ala Gln Val Asp Thr Leu Arg Ser Asp Leu Gly Ala Val Gln Asn
            500                 505                 510

Arg Phe Asn Ser Ala Ile Thr Asn Leu Gly Asn Thr Val Asn Asn Leu
        515                 520                 525

Thr Ser Ala Arg Ser Arg Ile Glu Asp Ser Asp Tyr Ala Thr Glu Val
    530                 535                 540

Ser Asn Met Ser Arg Ala Gln Ile Leu Gln Gln Ala Gly Thr Ser Val
545                 550                 555                 560

Leu Ala Gln Ala Asn Gln Val Pro Gln Asn Val Leu Ser Leu Leu Arg
                565                 570                 575

Gly Glu Glu Glu Gln Val Arg Thr Ile Ile Val Asn His Val Asn Asp
            580                 585                 590

Thr Trp Gly Leu Lys Val Arg Gln Ser Leu Trp Phe His Leu Ser Cys
        595                 600                 605

Leu Thr Phe Gly Gln His Thr Val Gln Glu Phe Leu Val Ser Phe Gly
    610                 615                 620

Val Trp Ile Arg Thr Pro Ala Pro Tyr Arg Pro Pro Asn Ala Pro Ile
625                 630                 635                 640

Leu Ser Thr Leu Pro Glu His Thr Val Ile His His His His His His
                645                 650                 655
```

<210> SEQ ID NO 28
<211> LENGTH: 206
<212> TYPE: PRT
<213> ORGANISM: Artificial Sequence
<220> FEATURE:
<223> OTHER INFORMATION: Canine parvovirus 2L21 peptide epitope in 2x configuration; monomer WhcAg

<400> SEQUENCE: 28

Met Asp Ile Asp Pro Tyr Lys Glu Phe Gly Ser Ser Tyr Gln Leu Leu
1 5 10 15

Asn Phe Leu Pro Leu Asp Phe Phe Pro Asp Leu Asn Ala Leu Val Asp
20 25 30

Thr Ala Thr Ala Leu Tyr Glu Glu Glu Leu Thr Gly Arg Glu His Cys
35 40 45

Ser Pro His His Thr Ala Ile Arg Gln Ala Leu Val Cys Trp Asp Glu
50 55 60

Leu Thr Lys Leu Ile Ala Trp Met Ser Ser Asn Ile Thr Ser Glu Glu
65 70 75 80

Gly Ser Asp Gly Ala Val Gln Pro Asp Gly Gly Gln Pro Ala Val Arg
85 90 95

Asn Glu Arg Ala Thr Gly Gly Gly Ser Ser Asp Gly Ala Val Gln Pro
100 105 110

Asp Gly Gly Gln Pro Ala Val Arg Asn Glu Arg Ala Thr Gly Gly Glu
115 120 125

Glu Glu Gln Val Arg Thr Ile Ile Val Asn His Val Asn Asp Thr Trp
130 135 140

Gly Leu Lys Val Arg Gln Ser Leu Trp Phe His Leu Ser Cys Leu Thr
145 150 155 160

Phe Gly Gln His Thr Val Gln Glu Phe Leu Val Ser Phe Gly Val Trp
165 170 175

Ile Arg Thr Pro Ala Pro Tyr Arg Pro Pro Asn Ala Pro Ile Leu Ser
180 185 190

Thr Leu Pro Glu His Thr Val Ile His His His His His His
195 200 205

<210> SEQ ID NO 29
<211> LENGTH: 238
<212> TYPE: PRT
<213> ORGANISM: Artificial Sequence
<220> FEATURE:
<223> OTHER INFORMATION: Canine parvovirus 3L17 peptide epitope in 4x
configuration; monomer WhcAg

<400> SEQUENCE: 29

Met Asp Ile Asp Pro Tyr Lys Glu Phe Gly Ser Ser Tyr Gln Leu Leu
1 5 10 15

Asn Phe Leu Pro Leu Asp Phe Phe Pro Asp Leu Asn Ala Leu Val Asp
20 25 30

Thr Ala Thr Ala Leu Tyr Glu Glu Glu Leu Thr Gly Arg Glu His Cys
35 40 45

Ser Pro His His Thr Ala Ile Arg Gln Ala Leu Val Cys Trp Asp Glu
50 55 60

Leu Thr Lys Leu Ile Ala Trp Met Ser Ser Asn Ile Thr Ser Glu Glu
65 70 75 80

Gly Asp Gly Ala Val Gln Pro Asp Gly Gly Gln Pro Ala Val Arg Asn
85 90 95

Glu Arg Gly Gly Ser Asp Gly Ala Val Gln Pro Asp Gly Gly Gln Pro
100 105 110

Ala Val Arg Asn Glu Arg Gly Gly Ser Asp Gly Ala Val Gln Pro Asp
115 120 125

Gly Gly Gln Pro Ala Val Arg Asn Glu Arg Gly Gly Ser Asp Gly Ala
130 135 140

Val Gln Pro Asp Gly Gly Gln Pro Ala Val Arg Asn Glu Arg Gly Glu
145 150 155 160

```
Glu Glu Gln Val Arg Thr Ile Ile Val Asn His Val Asn Asp Thr Trp
                165                 170                 175

Gly Leu Lys Val Arg Gln Ser Leu Trp Phe His Leu Ser Cys Leu Thr
            180                 185                 190

Phe Gly Gln His Thr Val Gln Glu Phe Leu Val Ser Phe Gly Val Trp
        195                 200                 205

Ile Arg Thr Pro Ala Pro Tyr Arg Pro Pro Asn Ala Pro Ile Leu Ser
    210                 215                 220

Thr Leu Pro Glu His Thr Val Ile His His His His His His
225                 230                 235


<210> SEQ ID NO 30
<211> LENGTH: 383
<212> TYPE: PRT
<213> ORGANISM: Artificial Sequence
<220> FEATURE:
<223> OTHER INFORMATION: IHNV E1+E2 epitopes in tandem WHcAg dimer

<400> SEQUENCE: 30

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205

Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Pro Gly Gly Ser Gly Asp Asp Glu Asn Arg Gly Leu Ile Ala Tyr
                245                 250                 255

Pro Thr Ser Ile Arg Ser Leu Ser Val Gly Gly Ser Gly Gly Ser Asp
            260                 265                 270

Leu Ile Ser Val Val Tyr Asn Ser Gly Ser Glu Ile Leu Ser Phe Pro
        275                 280                 285
```

```
Gly Gly Ser Gly Glu Gln Val Arg Thr Ile Ile Val Asn His Val Asn
    290                 295                 300

Asp Thr Trp Gly Leu Lys Val Arg Gln Ser Leu Trp Phe His Leu Ser
305                 310                 315                 320

Cys Leu Thr Phe Gly Gln His Thr Val Gln Glu Phe Leu Val Ser Phe
                325                 330                 335

Gly Val Trp Ile Arg Thr Pro Ala Pro Tyr Arg Pro Pro Asn Ala Pro
            340                 345                 350

Ile Leu Ser Thr Leu Pro Glu His Thr Val Ile Glu Gln Lys Leu Ile
        355                 360                 365

Ser Glu Glu Asp Leu Glu Gln Lys Leu Ile Ser Glu Glu Asp Leu
    370                 375                 380


<210> SEQ ID NO 31
<211> LENGTH: 451
<212> TYPE: PRT
<213> ORGANISM: Artificial Sequence
<220> FEATURE:
<223> OTHER INFORMATION: IHNV DIII epitope in tandem WHcAg dimer

<400> SEQUENCE: 31

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Gly Gly Ser Gly Gly Ser Gly Gly Ser Gly Gly
145                 150                 155                 160

Ser Gly Gly Ser Asp Ile Asp Pro Tyr Lys Glu Phe Gly Ser Ser Tyr
                165                 170                 175

Gln Leu Leu Asn Phe Leu Pro Leu Asp Phe Phe Pro Asp Leu Asn Ala
            180                 185                 190

Leu Val Asp Thr Ala Thr Ala Leu Tyr Glu Glu Glu Leu Thr Gly Arg
        195                 200                 205

Glu His Cys Ser Pro His His Thr Ala Ile Arg Gln Ala Leu Val Cys
    210                 215                 220

Trp Asp Glu Leu Thr Lys Leu Ile Ala Trp Met Ser Ser Asn Ile Thr
225                 230                 235                 240

Ser Pro Gly Gly Ser Gly Asp Asp Glu Asn Arg Gly Leu Ile Ala Tyr
                245                 250                 255

Pro Thr Ser Ile Arg Ser Leu Ser Val Gly Asn Asp Gly Gly Ser Gly
            260                 265                 270
```

Gly Ser Ser Gln Glu Ile Lys Ala His Leu Phe Val Asp Lys Ile Ser
275 280 285

Asn Arg Val Val Lys Ala Thr Ser Tyr Gly His His Pro Trp Gly Leu
290 295 300

His Gln Ala Cys Met Ile Glu Phe Cys Gly Gln Gln Trp Ile Arg Thr
305 310 315 320

Asp Leu Gly Asp Leu Ile Ser Val Val Tyr Asn Ser Gly Ser Glu Ile
325 330 335

Leu Ser Phe Pro Lys Cys Glu Asp Lys Thr Val Gly Pro Ala Glu Gly
340 345 350

Gly Gly Pro Ala Gly Gly Ser Gly Glu Gln Val Arg Thr Ile Ile Val
355 360 365

Asn His Val Asn Asp Thr Trp Gly Leu Lys Val Arg Gln Ser Leu Trp
370 375 380

Phe His Leu Ser Cys Leu Thr Phe Gly Gln His Thr Val Gln Glu Phe
385 390 395 400

Leu Val Ser Phe Gly Val Trp Ile Arg Thr Pro Ala Pro Tyr Arg Pro
405 410 415

Pro Asn Ala Pro Ile Leu Ser Thr Leu Pro Glu His Thr Val Ile Glu
420 425 430

Gln Lys Leu Ile Ser Glu Glu Asp Leu Glu Gln Lys Leu Ile Ser Glu
435 440 445

Glu Asp Leu
450

<210> SEQ ID NO 32
<211> LENGTH: 431
<212> TYPE: PRT
<213> ORGANISM: Plasmodium falciparum

<400> SEQUENCE: 32

Met Arg Lys Leu Ala Ile Leu Ser Val Ser Ser Phe Leu Phe Val Glu
1 5 10 15

Ala Leu Phe Gln Glu Tyr Gln Cys Tyr Gly Ser Ser Ser Asn Thr Arg
20 25 30

Val Leu Asn Glu Leu Asn Tyr Asp Asn Ala Gly Thr Asn Leu Tyr Asn
35 40 45

Glu Leu Glu Met Asn Tyr Tyr Gly Lys Gln Glu Asn Trp Tyr Ser Leu
50 55 60

Lys Lys Asn Ser Arg Ser Leu Gly Glu Asn Asp Asp Gly Asn Asn Asn
65 70 75 80

Asn Gly Asp Asn Gly Arg Glu Gly Lys Asp Glu Asp Lys Arg Asp Gly
85 90 95

Asn Asn Glu Asp Asn Glu Lys Leu Arg Lys Pro Lys His Lys Lys Leu
100 105 110

Lys Gln Pro Gly Asp Gly Asn Pro Asp Pro Asn Ala Asn Pro Asn Val
115 120 125

Asp Pro Asn Ala Asn Pro Asn Val Asp Pro Asn Ala Asn Pro Asn Val
130 135 140

Asp Pro Asn Ala Asn Pro Asn Ala Asn Pro Asn Ala Asn Pro Asn Ala
145 150 155 160

Asn Pro Asn Ala Asn Pro Asn Ala Asn Pro Asn Ala Asn Pro Asn Ala
165 170 175

Asn Pro Asn Ala Asn Pro Asn Ala Asn Pro Asn Ala Asn Pro Asn Ala

```
            180                 185                 190

Asn Pro Asn Ala Asn Pro Asn Ala Asn Pro Asn Ala Asn Pro Asn Ala
        195                 200                 205

Asn Pro Asn Ala Asn Pro Asn Ala Asn Pro Asn Ala Asn Pro Asn Ala
    210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
                245                 250                 255

Asn Pro Asn Ala Asn Pro Asn Ala Asn Pro Asn Ala Asn Pro Asn Ala
            260                 265                 270

Asn Pro Asn Ala Asn Pro Asn Ala Asn Pro Asn Ala Asn Pro Asn Ala
        275                 280                 285

Asn Pro Asn Ala Asn Pro Asn Ala Asn Pro Asn Ala Asn Pro Asn Ala
    290                 295                 300

Asn Pro Asn Lys Asn Asn Gln Gly Asn Gly Gln Gly His Asn Met Pro
305                 310                 315                 320

Asn Asp Pro Asn Arg Asn Val Asp Glu Asn Ala Asn Ala Asn Asn Asp
                325                 330                 335

Val Lys Asn Asn Asn Asn Glu Glu Pro Ser Asp Lys His Ile Glu Glu
            340                 345                 350

Tyr Leu Lys Lys Ile Gln Asn Ser Leu Ser Thr Glu Trp Ser Pro Cys
        355                 360                 365

Ser Val Thr Cys Gly Asn Gly Ile Gln Val Arg Ile Lys Pro Gly Ser
    370                 375                 380

Ala Asn Lys Pro Lys Asp Glu Leu Asn Tyr Glu Asn Asp Ile Glu Lys
385                 390                 395                 400

Lys Ile Cys Lys Met Glu Lys Cys Ser Ser Val Phe Asn Val Val Asn
                405                 410                 415

Ser Ser Ile Gly Leu Ile Met Val Leu Ser Phe Leu Phe Leu Asn
            420                 425                 430


<210> SEQ ID NO 33
<211> LENGTH: 434
<212> TYPE: PRT
<213> ORGANISM: Plasmodium falciparum

<400> SEQUENCE: 33

Met Arg Lys Leu Ala Ile Leu Ser Val Ser Ser Phe Leu Phe Val Glu
1               5                   10                  15

Ala Leu Phe Gln Glu Tyr Gln Cys Tyr Gly Ser Ser Ser Asn Thr Arg
            20                  25                  30

Val Leu Asn Glu Leu Asn Tyr Asp Asn Ala Gly Thr Asn Leu Tyr Asn
        35                  40                  45

Glu Leu Glu Met Asn Tyr Tyr Gly Lys Gln Glu Asn Trp Tyr Ser Leu
    50                  55                  60

Lys Lys Asn Ser Arg Ser Leu Gly Glu Asn Asp Asp Gly Asn Asn Asn
65                  70                  75                  80

Asn Gly Asp Asn Gly Arg Glu Gly Lys Asp Glu Asp Lys Arg Asp Gly
                85                  90                  95

Asn Asn Glu Asp Asn Glu Lys Leu Arg Lys Pro Lys His Lys Lys Leu
            100                 105                 110

Lys Gln Pro Gly Asp Gly Asn Pro Asp Pro Asn Ala Asn Pro Asn Val
        115                 120                 125
```

```
Asp Pro Asn Ala Asn Pro Asn Val Asp Pro Asn Ala Asn Pro Asn Val
    130                 135                 140

Asp Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
                165                 170                 175

Asn Pro Asn Ala Asn Pro Asn Ala Asn Pro Asn Ala Asn Pro Asn Ala
            180                 185                 190

Asn Pro Asn Ala Asn Pro Asn Ala Asn Pro Asn Ala Asn Pro Asn Val
        195                 200                 205

Asp Pro Asn Ala Asn Pro Asn Ala Asn Pro Asn Ala Asn Pro Asn Ala
    210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
                245                 250                 255

Asn Pro Asn Ala Asn Pro Asn Ala Asn Pro Asn Ala Asn Pro Asn Ala
            260                 265                 270

Asn Pro Asn Ala Asn Pro Asn Ala Asn Pro Asn Ala Asn Pro Asn Ala
        275                 280                 285

Asn Pro Asn Ala Asn Pro Asn Ala Asn Pro Asn Ala Asn Pro Asn Ala
    290                 295                 300

Asn Pro Asn Ala Asn Pro Asn Lys Asn Asn Gln Gly Asn Gly Gln Gly
305                 310                 315                 320

His Asn Met Pro Asn Asp Pro Asn Arg Asn Val Asp Glu Asn Ala Asn
                325                 330                 335

Ala Asn Asn Asp Glu Asn Asn Asn Asn Glu Glu Pro Ser Asp Lys His
            340                 345                 350

Ile Glu Gln Tyr Leu Lys Lys Ile Gln Tyr Ser Leu Ser Thr Glu Trp
        355                 360                 365

Ser Pro Cys Ser Val Thr Cys Gly Asn Gly Ile Gln Val Arg Ile Lys
    370                 375                 380

Pro Gly Ser Ala Asp Lys Pro Lys Asp Gln Leu Asp Tyr Glu Asn Asp
385                 390                 395                 400

Ile Glu Lys Lys Ile Cys Lys Met Glu Lys Cys Ser Ser Val Phe Asn
                405                 410                 415

Val Val Asn Ser Ser Ile Gly Leu Ile Met Val Leu Ser Phe Leu Phe
            420                 425                 430

Leu Asn


<210> SEQ ID NO 34
<211> LENGTH: 423
<212> TYPE: PRT
<213> ORGANISM: Plasmodium falciparum

<400> SEQUENCE: 34

Met Arg Lys Leu Ala Ile Leu Ser Val Ser Ser Phe Leu Phe Val Glu
1               5                   10                  15

Ala Leu Phe Gln Glu Tyr Gln Cys Tyr Gly Ser Ser Ser Asn Thr Arg
            20                  25                  30

Val Leu Asn Glu Leu Asn Tyr Asp Asn Ala Gly Thr Asn Leu Tyr Asn
        35                  40                  45

Glu Leu Glu Met Asn Tyr Tyr Gly Lys Gln Glu Asn Trp Tyr Ser Leu
    50                  55                  60
```

Lys Lys Asn Ser Arg Ser Leu Gly Glu Asn Asp Asp Gly Asn Asn Asn
65 70 75 80

Asn Gly Asp Asn Gly Arg Glu Gly Lys Asp Glu Asp Lys Arg Asp Gly
85 90 95

Asn Asn Glu Asp Asn Glu Lys Leu Arg Lys Pro Lys His Lys Lys Leu
100 105 110

Lys Gln Pro Gly Asp Gly Asn Pro Asp Pro Asn Ala Asn Pro Asn Val
115 120 125

Asp Pro Asn Ala Asn Pro Asn Val Asp Pro Asn Ala Asn Pro Asn Val
130 135 140

Asp Pro Asn Ala Asn Pro Asn Ala Asn Pro Asn Ala Asn Pro Asn Ala
145 150 155 160

Asn Pro Asn Ala Asn Pro Asn Ala Asn Pro Asn Ala Asn Pro Asn Ala
165 170 175

Asn Pro Asn Ala Asn Pro Asn Ala Asn Pro Asn Ala Asn Pro Asn Ala
180 185 190

Asn Pro Asn Ala Asn Pro Asn Ala Asn Pro Asn Ala Asn Pro Asn Ala
195 200 205

Asn Pro Asn Ala Asn Pro Asn Ala Asn Pro Asn Ala Asn Pro Asn Ala
210 215 220

Asn Pro Asn Ala Asn Pro Asn Ala Asn Pro Asn Ala Asn Pro Asn Ala
225 230 235 240

Asn Pro Asn Ala Asn Pro Asn Ala Asn Pro Asn Ala Asn Pro Asn Ala
245 250 255

Asn Pro Asn Ala Asn Pro Asn Ala Asn Pro Asn Ala Asn Pro Asn Ala
260 265 270

Asn Pro Asn Ala Asn Pro Asn Ala Asn Pro Asn Ala Asn Pro Asn Ala
275 280 285

Asn Pro Asn Ala Asn Pro Asn Ala Asn Pro Asn Lys Asn Asn Gln Gly
290 295 300

Asn Gly Gln Gly His Asn Met Pro Asn Asp Pro Asn Arg Asn Val Asp
305 310 315 320

Glu Asn Ala Asn Ala Asn Asn Ala Val Lys Asn Asn Asn Asn Glu Glu
325 330 335

Pro Ser Asp Lys His Ile Glu Gln Tyr Leu Lys Lys Ile Gln Asn Ser
340 345 350

Leu Ser Thr Glu Trp Ser Pro Cys Ser Val Thr Cys Gly Asn Gly Ile
355 360 365

Gln Val Arg Ile Lys Pro Gly Ser Ala Asn Lys Pro Lys Asp Glu Leu
370 375 380

Asp Tyr Glu Asn Asp Ile Glu Lys Lys Ile Cys Lys Met Glu Lys Cys
385 390 395 400

Ser Ser Val Phe Asn Val Val Asn Ser Ser Ile Gly Leu Ile Met Val
405 410 415

Leu Ser Phe Leu Phe Leu Asn
420

<210> SEQ ID NO 35
<211> LENGTH: 405
<212> TYPE: PRT
<213> ORGANISM: Plasmodium falciparum

<400> SEQUENCE: 35

Met Met Arg Lys Leu Ala Ile Leu Ser Val Ser Ser Phe Leu Phe Val
1 5 10 15

```
Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Ala Asn Pro Asn Ala Asn Pro Asn Val Asp Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Ala Asn Pro Asn Ala Asn Pro Asn Lys Asn Asn Gln Gly Asn Gly
        275                 280                 285

Gln Gly His Asn Met Pro Asn Asp Pro Asn Arg Asn Val Asp Glu Asn
    290                 295                 300

Ala Asn Ala Asn Ser Ala Val Lys Asn Asn Asn Asn Glu Glu Pro Ser
305                 310                 315                 320

Asp Lys His Ile Lys Glu Tyr Leu Asn Lys Ile Gln Asn Ser Leu Ser
                325                 330                 335

Thr Glu Trp Ser Pro Cys Ser Val Thr Cys Gly Asn Gly Ile Gln Val
            340                 345                 350

Arg Ile Lys Pro Gly Ser Ala Asn Lys Pro Lys Asp Glu Leu Asp Tyr
        355                 360                 365

Ala Asn Asp Ile Glu Lys Lys Ile Cys Lys Met Glu Lys Cys Ser Ser
    370                 375                 380

Val Phe Asn Val Val Asn Ser Ser Ile Gly Leu Ile Met Val Leu Ser
385                 390                 395                 400

Phe Leu Phe Leu Asn
                405
```

<210> SEQ ID NO 36
<211> LENGTH: 427

<212> TYPE: PRT
<213> ORGANISM: Plasmodium falciparum

<400> SEQUENCE: 36

Met Arg Lys Leu Ala Ile Leu Ser Val Ser Ser Phe Leu Phe Val Glu
1 5 10 15

Ala Leu Phe Gln Glu Tyr Gln Cys Tyr Gly Ser Ser Ser Asn Thr Arg
20 25 30

Val Leu Asn Glu Leu Asn Tyr Asp Asn Ala Gly Thr Asn Leu Tyr Asn
35 40 45

Glu Leu Glu Met Asn Tyr Tyr Gly Lys Gln Glu Asn Trp Tyr Ser Leu
50 55 60

Lys Lys Asn Ser Arg Ser Leu Gly Glu Asn Asp Asp Gly Asn Asn Asn
65 70 75 80

Asn Gly Asp Asn Gly Arg Glu Gly Lys Asp Glu Asp Lys Arg Asp Gly
85 90 95

Asn Asn Glu Asp Asn Glu Lys Leu Arg Lys Pro Lys His Lys Lys Leu
100 105 110

Lys Gln Pro Gly Asp Gly Asn Pro Asp Pro Asn Ala Asn Pro Asn Val
115 120 125

Asp Pro Asn Ala Asn Pro Asn Val Asp Pro Asn Ala Asn Pro Asn Val
130 135 140

Asp Pro Asn Ala Asn Pro Asn Ala Asn Pro Asn Ala Asn Pro Asn Ala
145 150 155 160

Asn Pro Asn Ala Asn Pro Asn Ala Asn Pro Asn Ala Asn Pro Asn Ala
165 170 175

Asn Pro Asn Ala Asn Pro Asn Ala Asn Pro Asn Ala Asn Pro Asn Ala
180 185 190

Asn Pro Asn Ala Asn Pro Asn Ala Asn Pro Asn Ala Asn Pro Asn Ala
195 200 205

Asn Pro Asn Ala Asn Pro Asn Ala Asn Pro Asn Ala Asn Pro Asn Ala
210 215 220

Asn Pro Asn Ala Asn Pro Asn Ala Asn Pro Asn Ala Asn Pro Asn Ala
225 230 235 240

Asn Pro Asn Ala Asn Pro Asn Ala Asn Pro Asn Ala Asn Pro Asn Ala
245 250 255

Asn Pro Asn Ala Asn Pro Asn Ala Asn Pro Asn Ala Asn Pro Asn Ala
260 265 270

Asn Pro Asn Ala Asn Pro Asn Ala Asn Pro Asn Ala Asn Pro Asn Ala
275 280 285

Asn Pro Asn Ala Asn Pro Asn Ala Asn Pro Asn Ala Asn Pro Asn Lys
290 295 300

Asn Asn Gln Gly Asn Gly Gln Gly His Asn Met Pro Asn Asp Pro Asn
305 310 315 320

Arg Asn Val Asp Glu Asn Ala Asn Ala Asn Asn Ala Val Lys Asn Asn
325 330 335

Asn Asn Glu Glu Pro Ser Asp Lys His Ile Glu Gln Tyr Leu Lys Lys
340 345 350

Ile Gln Asn Ser Leu Ser Thr Glu Trp Ser Pro Cys Ser Val Thr Cys
355 360 365

Gly Asn Gly Ile Gln Val Arg Ile Lys Pro Gly Ser Ala Asn Lys Pro
370 375 380

Lys Asp Glu Leu Asp Tyr Glu Asn Asp Ile Glu Lys Lys Ile Cys Lys
385 390 395 400

```
Met Glu Lys Cys Ser Ser Val Phe Asn Val Val Asn Ser Ser Ile Gly
                405                 410                 415

Leu Ile Met Val Leu Ser Phe Leu Phe Leu Asn
            420                 425


<210> SEQ ID NO 37
<211> LENGTH: 428
<212> TYPE: PRT
<213> ORGANISM: Plasmodium falciparum

<400> SEQUENCE: 37

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Val Asp Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
            260                 265                 270

Ala Asn Pro Asn Ala Asn Pro Asn Ala Asn Pro Asn Ala Asn Pro Asn
        275                 280                 285

Ala Asn Pro Asn Ala Asn Pro Asn Ala Asn Pro Asn Ala Asn Pro Asn
    290                 295                 300

Lys Asn Asn Gln Gly Asn Gly Gln Gly His Asn Met Pro Asn Asp Pro
305                 310                 315                 320

Asn Arg Asn Val Asp Glu Asn Ala Asn Ala Asn Asn Ala Val Lys Asn
                325                 330                 335

Asn Asn Asn Glu Glu Pro Ser Asp Lys His Ile Glu Gln Tyr Leu Lys
```

```
            340                 345                 350

Lys Ile Gln Asn Ser Leu Ser Thr Glu Trp Ser Pro Cys Ser Val Thr
        355                 360                 365

Cys Gly Asn Gly Ile Gln Val Arg Ile Lys Pro Gly Ser Ala Asn Lys
    370                 375                 380

Pro Lys Asp Glu Leu Asp Tyr Glu Asn Asp Ile Glu Lys Lys Ile Cys
385                 390                 395                 400

Lys Met Glu Lys Cys Ser Ser Val Phe Asn Val Val Asn Ser Ser Ile
                405                 410                 415

Gly Leu Ile Met Val Leu Ser Phe Leu Phe Leu Asn
            420                 425


<210> SEQ ID NO 38
<211> LENGTH: 416
<212> TYPE: PRT
<213> ORGANISM: Plasmodium falciparum

<400> SEQUENCE: 38

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
            260                 265                 270

Ala Asn Pro Asn Ala Asn Pro Asn Ala Asn Pro Asn Ala Asn Pro Asn
        275                 280                 285
```

```
Ala Asn Pro Asn Lys Asn Asn Gln Gly Asn Gly Gln Gly His Asn Met
    290                 295                 300

Pro Asn Asp Pro Asn Arg Asn Val Asp Glu Asn Ala Asn Ala Asn Asn
305                 310                 315                 320

Ala Val Lys Asn Asn Asn Asn Glu Glu Pro Ser Asp Lys His Ile Glu
                325                 330                 335

Gln Tyr Leu Lys Lys Ile Gln Asn Ser Leu Ser Thr Glu Trp Ser Pro
            340                 345                 350

Cys Ser Val Thr Cys Gly Asn Gly Ile Gln Val Arg Ile Lys Pro Gly
        355                 360                 365

Ser Ala Asn Lys Pro Lys Asp Glu Leu Asp Tyr Glu Asn Asp Ile Glu
    370                 375                 380

Lys Lys Ile Cys Lys Met Glu Lys Cys Ser Ser Val Phe Asn Val Val
385                 390                 395                 400

Asn Ser Ser Ile Gly Leu Ile Met Val Leu Ser Phe Leu Phe Leu Asn
                405                 410                 415


<210> SEQ ID NO 39
<211> LENGTH: 416
<212> TYPE: PRT
<213> ORGANISM: Plasmodium falciparum

<400> SEQUENCE: 39

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255
```

```
Ala Asn Pro Asn Ala Asn Pro Asn Ala Asn Pro Asn Ala Asn Pro Asn
            260                 265                 270

Ala Asn Pro Asn Ala Asn Pro Asn Ala Asn Pro Asn Ala Asn Pro Asn
        275                 280                 285

Ala Asn Pro Asn Lys Asn Asn Gln Gly Asn Gly Gln Gly His Asn Met
    290                 295                 300

Pro Asn Asp Pro Asn Arg Asn Val Asp Glu Asn Ala Asn Ala Asn Asn
305                 310                 315                 320

Ala Val Lys Asn Asn Asn Asn Glu Glu Pro Ser Asp Lys His Ile Glu
                325                 330                 335

Gln Tyr Leu Lys Lys Ile Gln Asn Ser Leu Ser Thr Glu Trp Ser Pro
            340                 345                 350

Cys Ser Val Thr Cys Gly Asn Gly Ile Gln Val Arg Ile Lys Pro Gly
        355                 360                 365

Ser Ala Asn Lys Pro Lys Asp Glu Leu Asp Tyr Glu Asn Asp Ile Glu
    370                 375                 380

Lys Lys Ile Cys Lys Met Glu Lys Cys Ser Ser Val Phe Asn Val Val
385                 390                 395                 400

Asn Ser Ser Ile Gly Leu Ile Met Val Leu Ser Phe Leu Phe Leu Asn
                405                 410                 415


<210> SEQ ID NO 40
<211> LENGTH: 412
<212> TYPE: PRT
<213> ORGANISM: Plasmodium falciparum

<400> SEQUENCE: 40

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Val Asp Pro Asn Ala Asn Pro Asn Ala Asn Pro Asn Ala Asn Pro Asn
```

```
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
            260                 265                 270

Ala Asn Pro Asn Ala Asn Pro Asn Ala Asn Pro Asn Ala Asn Pro Asn
        275                 280                 285

Lys Asn Asn Gln Gly Asn Gly Gln Gly His Asn Met Pro Asn Asp Pro
    290                 295                 300

Asn Arg Asn Val Asp Glu Asn Ala Asn Ala Asn Asn Ala Val Lys Asn
305                 310                 315                 320

Asn Asn Asn Glu Glu Pro Ser Asp Lys His Ile Glu Gln Tyr Leu Lys
                325                 330                 335

Lys Ile Gln Asn Ser Leu Ser Thr Glu Trp Ser Pro Cys Ser Val Thr
            340                 345                 350

Cys Gly Asn Gly Ile Gln Val Arg Ile Lys Pro Gly Ser Ala Asp Lys
        355                 360                 365

Pro Lys Asp Gln Leu Asp Tyr Glu Asn Asp Ile Glu Lys Lys Ile Cys
    370                 375                 380

Lys Met Glu Lys Cys Ser Ser Val Phe Asn Val Val Asn Ser Ser Ile
385                 390                 395                 400

Gly Leu Ile Met Val Leu Ser Phe Leu Phe Leu Asn
                405                 410


<210> SEQ ID NO 41
<211> LENGTH: 564
<212> TYPE: PRT
<213> ORGANISM: Plasmodium falciparum

<400> SEQUENCE: 41

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
            20                  25                  30

Val Asp Glu Ile Lys Tyr Arg Glu Glu Val Cys Asn Asp Glu Val Asp
        35                  40                  45

Leu Tyr Leu Leu Met Asp Cys Ser Gly Ser Ile Arg Arg His Asn Trp
    50                  55                  60

Val Lys His Ala Val Pro Leu Ala Met Lys Leu Ile Gln Gln Leu Asn
65                  70                  75                  80

Leu Asn Glu Asn Ala Ile His Leu Tyr Leu Asn Ile Phe Ser Asn Ala
                85                  90                  95

Arg Glu Ile Ile Arg Leu His Ser Asp Ala Ser Lys Asn Lys Glu Lys
            100                 105                 110

Ala Leu Ile Ile Ile Lys Ser Leu Leu Asn Thr Asn Leu Pro Tyr Gly
        115                 120                 125

Arg Thr Asn Leu Thr Asp Ala Leu Leu Gln Val Arg Lys His Leu Asn
    130                 135                 140

Asp Arg Ile Asn Arg Glu Asn Ala Asn Gln Leu Val Val Ile Leu Thr
145                 150                 155                 160

Asp Gly Ile Pro Asp Ser Ile Gln Asp Ser Leu Lys Glu Ser Arg Lys
                165                 170                 175
```

```
Leu Asn Asp Arg Gly Val Lys Ile Ala Val Phe Gly Ile Gly Gln Gly
            180                 185                 190

Ile Asn Val Ala Phe Asn Arg Phe Leu Val Gly Cys His Pro Ser Asp
        195                 200                 205

Gly Lys Cys Asn Leu Tyr Ala Asp Ser Ala Trp Glu Asn Val Lys Asn
    210                 215                 220

Val Ile Gly Pro Phe Met Lys Ala Val Cys Val Glu Val Glu Lys Thr
225                 230                 235                 240

Ala Ser Cys Gly Val Trp Asp Glu Trp Ser Pro Cys Ser Val Thr Cys
                245                 250                 255

Gly Lys Gly Thr Arg Ser Arg Lys Arg Glu Ile Leu His Glu Gly Cys
            260                 265                 270

Thr Ser Glu Leu Gln Glu Gln Cys Glu Glu Glu Arg Cys Pro Pro Lys
        275                 280                 285

Arg Glu Pro Leu Asp Val Pro Asp Glu Pro Glu Asp Asp Gln Pro Arg
    290                 295                 300

Pro Arg Gly Asp Asn Phe Ala Val Glu Lys Pro Glu Glu Asn Ile Ile
305                 310                 315                 320

Asp Asn Asn Pro Gln Glu Pro Ser Pro Asn Pro Glu Glu Gly Lys Gly
                325                 330                 335

Glu Asn Pro Asn Gly Phe Asp Leu Asp Glu Asn Pro Glu Asn Pro Pro
            340                 345                 350

Asn Pro Pro Asn Pro Pro Asn Pro Asp Ile Pro Glu Gln Glu Pro Asn
        355                 360                 365

Ile Pro Glu Asp Ser Glu Lys Glu Val Pro Ser Asp Val Pro Lys Asn
    370                 375                 380

Pro Glu Asp Asp Arg Glu Glu Asn Phe Asp Ile Pro Lys Lys Pro Glu
385                 390                 395                 400

Asn Lys His Asp Asn Gln Asn Asn Leu Pro Asn Asp Lys Ser Asp Arg
                405                 410                 415

Tyr Ile Pro Tyr Ser Pro Leu Pro Pro Lys Val Leu Asp Asn Glu Arg
            420                 425                 430

Lys Gln Ser Asp Pro Gln Ser Gln Asp Asn Asn Gly Asn Arg His Val
        435                 440                 445

Pro Asn Ser Glu Asp Arg Glu Thr Arg Pro His Gly Arg Asn Asn Glu
    450                 455                 460

Asn Arg Ser Tyr Asn Arg Lys His Asn Asn Thr Pro Lys His Pro Glu
465                 470                 475                 480

Arg Glu Glu His Glu Lys Pro Asp Asn Asn Lys Lys Lys Gly Gly Ser
                485                 490                 495

Asp Asn Lys Tyr Lys Ile Ala Gly Gly Ile Ala Gly Gly Leu Ala Leu
            500                 505                 510

Leu Ala Cys Ala Gly Leu Ala Tyr Lys Phe Val Val Pro Gly Ala Ala
        515                 520                 525

Thr Pro Tyr Ala Gly Glu Pro Ala Pro Phe Asp Glu Thr Leu Gly Glu
    530                 535                 540

Glu Asp Lys Asp Leu Asp Glu Pro Glu Gln Phe Arg Leu Pro Glu Glu
545                 550                 555                 560

Asn Glu Trp Asn
```

<210> SEQ ID NO 42
<211> LENGTH: 559
<212> TYPE: PRT
<213> ORGANISM: Plasmodium falciparum

<400> SEQUENCE: 42

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
            20                  25                  30

Val Asp Glu Ile Lys Tyr Arg Glu Glu Val Cys Asn Asp Glu Val Asp
        35                  40                  45

Leu Tyr Leu Leu Met Asp Cys Ser Gly Ser Ile Arg Arg His Asn Trp
    50                  55                  60

Val Lys His Ala Val Pro Leu Ala Met Lys Leu Ile Gln Gln Leu Asn
65                  70                  75                  80

Leu Asn Glu Asn Ala Ile His Leu Tyr Val Asn Ile Phe Ser Asn Asn
                85                  90                  95

Ala Lys Glu Ile Ile Arg Leu His Ser Asp Ala Ser Lys Asn Lys Glu
            100                 105                 110

Lys Ala Leu Ile Ile Ile Lys Ser Leu Leu Ser Thr Asn Leu Pro Tyr
        115                 120                 125

Gly Arg Thr Asn Leu Ser Asp Ala Leu Leu Gln Val Arg Lys His Leu
    130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Asn Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
    210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270

Cys Thr Ser Glu Leu Gln Glu Gln Cys Glu Glu Glu Arg Cys Pro Pro
        275                 280                 285

Lys Arg Glu Pro Leu Asp Val Pro Asp Glu Pro Glu Asp Asp Gln Pro
    290                 295                 300

Arg Pro Arg Gly Asp Asn Phe Ala Val Glu Lys Pro Glu Glu Asn Ile
305                 310                 315                 320

Ile Asp Asn Asn Pro Gln Glu Pro Ser Pro Asn Pro Glu Glu Gly Lys
                325                 330                 335

Gly Glu Asn Pro Asn Gly Phe Asp Leu Asp Glu Asn Pro Glu Asn Pro
            340                 345                 350

Pro Asn Pro Asp Ile Pro Glu Gln Glu Pro Asn Ile Pro Glu Asp Ser
        355                 360                 365

Glu Lys Glu Val Pro Ser Asp Val Pro Lys Asn Pro Glu Asp Asp Arg
    370                 375                 380

Glu Glu Asn Phe Asp Ile Pro Lys Lys Pro Glu Asn Lys His Asp Asn
385                 390                 395                 400

Gln Asn Asn Leu Pro Asn Asp Lys Ser Asp Arg Ser Ile Pro Tyr Ser

```
                405                 410                 415

Pro Leu Pro Pro Lys Val Leu Asp Asn Glu Arg Lys Gln Ser Asp Pro
            420                 425                 430

Gln Ser Gln Asp Asn Asn Gly Asn Arg His Val Pro Asn Ser Glu Asp
        435                 440                 445

Arg Glu Thr Arg Pro His Gly Arg Asn Asn Glu Asn Arg Ser Tyr Asn
    450                 455                 460

Arg Lys Tyr Asn Asp Thr Pro Lys His Pro Glu Arg Glu Glu His Glu
465                 470                 475                 480

Lys Pro Asp Asn Asn Lys Lys Lys Gly Gly Ser Asp Asn Lys Tyr Lys
                485                 490                 495

Ile Ala Gly Gly Ile Ala Gly Gly Leu Ala Leu Leu Ala Cys Ala Gly
            500                 505                 510

Leu Ala Tyr Lys Phe Val Val Pro Gly Ala Ala Thr Pro Tyr Ala Gly
        515                 520                 525

Glu Pro Ala Pro Phe Asp Glu Thr Leu Gly Glu Glu Asp Lys Asp Leu
    530                 535                 540

Asp Glu Pro Glu Gln Phe Arg Leu Pro Glu Glu Asn Glu Trp Asn
545                 550                 555


<210> SEQ ID NO 43
<211> LENGTH: 559
<212> TYPE: PRT
<213> ORGANISM: Plasmodium falciparum

<400> SEQUENCE: 43

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
            20                  25                  30

Val Asp Glu Ile Lys Tyr Ser Glu Glu Val Cys Asn Asp Gln Val Asp
        35                  40                  45

Leu Tyr Leu Leu Met Asp Cys Ser Gly Ser Ile Arg Arg His Asn Trp
    50                  55                  60

Val Asn His Ala Val Pro Leu Ala Met Lys Leu Ile Gln Gln Leu Asn
65                  70                  75                  80

Leu Asn Asp Asn Ala Ile His Leu Tyr Val Asn Val Phe Ser Asn Asn
                85                  90                  95

Ala Lys Glu Ile Ile Arg Leu His Ser Asp Ala Ser Lys Asn Lys Glu
            100                 105                 110

Lys Ala Leu Ile Ile Ile Arg Ser Leu Leu Ser Thr Asn Leu Pro Tyr
        115                 120                 125

Gly Arg Thr Asn Leu Thr Asp Ala Leu Leu Gln Val Arg Lys His Leu
    130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Ser Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
    210                 215                 220
```

Asn Val Ile Gly Pro Phe Met Lys Ala Val Cys Val Glu Val Glu Lys
225 230 235 240

Thr Ala Ser Cys Gly Val Trp Asp Glu Trp Ser Pro Cys Ser Val Thr
245 250 255

Cys Gly Lys Gly Thr Arg Ser Arg Lys Arg Glu Ile Leu His Glu Gly
260 265 270

Cys Thr Ser Glu Ile Gln Glu Gln Cys Glu Glu Glu Arg Cys Pro Pro
275 280 285

Lys Trp Glu Pro Leu Asp Val Pro Asp Glu Pro Glu Asp Asp Gln Pro
290 295 300

Arg Pro Arg Gly Asp Asn Ser Ser Val Gln Lys Pro Glu Glu Asn Ile
305 310 315 320

Ile Asp Asn Asn Pro Gln Glu Pro Ser Pro Asn Pro Glu Glu Gly Lys
325 330 335

Asp Glu Asn Pro Asn Gly Phe Asp Leu Asp Glu Asn Pro Glu Asn Pro
340 345 350

Pro Asn Pro Asp Ile Pro Glu Gln Lys Pro Asn Ile Pro Glu Asp Ser
355 360 365

Glu Lys Glu Val Pro Ser Asp Val Pro Lys Asn Pro Glu Asp Asp Arg
370 375 380

Glu Glu Asn Phe Asp Ile Pro Lys Lys Pro Glu Asn Lys His Asp Asn
385 390 395 400

Gln Asn Asn Leu Pro Asn Asp Lys Ser Asp Arg Asn Ile Pro Tyr Ser
405 410 415

Pro Leu Pro Pro Lys Val Leu Asp Asn Glu Arg Lys Gln Ser Asp Pro
420 425 430

Gln Ser Gln Asp Asn Asn Gly Asn Arg His Val Pro Asn Ser Glu Asp
435 440 445

Arg Glu Thr Arg Pro His Gly Arg Asn Asn Glu Asn Arg Ser Tyr Asn
450 455 460

Arg Lys Tyr Asn Asp Thr Pro Lys His Pro Glu Arg Glu Glu His Glu
465 470 475 480

Lys Pro Asp Asn Asn Lys Lys Lys Gly Glu Ser Asp Asn Lys Tyr Lys
485 490 495

Ile Ala Gly Gly Ile Ala Gly Gly Leu Ala Leu Leu Ala Cys Ala Gly
500 505 510

Leu Ala Tyr Lys Phe Val Val Pro Gly Ala Ala Thr Pro Tyr Ala Gly
515 520 525

Glu Pro Ala Pro Phe Asp Glu Thr Leu Gly Glu Glu Asp Lys Asp Leu
530 535 540

Asp Glu Pro Glu Gln Phe Arg Leu Pro Glu Glu Asn Glu Trp Asn
545 550 555

<210> SEQ ID NO 44
<211> LENGTH: 559
<212> TYPE: PRT
<213> ORGANISM: Plasmodium falciparum

<400> SEQUENCE: 44

Met Asn His Leu Gly Asn Val Lys Tyr Leu Val Ile Val Phe Leu Ile
1 5 10 15

Phe Phe Asp Leu Phe Leu Val Asn Gly Arg Asp Val Gln Asn Asn Ile
20 25 30

Val Asp Glu Ile Lys Tyr Arg Glu Glu Val Cys Asn Asp Glu Val Asp
35 40 45

-continued

```
Leu Tyr Leu Leu Met Asp Cys Ser Gly Ser Ile Arg Arg His Asn Trp
    50                  55                  60

Val Lys His Ala Val Pro Leu Ala Met Lys Leu Ile Gln Gln Leu Asn
65                  70                  75                  80

Leu Asn Glu Ser Ala Ile His Leu Tyr Val Asn Ile Phe Ser Asn Asn
                85                  90                  95

Ala Arg Glu Ile Ile Arg Leu His Ser Asp Ala Ser Lys Asn Lys Glu
            100                 105                 110

Lys Ala Leu Ile Ile Ile Lys Ser Leu Leu Ser Thr Asn Leu Pro Tyr
        115                 120                 125

Gly Arg Thr Asn Leu Thr Asp Ala Leu Leu Gln Val Arg Lys His Leu
    130                 135                 140

Asn Asp Arg Ile Asn Arg Glu Asn Ala Ser Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Asn Asp Leu Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
    210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270

Cys Thr Ser Glu Leu Gln Glu Gln Cys Glu Glu Glu Arg Cys Pro Pro
        275                 280                 285

Lys Arg Glu Pro Leu Asp Val Pro His Glu Pro Glu Asp Asp Gln Pro
    290                 295                 300

Arg Pro Arg Gly Asp Asn Phe Ala Val Glu Lys Pro Lys Glu Asn Ile
305                 310                 315                 320

Ile Asp Asn Asn Pro Gln Glu Pro Ser Pro Asn Pro Glu Glu Gly Lys
                325                 330                 335

Gly Glu Asn Pro Asn Gly Phe Asp Leu Asp Glu Asn Pro Glu Asn Pro
            340                 345                 350

Pro Asn Pro Asp Ile Pro Glu Gln Glu Pro Asn Ile Pro Glu Asp Ser
        355                 360                 365

Glu Lys Glu Val Pro Ser Asp Val Pro Lys Asn Pro Glu Asp Asp Arg
    370                 375                 380

Glu Glu Asn Phe Asp Ile Pro Lys Lys Pro Glu Asn Lys His Asp Asn
385                 390                 395                 400

Gln Asn Asn Leu Pro Asn Asp Lys Ser Asp Arg Ser Ile Pro Tyr Ser
                405                 410                 415

Pro Leu Pro Pro Lys Val Leu Asp Asn Glu Arg Lys Gln Ser Asp Pro
            420                 425                 430

Gln Ser Gln Asp Asn Asn Gly Asn Arg His Val Pro Asn Ser Glu Asp
        435                 440                 445

Arg Glu Thr Arg Pro His Gly Arg Asn Asn Glu Asn Arg Ser Tyr Asn
    450                 455                 460
```

-continued

```
Arg Lys Tyr Asn Asp Thr Pro Lys His Pro Glu Arg Glu Glu His Glu
465                 470                 475                 480

Lys Pro Asp Asn Asn Lys Lys Lys Gly Gly Ser Asp Asn Lys Tyr Lys
                485                 490                 495

Ile Ala Gly Gly Ile Ala Gly Gly Leu Ala Leu Leu Ala Cys Ala Gly
            500                 505                 510

Leu Ala Tyr Lys Phe Val Val Pro Gly Ala Ala Thr Pro Tyr Ala Gly
        515                 520                 525

Glu Pro Ala Pro Phe Asp Glu Thr Leu Gly Glu Glu Asp Lys Asp Leu
    530                 535                 540

Asp Glu Pro Glu Gln Phe Arg Leu Pro Glu Glu Asn Glu Trp Asn
545                 550                 555


<210> SEQ ID NO 45
<211> LENGTH: 568
<212> TYPE: PRT
<213> ORGANISM: Plasmodium falciparum

<400> SEQUENCE: 45

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
            20                  25                  30

Val Asp Glu Ile Lys Tyr Arg Glu Glu Val Cys Asn Asp Glu Val Asp
        35                  40                  45

Leu Tyr Leu Leu Met Asp Cys Ser Gly Ser Ile Arg Arg His Asn Trp
    50                  55                  60

Val Asn His Ala Val Pro Leu Ala Met Lys Leu Ile Gln Gln Leu Asn
65                  70                  75                  80

Leu Asn Glu Ser Ala Ile His Leu Tyr Leu Asn Ile Phe Ser Asn Asn
                85                  90                  95

Ala Arg Glu Ile Ile Arg Leu His Ser Asp Ala Ser Lys Asn Lys Glu
            100                 105                 110

Lys Ala Leu Ile Ile Ile Lys Ser Leu Leu Asn Thr Asn Leu Pro Tyr
        115                 120                 125

Gly Arg Thr Asn Leu Thr Asp Ala Leu Leu Gln Val Arg Lys His Leu
    130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Asn Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
    210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270

Cys Thr Ser Glu Leu Gln Glu Gln Cys Glu Glu Glu Arg Cys Pro Pro
        275                 280                 285
```

Lys Arg Glu Pro Leu Asp Val Pro His Glu Pro Glu Asp Asp Gln Pro
290 295 300

Arg Pro Arg Gly Asp Asn Phe Val Val Glu Lys Pro Glu Glu Asn Ile
305 310 315 320

Ile Asp Asn Asn Pro Gln Glu Pro Ser Pro Asn Pro Glu Glu Gly Lys
325 330 335

Gly Glu Asn Pro Asn Gly Phe Asp Leu Asp Glu Asn Pro Glu Asn Pro
340 345 350

Pro Asn Pro Pro Asn Pro Pro Asn Pro Pro Asn Pro Asp Ile Pro Glu
355 360 365

Gln Glu Pro Asn Ile Pro Glu Asp Ser Glu Lys Glu Val Pro Ser Asp
370 375 380

Val Pro Lys Asn Pro Glu Asp Asp Arg Glu Glu Asn Phe Asp Ile Pro
385 390 395 400

Lys Lys Pro Glu Asn Lys His Asp Asn Gln Asn Asn Leu Pro Asn Asp
405 410 415

Lys Ser Asp Arg Tyr Ile Pro Tyr Ser Pro Leu Pro Pro Lys Val Leu
420 425 430

Asp Asn Glu Arg Lys Gln Ser Asp Pro Gln Ser Gln Asp Asn Asn Gly
435 440 445

Asn Arg His Val Pro Asn Ser Glu Asp Arg Glu Thr Arg Pro His Gly
450 455 460

Arg Asn Asn Glu Asn Arg Ser Tyr Asn Arg Lys His Asn Asn Thr Pro
465 470 475 480

Lys His Pro Glu Arg Glu Glu His Glu Lys Pro Asp Asn Asn Lys Lys
485 490 495

Lys Gly Gly Ser Asp Asn Lys Tyr Lys Ile Ala Gly Gly Ile Ala Gly
500 505 510

Gly Leu Ala Leu Leu Ala Cys Ala Gly Leu Ala Tyr Lys Phe Val Val
515 520 525

Pro Gly Ala Ala Thr Pro Tyr Ala Gly Glu Pro Ala Pro Phe Asp Glu
530 535 540

Thr Leu Gly Glu Glu Asp Lys Asp Leu Asp Glu Pro Glu Gln Phe Arg
545 550 555 560

Leu Pro Glu Glu Asn Glu Trp Asn
565

<210> SEQ ID NO 46
<211> LENGTH: 729
<212> TYPE: DNA
<213> ORGANISM: Artificial Sequence
<220> FEATURE:
<223> OTHER INFORMATION: P. yoelii CSP B cell epitope in monomer WHcAg

<400> SEQUENCE: 46
atggacatag atccctataa agaatttggt tcatcttatc agttgttgaa ttttcttcct 60
ttggacttct ttcctgacct taatgctttg gtggacactg ctactgcctt gtatgaagaa 120
gagctaacag gtagggaaca ttgctctccg caccatacag ctattagaca agctttagta 180
tgctgggatg aattaactaa attgatagct tggatgagct ctaacataac ttctcagggt 240
ccaggtgctc cacaaggacc tggagcacct cagggccctg gcgctcccca agggcctgga 300
gcccctcagg gacccggtgc accgcaaggt ccgggcgctc cccaagaacc acctcaacag 360
cctccacagc aacctcctca gcagccacca caacagcccc ctcagcaaga acaagtaaga 420
acaatcatag taaatcatgt caatgatacc tggggactta aggtgagaca aagtttatgg 480
tttcatttgt catgtctcac ttttggacaa catacagttc aagaattttt agtaagtttt 540
ggagtatgga tcagaactcc agctccatat agacctccta atgcacccat tctctcgact 600
cttccggaac atacagtcat taatgaagat agttatgttc cttctgctga acaaatttta 660
gaatttgagc aaaaattaat tagcgaggaa gacctagaac aaaaactgat ctctgaagag 720
gatctgtaa 729

<210> SEQ ID NO 47
<211> LENGTH: 1155
<212> TYPE: DNA
<213> ORGANISM: Artificial Sequence
<220> FEATURE:
<223> OTHER INFORMATION: P. falciparum CSP B cell epitope in tandem WHcAg dimer

<400> SEQUENCE: 47
atggacatag atccctataa agaatttggt tcatcttatc agttgttgaa ttttctacct 60
ttggacttct ttcctgacct aaatgctttg gtggacactg ctactgcctt gtatgaagaa 120
gagctaacag gtcgagaaca ttgctctccg caccatacag ctattagaca agctttagta 180
tgctgggatg aattaactaa attgatagct tggatgagct ctaacataac ttctgaacaa 240
gtaagaacaa tcatagtaaa tcatgtcaat gatacctggg gattaaaggt gagacaaagt 300
ttatggtttc atttgtcatg tttgactttt ggacaacata cagttcaaga atttttagta 360
agttttggag tatggatcag aactccagct ccatatagac ctcctaatgc acccattctc 420
tccactcttc ccgaacatac agtcattggt ggaagtggag ggtctggtgg gtccgggggt 480
agtggtgggt ctgatatcga tccctacaaa gaattcggca gttcttatca gttactaaat 540
ttcctgccgc tggatttttt tcccgatctg aacgccttgg tcgatactgc caccgccttg 600
tacgaggaag agctaaccgg gcgagagcat tgtagtccac atcatactgc tatccgccag 660
gctctggtct gctgggacga attgaccaag ttaattgcat ggatgagctc caatattact 720
agtgaagagg gtaatgcaaa ccctaatgcg aacccgaacg ctaaccctaa tgccaatcct 780
aacgctaatc ccaatgccaa cccgaatgca aacccaaatg cgaatccgaa tgctaacccg 840
aacgctaacc cgaatgcgaa tccaaacgcg aaccccaacg caaatccgaa tgcaaaccct 900
aatgcaaatc caggtgaaga ggagcaggtc cgcacgatca ttgttaacca cgtcaacgat 960
acctggggcc taaaggttcg ccaatctttg tggttccatc tgtcgtgcct gacctttggg 1020
caacacaccg tccaggagtt cctggtgagc ttcggcgttt ggatccgcac cccagcaccc 1080
taccgcccgc caaatgctcc cattttaagt accttgcccg aacacaccgt gattcaccac 1140
catcatcacc actaa 1155

<210> SEQ ID NO 48
<211> LENGTH: 1971
<212> TYPE: DNA
<213> ORGANISM: Artificial Sequence
<220> FEATURE:
<223> OTHER INFORMATION: P. falciparum CSP B cell epitope + Salmonella fliC sequences in tandem WHcAg dimer

<400> SEQUENCE: 48
atggacatag atccctataa agaatttggt tcatcttatc agttgttgaa ttttctacct 60
ttggacttct ttcctgacct aaatgctttg gtggacactg ctactgcctt gtatgaagaa 120
gagctaacag gtcgagaaca ttgctctccg caccatacag ctattagaca agctttagta 180

```
tgctgggatg aattaactaa attgatagct tggatgagct ctaacataac ttctgaacaa    240
gtaagaacaa tcatagtaaa tcatgtcaat gatacctggg gattaaaggt gagacaaagt    300
ttatggtttc atttgtcatg tttgactttt ggacaacata cagttcaaga atttttagta    360
agttttggag tatggatcag aactccagct ccatatagac ctcctaatgc acccattctc    420
tccactcttc ccgaacatac agtcattggt ggaagtggag ggtctggtgg gtccgggggt    480
agtggtgggt ctgatatcga tccctacaaa gaattcggca gttcttatca gttactaaat    540
ttcctgccgc tggatttttt tcccgatctg aacgccttgg tcgatactgc caccgccttg    600
tacgaggaag agctaaccgg gcgagagcat tgtagtccac atcatactgc tatccgccag    660
gctctggtct gctgggacga attgaccaag ttaattgcat ggatgagctc caatattact    720
agtgaagagg gtgcgcaggt cattaacact aattcgctga gtttactaac acagaataat    780
ctaaacaaga gccaatccgc ccttggcacg gcgatcgagc ggctgagttc ggggctgcgt    840
atcaatagtg ccaaagatga cgcggccggc caggcgattg caaatcgttt tacggccaat    900
ataaaggggc ttacacaggc ttctcgtaat gccaacgacg gtatttccat tgcccaaaca    960
acggaaggcg cgctgaatga aatcaataat aatctgcagc gggtccggga gttagcggtg   1020
cagtctgcca actcaacaaa ttctcaatca gatctggatt ctatccaggc agaaataact   1080
cagaggctta atgaaatcga tcgtgtttct ggacaaaccc agtttaatgg tgtcaaggtc   1140
cttgctcagg acaacaccct gaccatccag gtaggcgcga acgatggaga aaccattgat   1200
attgatctga aacagattaa ttctcagact ctaggtcttg acaccttgaa tgtgcagggt   1260
tctaatgcaa accctaatgc gaacccgaac gctaacccta atgccaatcc taacgctaat   1320
cccaatgcca acccgaatgc aaacccaaat gcgaatccga atgctaaccc gaacgctaac   1380
ccgaatgcga atccaaacgc gaaccccaac gcaaatccga atgcaaaccc taatgcaaat   1440
ccaggttcta ccacaaccga gaatcctctg cagaaaatcg atgctgctct cgcgcaagtg   1500
gacactttgc gttcagattt gggagctgtg caaaatcgtt tcaacagcgc gattacaaac   1560
ctgggtaaca ccgtaaacaa tctgactagt gcccggagtc ggattgaaga tagcgattat   1620
gcgaccgaag tgtctaacat gagccgggcc caaatcttgc agcaagccgg cactagtgtt   1680
ctggcgcaag caaatcaggt cccccaaaac gttctcagcc ttctgcgggg tgaagaggag   1740
caggtccgca cgatcattgt taaccacgtc aacgatacct ggggcctaaa ggttcgccaa   1800
tctttgtggt tccatctgtc gtgcctgacc tttgggcaac acaccgtcca ggagttcctg   1860
gtgagcttcg gcgtttggat ccgcacccca gcaccctacc gcccgccaaa tgctcccatt   1920
ttaagtacct tgcccgaaca caccgtgatt caccaccatc atcaccacta a            1971
```

<210> SEQ ID NO 49
<211> LENGTH: 621
<212> TYPE: DNA
<213> ORGANISM: Artificial Sequence
<220> FEATURE:
<223> OTHER INFORMATION: Canine parvovirus 2L21 peptide epitope in 2x configuration; monomer WhcAg

<400> SEQUENCE: 49

```
atggacatag atccctataa agaatttggt tcatcttatc agttgttgaa ttttctacct     60
ttggacttct ttcctgacct aaatgctttg gtggacactg ctactgcctt gtatgaagaa    120
gagctaacag gtcgagaaca ttgctctccg caccatacag ctattagaca agctttagta    180
tgctgggatg aattaactaa attgatagct tggatgagct ctaacataac ttctgaagag    240
```

```
ggttctgacg gtgctgtgca gcccgatggc ggtcaacccg ctgttcgtaa tgaacgtgct    300

actggtggtg gctctagtga tggtgctgtt cagcctgacg gtggtcaacc tgctgtgcgc    360

aacgagcgtg caacaggagg tgaagaggaa caagtaagaa caatcatagt aaatcatgtc    420

aatgatacct ggggattaaa ggtgagacaa agtttatggt ttcatttgtc atgtttgact    480

tttggacaac atacagttca agaattttta gtaagttttg gagtatggat cagaactcca    540

gctccatata gacctcctaa tgcacccatt ctctccactc ttcccgaaca tacagtcatt    600

caccaccatc atcaccacta a                                              621
```

<210> SEQ ID NO 50
<211> LENGTH: 717
<212> TYPE: DNA
<213> ORGANISM: Artificial Sequence
<220> FEATURE:
<223> OTHER INFORMATION: Canine parvovirus 3L17 peptide epitope in 4x configuration; monomer WhcAg

<400> SEQUENCE: 50

```
atggacatag atccctataa agaatttggt tcatcttatc agttgttgaa ttttctacct     60

ttggacttct ttcctgacct aaatgctttg gtggacactg ctactgcctt gtatgaagaa    120

gagctaacag gtcgagaaca ttgctctccg caccatacag ctattagaca agctttagta    180

tgctgggatg aattaactaa attgatagct tggatgagct ctaacataac ttctgaagag    240

ggtgacggtg ctgtgcagcc cgatggcggt caacccgctg ttcgtaatga acgtggtggc    300

tctgatggtg ctgttcagcc tgacggtggt caacctgctg tgcgcaacga gcgtggtggt    360

tccgacggtg ccgttcaacc cgacggtggc caacccgccg tgcgtaatga gcgcggtggt    420

tctgacggcg ctgtgcaacc tgacggcggt cagcccgccg ttcgtaacga gcgtggtgaa    480

gaggaacaag taagaacaat catagtaaat catgtcaatg atacctgggg attaaaggtg    540

agacaaagtt tatggtttca tttgtcatgt ttgacttttg gacaacatac agttcaagaa    600

tttttagtaa gttttggagt atggatcaga actccagctc catatagacc tcctaatgca    660

cccattctct ccactcttcc cgaacataca gtcattcacc accatcatca ccactaa       717
```

<210> SEQ ID NO 51
<211> LENGTH: 1152
<212> TYPE: DNA
<213> ORGANISM: Artificial Sequence
<220> FEATURE:
<223> OTHER INFORMATION: IHNV vaccine; E1+E2 epitopes in tandem WHcAg dimer

<400> SEQUENCE: 51

```
atggacatag atccctataa agaatttggt tcatcttatc agttgttgaa ttttctacct     60

ttggacttct ttcctgacct aaatgctttg gtggacactg ctactgcctt gtatgaagaa    120

gagctaacag gtcgagaaca ttgctctccg caccatacag ctattagaca agctttagta    180

tgctgggatg aattaactaa attgatagct tggatgagct ctaacataac ttctgaacaa    240

gtaagaacaa tcatagtaaa tcatgtcaat gatacctggg gattaaaggt gagacaaagt    300

ttatggtttc atttgtcatg tttgactttt ggacaacata cagttcaaga atttttagta    360

agttttggag tatggatcag aactccagct ccatatagac ctcctaatgc acccattctc    420

tccactcttc ccgaacatac agtcattggt ggaagtggag ggtctggtgg gtccgggggt    480

agtggtgggt ctgatatcga tccctacaaa gaattcggca gttcttatca gttactaaat    540
```

```
ttcctgccgc tggatttttt tcccgatctg aacgccttgg tcgatactgc caccgccttg    600

tacgaggaag agctaaccgg gcgagagcat tgtagtccac atcatactgc tatccgccag    660

gctctggtct gctgggacga attgaccaag ttaattgcat ggatgagctc caatattact    720

agtcctggtg gaagtggaga cgatgaaaat cgtggcttga tcgcttatcc taccagtatc    780

cgttccttga gtgtcggcgg aagtggaggg tctgatctga ttagcgtggt ttacaacagt    840

ggaagcgaga tcctgtcgtt tcctggtgga tcaggggagc aggtccgcac gatcattgtt    900

aaccacgtca acgatacctg ggcctaaag gttcgccaat ctttgtggtt ccatctgtcg    960

tgcctgacct ttgggcaaca caccgtccag gagttcctgg tgagcttcgg cgtttggatc   1020

cgcaccccag caccctaccg cccgccaaat gctcccattt taagtacctt gcccgaacac   1080

accgtgattg agcaaaaatt aattagcgag gaagacctag aacaaaaact gatctctgaa   1140

gaggatctgt aa                                                       1152
```

<210> SEQ ID NO 52
<211> LENGTH: 1356
<212> TYPE: DNA
<213> ORGANISM: Artificial Sequence
<220> FEATURE:
<223> OTHER INFORMATION: IHNV vaccine; DIII epitope in tandem WHcAg dimer

<400> SEQUENCE: 52

```
atggacatag atccctataa agaatttggt tcatcttatc agttgttgaa ttttctacct     60

ttggacttct ttcctgacct aaatgctttg gtggacactg ctactgcctt gtatgaagaa    120

gagctaacag gtcgagaaca ttgctctccg caccatacag ctattagaca agctttagta    180

tgctgggatg aattaactaa attgatagct tggatgagct ctaacataac ttctgaacaa    240

gtaagaacaa tcatagtaaa tcatgtcaat gatacctggg gattaaaggt gagacaaagt    300

ttatggtttc atttgtcatg tttgactttt ggacaacata cagttcaaga atttttagta    360

agttttggag tatggatcag aactccagct ccatatagac ctcctaatgc acccattctc    420

tccactcttc ccgaacatac agtcattggt ggaagtggag ggtctggtgg gtccgggggt    480

agtggtgggt ctgatatcga tccctacaaa gaattcggca gttcttatca gttactaaat    540

ttcctgccgc tggatttttt tcccgatctg aacgccttgg tcgatactgc caccgccttg    600

tacgaggaag agctaaccgg gcgagagcat tgtagtccac atcatactgc tatccgccag    660

gctctggtct gctgggacga attgaccaag ttaattgcat ggatgagctc caatattact    720

agtcctggtg gaagtggaga cgatgagaac agggggctaa ttgcctatcc cacatccatc    780

cggtccctgt cagtcggaaa cgacggtggc agtggagggt ctagccaaga gataaaagct    840

cacctctttg ttgataaaat ctccaatcga gtcgtgaagg caacgagcta cggacaccac    900

ccctggggac tgcatcaggc ctgtatgatt gaattctgtg ggcaacagtg gatacggaca    960

gatctcggtg acctaatatc tgtcgtatac aattctggat cagaaatcct ctcgttcccg   1020

aagtgtgaag acaagaccgt gggaccagca gagggtggcg gtccagcagg tggatcaggg   1080

gagcaggtcc gcacgatcat tgttaaccac gtcaacgata cctggggcct aaaggttcgc   1140

caatctttgt ggttccatct gtcgtgcctg acctttgggc aacacaccgt ccaggagttc   1200

ctggtgagct tcggcgtttg gatccgcacc ccagcaccct accgcccgcc aaatgctccc   1260

attttaagta ccttgcccga acacaccgtg attgagcaaa aattaattag cgaggaagac   1320

ctagaacaaa aactgatctc tgaagaggat ctgtaa                             1356
```

<210> SEQ ID NO 53
<211> LENGTH: 58
<212> TYPE: PRT
<213> ORGANISM: Plasmodium yoelii

<400> SEQUENCE: 53

Gln Gly Pro Gly Ala Pro Gln Gly Pro Gly Ala Pro Gln Gly Pro Gly
1               5                   10                  15

Ala Pro Gln Gly Pro Gly Ala Pro Gln Gly Pro Gly Ala Pro Gln Gly
            20                  25                  30

Pro Gly Ala Pro Gln Glu Pro Pro Gln Gln Pro Pro Gln Gln Pro Pro
        35                  40                  45

Gln Gln Pro Pro Gln Gln Pro Pro Gln Gln
    50                  55

<210> SEQ ID NO 54
<211> LENGTH: 15
<212> TYPE: PRT
<213> ORGANISM: Plasmodium yoelii

<400> SEQUENCE: 54

Asn Glu Asp Ser Tyr Val Pro Ser Ala Glu Gln Ile Leu Glu Phe
1               5                   10                  15

<210> SEQ ID NO 55
<211> LENGTH: 99
<212> TYPE: DNA
<213> ORGANISM: Escherichia coli

<400> SEQUENCE: 55
cgtatgaagc agatagagga caagatcgag gaaatcctgt cgaaaatcta tcacattgaa     60
aatgagattg cacggataaa gaaattgatt ggtgaaaga                            99

<210> SEQ ID NO 56
<211> LENGTH: 99
<212> TYPE: DNA
<213> ORGANISM: Unknown
<220> FEATURE:
<223> OTHER INFORMATION: Arthrospira sp.

<400> SEQUENCE: 56
cgcatgaaac aaattgaaga taaaatcgaa gagattctga gcaagatcta tcacattgaa     60
aacgagattg ctcgtatcaa aaaattgatc ggtgaacgt                            99

<210> SEQ ID NO 57
<211> LENGTH: 33
<212> TYPE: PRT
<213> ORGANISM: Unknown
<220> FEATURE:
<223> OTHER INFORMATION: 1GCM (GCN4-pII coiled-coil trimerization
      domain)

<400> SEQUENCE: 57

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 58
<211> LENGTH: 108

<212> TYPE: DNA
<213> ORGANISM: Escherichia coli

<400> SEQUENCE: 58
cgtttactgc agcggatcaa gcagcaggag gataaactgg aagagacact gtctaagatc 60
taccatctgg agaatgaaat agcaagagtt aaaaaactgg gagagcgc 108

<210> SEQ ID NO 59
<211> LENGTH: 108
<212> TYPE: DNA
<213> ORGANISM: Unknown
<220> FEATURE:
<223> OTHER INFORMATION: Arthrospira sp.

<400> SEQUENCE: 59
cgtttgctgc aacgtattaa gcaacaggaa gataagttgg aggaaactct gagcaagatc 60
taccacttgg aaaacgaaat cgctcgtgtt aaaaaactgg gcgagcgt 108

<210> SEQ ID NO 60
<211> LENGTH: 36
<212> TYPE: PRT
<213> ORGANISM: Unknown
<220> FEATURE:
<223> OTHER INFORMATION: 1ce0 (GCN4-pII coiled-coil trimerization domain with mutations from HIV gp41)

<400> SEQUENCE: 60

Arg Leu Leu Gln Arg Ile Lys Gln Gln Glu Asp Lys Leu Glu Glu Thr
1 5 10 15

Leu Ser Lys Ile Tyr His Leu Glu Asn Glu Ile Ala Arg Val Lys Lys
20 25 30

Leu Gly Glu Arg
35

<210> SEQ ID NO 61
<211> LENGTH: 132
<212> TYPE: DNA
<213> ORGANISM: Escherichia coli

<400> SEQUENCE: 61
gtgtcggggc ttgtacagca acagaacaat atactacgcg cgttagaagc aacccagcat 60
gccgtgcagg ccctggtgtg gggcgtaaag cagcttcagg ccagagtatt agcactggag 120
cggtacatta ag 132

<210> SEQ ID NO 62
<211> LENGTH: 132
<212> TYPE: DNA
<213> ORGANISM: Unknown
<220> FEATURE:
<223> OTHER INFORMATION: Arthrospira sp.

<400> SEQUENCE: 62
gtgtccggct tggtgcaaca acaaaacaac atcctgcgtg ctctggaagc tacccaacac 60
gctgttcaag ccctggtgtg gggtgttaaa caactgcaag ctcgtgtttt ggctttggaa 120
cgctacatta ag 132

<210> SEQ ID NO 63
<211> LENGTH: 49
<212> TYPE: PRT
<213> ORGANISM: Unknown
<220> FEATURE:

<223> OTHER INFORMATION: 2zfc (N-terminal HIV gp41-derived)

<400> SEQUENCE: 63

Gln Ala Arg Gln Leu Val Ser Gly Leu Val Gln Gln Gln Asn Asn Ile
1               5                   10                  15

Leu Arg Ala Leu Glu Ala Thr Gln His Ala Val Gln Ala Leu Val Trp
            20                  25                  30

Gly Val Lys Gln Leu Gln Ala Arg Val Leu Ala Leu Glu Arg Tyr Ile
        35                  40                  45

Lys

<210> SEQ ID NO 64
<211> LENGTH: 102
<212> TYPE: PRT
<213> ORGANISM: Artificial Sequence
<220> FEATURE:
<223> OTHER INFORMATION: IHNV DIII epitope

<400> SEQUENCE: 64

Asp Asp Glu Asn Arg Gly Leu Ile Ala Tyr Pro Thr Ser Ile Arg Ser
1               5                   10                  15

Leu Ser Val Gly Asn Asp Gly Gly Ser Gly Gly Ser Ser Gln Glu Ile
            20                  25                  30

Lys Gly His Leu Phe Val Asp Lys Ile Ser Asn Arg Val Val Lys Ala
        35                  40                  45

Thr Ser Tyr Gly His His Pro Trp Gly Leu His Gln Ala Cys Met Ile
    50                  55                  60

Glu Phe Cys Gly Gln Gln Trp Ile Arg Thr Asp Leu Gly Asp Leu Ile
65                  70                  75                  80

Ser Val Val Tyr Asn Ser Gly Ser Glu Ile Leu Ser Phe Pro Lys Cys
                85                  90                  95

Glu Asp Lys Thr Val Gly
            100

<210> SEQ ID NO 65
<211> LENGTH: 8
<212> TYPE: PRT
<213> ORGANISM: Artificial Sequence
<220> FEATURE:
<223> OTHER INFORMATION: HIV gp41 fusion peptide A epitope

<400> SEQUENCE: 65

Ala Val Gly Ile Gly Ala Val Phe
1               5

<210> SEQ ID NO 66
<211> LENGTH: 8
<212> TYPE: PRT
<213> ORGANISM: Artificial Sequence
<220> FEATURE:
<223> OTHER INFORMATION: HIV gp41 fusion peptide B epitope

<400> SEQUENCE: 66

Ala Val Gly Leu Gly Ala Val Phe
1               5

<210> SEQ ID NO 67
<211> LENGTH: 8
<212> TYPE: PRT
<213> ORGANISM: Artificial Sequence
<220> FEATURE:
<223> OTHER INFORMATION: HIV gp41 fusion peptide C epitope

<400> SEQUENCE: 67

Ala Val Gly Ile Gly Ala Met Ile
1 5

<210> SEQ ID NO 68
<211> LENGTH: 508
<212> TYPE: PRT
<213> ORGANISM: Infectious hematopoietic necrosis virus

<400> SEQUENCE: 68

Met Asp Thr Met Ile Thr Thr Pro Leu Ile Leu Ile Leu Ile Thr Cys
1 5 10 15

Gly Ala Asn Ser Gln Thr Val Lys Pro Asp Thr Ala Ser Glu Ser Asp
20 25 30

Gln Pro Thr Trp Ser Asn Pro Leu Phe Thr Tyr Pro Glu Gly Cys Thr
35 40 45

Leu Asp Lys Leu Ser Lys Val Asn Ala Ser Gln Leu Arg Cys Pro Arg
50 55 60

Ile Phe Asp Asp Glu Asn Arg Gly Leu Ile Ala Tyr Pro Thr Ser Ile
65 70 75 80

Arg Ser Leu Ser Val Gly Asn Asp Leu Gly Glu Ile His Thr Gln Gly
85 90 95

Asn His Ile His Lys Val Leu Tyr Arg Thr Ile Cys Ser Thr Gly Phe
100 105 110

Phe Gly Gly Gln Thr Ile Glu Lys Ala Leu Val Glu Met Lys Leu Ser
115 120 125

Thr Lys Glu Ala Gly Ala Tyr Asp Thr Thr Thr Ala Ala Ala Leu Tyr
130 135 140

Phe Pro Ala Pro Arg Cys Gln Trp Tyr Thr Asp Asn Val Gln Asn Asp
145 150 155 160

Leu Ile Phe Tyr Tyr Thr Thr Gln Lys Ser Val Leu Arg Asp Pro Tyr
165 170 175

Thr Arg Asp Phe Leu Asp Ser Asp Phe Ile Gly Gly Lys Cys Thr Lys
180 185 190

Ser Pro Cys Gln Thr His Trp Ser Asn Val Val Trp Met Gly Asp Ala
195 200 205

Gly Ile Pro Ala Cys Asp Ser Ser Gln Glu Ile Lys Gly His Leu Phe
210 215 220

Val Asp Lys Ile Ser Asn Arg Val Val Lys Ala Thr Ser Tyr Gly His
225 230 235 240

His Pro Trp Gly Leu His Gln Ala Cys Met Ile Glu Phe Cys Gly Gln
245 250 255

Gln Trp Ile Arg Thr Asp Leu Gly Asp Leu Ile Ser Val Val Tyr Asn
260 265 270

Ser Gly Ser Glu Ile Leu Ser Phe Pro Lys Cys Glu Asp Lys Thr Val
275 280 285

Gly Met Arg Gly Asn Leu Asp Asp Phe Ala Tyr Leu Asp Asp Leu Val
290 295 300

Lys Ala Ser Glu Ser Arg Glu Glu Cys Leu Glu Ala His Ala Glu Ile
305 310 315 320

Ile Ser Thr Asn Ser Val Thr Pro Tyr Leu Leu Ser Lys Phe Arg Ser
325 330 335

Pro His Pro Gly Ile Asn Asp Val Tyr Ala Met His Lys Gly Ser Ile
340 345 350

```
Tyr His Gly Met Cys Met Thr Val Ala Val Asp Glu Val Ser Lys Asp
        355                 360                 365

Arg Thr Thr Tyr Arg Ala His Arg Ala Thr Ser Phe Thr Lys Trp Glu
    370                 375                 380

Arg Pro Phe Gly Asp Glu Trp Glu Gly Phe His Gly Leu His Gly Asn
385                 390                 395                 400

Asn Thr Thr Ile Ile Pro Asp Leu Glu Lys Tyr Val Ala Gln Tyr Lys
                405                 410                 415

Met Ser Met Met Glu Pro Met Ser Ile Lys Ser Val Pro His Pro Ser
            420                 425                 430

Ile Leu Ala Leu Tyr Asn Glu Thr Asp Val Ser Gly Ile Ser Ile Arg
        435                 440                 445

Lys Leu Asp Ser Phe Asp Leu Gln Ser Leu His Trp Ser Phe Trp Pro
    450                 455                 460

Thr Ile Ser Ala Leu Gly Gly Ile Pro Phe Val Leu Leu Leu Ala Val
465                 470                 475                 480

Ala Ala Cys Cys Cys Trp Ser Gly Arg Pro Pro Thr Pro Ser Val Pro
                485                 490                 495

Gln Ser Ile Pro Met Tyr His Leu Ala Asn Arg Ser
            500                 505


<210> SEQ ID NO 69
<211> LENGTH: 584
<212> TYPE: PRT
<213> ORGANISM: Canine parvovirus

<400> SEQUENCE: 69

Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
```

```
    210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ala Glu Gly Gly Thr Asn Phe Gly
    290                 295                 300

Tyr Ile Gly Val Gln Gln Asp Lys Arg Arg Gly Val Thr Gln Met Gly
305                 310                 315                 320

Asn Thr Asn Ile Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Ala Ala Asp Gly Asp Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Thr Asn Asp Asn Val Leu Leu Pro
            420                 425                 430

Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Lys Ile Val Tyr Glu Lys Ser
                565                 570                 575

Gln Leu Ala Pro Arg Lys Leu Tyr
            580
```

<210> SEQ ID NO 70
<211> LENGTH: 839
<212> TYPE: PRT
<213> ORGANISM: Human immunodeficiency virus 1

<400> SEQUENCE: 70

-continued

```
Met Arg Val Arg Gly Met Gln Arg Asn Trp Gln His Leu Gly Lys Trp
1               5                   10                  15

Gly Phe Leu Phe Leu Gly Ile Leu Ile Ile Cys Asn Ala Glu Asp Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Gly Tyr Glu Arg Glu Val
    50                  55                  60

His Asn Val Trp Ala Thr His Ala Cys Val Pro Thr Asp Pro Ser Pro
65                  70                  75                  80

Gln Glu Met Val Leu Glu Asn Val Thr Glu Asn Phe Asn Met Trp Lys
                85                  90                  95

Asn Glu Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Asp Thr Asn Arg Thr Gln Asn Asp Asn Met Thr
    130                 135                 140

Glu Glu Arg Gly Val Leu Lys Asn Cys Ser Phe Asn Met Thr Thr Glu
145                 150                 155                 160

Val Lys Asp Lys Arg Leu Lys Val Ser Ala Leu Phe Tyr Arg Leu Asp
                165                 170                 175

Val Val Pro Ile Ser Asn Asn Ser Asn Ser Ser Glu Tyr Arg Leu Ile
            180                 185                 190

Asn Cys Asn Thr Ser Thr Ile Lys Gln Ala Cys Pro Lys Val Ser Trp
        195                 200                 205

Asp Pro Ile Pro Ile His Tyr Cys Ala Pro Ala Gly Tyr Ala Ile Leu
    210                 215                 220

Gln Cys Arg Asp Lys Gln Phe Asn Gly Thr Gly Pro Cys Lys Asn Val
225                 230                 235                 240

Ser Thr Val Gln Cys Thr His Gly Ile Lys Pro Val Val Ser Thr Gln
                245                 250                 255

Leu Leu Leu Asn Gly Ser Leu Ala Glu Lys Asp Ile Ile Ile Arg Cys
            260                 265                 270

Gln Asn Ile Ser Asp Asn Thr Lys Thr Ile Ile Val His Leu Asn Glu
        275                 280                 285

Ser Val Gln Ile Asn Cys Thr Arg Pro Asn Asn Asn Val Val Glu Ser
    290                 295                 300

Ile His Leu Gly Pro Gly Gln Ala Phe Tyr Ala Thr Arg Arg Ile Thr
305                 310                 315                 320

Gly Asn Ile Arg Lys Ala Tyr Cys Asn Ile Asn Gly Thr Gln Trp Asn
                325                 330                 335

Asn Thr Leu Glu Arg Val Lys Thr Lys Leu Lys Thr Tyr Phe Asn Lys
            340                 345                 350

Thr Ile Thr Phe Asn Ser Ala Ser Gly Gly Asp Leu Glu Val Thr Met
        355                 360                 365

His Ser Phe Asn Cys Arg Gly Glu Phe Phe Tyr Cys Asn Thr Ser Glu
    370                 375                 380

Leu Phe Lys Asn Ala Ile Thr Pro Asn Val Thr Ile Ile Leu Gln Cys
385                 390                 395                 400

Arg Ile Lys Gln Ile Ile Asn Met Trp Gln Gly Val Gly Gln Ala Met
                405                 410                 415

Tyr Ala Ser Pro Ile Ala Gly Ser Ile Thr Cys Asn Ser Ser Ile Thr
```

```
            420                 425                 430

Gly Leu Leu Leu Thr Arg Asp Gly Gly Asn Asp Asn Val Ser Thr Glu
        435                 440                 445

Glu Ile Phe Arg Pro Gly Gly Gly Asn Met Lys Asp Asn Trp Arg Ser
    450                 455                 460

Glu Leu Tyr Lys Tyr Lys Val Val Lys Ile Glu Pro Leu Gly Val Ala
465                 470                 475                 480

Pro Thr Arg Ala Lys Arg Gln Val Val Lys Arg Asp Lys Arg Ala Val
                485                 490                 495

Gly Leu Gly Ala Val Phe Leu Gly Phe Leu Gly Ala Ala Gly Ser Thr
            500                 505                 510

Met Gly Ala Ala Ser Ile Thr Leu Met Val Gln Ala Arg Gln Leu Leu
        515                 520                 525

Ser Gly Ile Val Gln Gln Gln Asn Asn Leu Leu Arg Ala Ile Glu Ala
    530                 535                 540

Gln Gln His Met Leu Gln Leu Thr Val Trp Gly Ile Lys Gln Leu Gln
545                 550                 555                 560

Ala Arg Leu Leu Ala Val Glu Arg Tyr Leu Lys Asp Gln Gln Leu Leu
                565                 570                 575

Gly Ile Trp Gly Cys Ser Gly Lys Leu Ile Cys Thr Thr Asn Val Pro
            580                 585                 590

Trp Asn Ser Ser Trp Ser Asn Lys Ser Gln Glu Glu Ile Trp Gly Asn
        595                 600                 605

Met Thr Trp Met Glu Trp Glu Lys Glu Ile Ser Asn Tyr Ser Ser Thr
    610                 615                 620

Ile Tyr Ser Leu Ile Glu Gln Ser Gln Asn Gln Gln Glu Lys Asn Glu
625                 630                 635                 640

Gln Glu Leu Leu Ala Leu Asp Lys Trp Thr Ser Leu Trp Asn Trp Phe
                645                 650                 655

Asp Ile Ser Asn Trp Leu Trp Tyr Ile Lys Ile Phe Ile Met Ile Val
            660                 665                 670

Gly Gly Leu Ile Gly Leu Arg Ile Val Phe Ala Val Leu Ser Ile Val
        675                 680                 685

Asn Arg Val Arg Lys Gly Tyr Ser Pro Leu Ser Leu Gln Thr Leu Ile
    690                 695                 700

Pro Ser Pro Arg Gly Pro Asp Arg Pro Glu Gly Ile Glu Glu Gly Gly
705                 710                 715                 720

Gly Glu Gln Asn Arg Asp Arg Ser Val Arg Leu Val Asn Gly Phe Leu
                725                 730                 735

Ala Leu Val Trp Asp Asp Leu Arg Asn Leu Cys Leu Phe Ser Tyr Arg
            740                 745                 750

His Leu Arg Asp Phe Ile Leu Ile Ala Ala Arg Thr Val Asp Arg Gly
        755                 760                 765

Leu Arg Arg Gly Trp Glu Ala Leu Lys Tyr Leu Trp Asn Leu Ile Gln
    770                 775                 780

Tyr Trp Ser Arg Glu Leu Lys Asn Ser Thr Thr Ser Leu Leu Asp Thr
785                 790                 795                 800
```

-continued

```
Thr Ala Val Val Val Ala Glu Gly Thr Asp Arg Val Ile Glu Ala Leu
            805                 810                 815

Gln Arg Ala Gly Arg Ala Val Leu Asn Val Pro Arg Arg Ile Arg Gln
        820                 825                 830

Gly Ala Glu Arg Ala Leu Leu
        835
```

ARTHROSPIRA PLATENSIS ORAL VACCINE DELIVERY PLATFORM

CROSS REFERENCE TO RELATED APPLICATIONS

This Application is a U.S. National Phase of PCT/US2019/032998, filed May 17, 2019, which claims the benefit of priority to U.S. Provisional Application No. 62/672,891, filed on May 17, 2018, the contents of each of which are hereby incorporated by reference in their entirety

INCORPORATION BY REFERENCE OF THE SEQUENCE LISTING

The contents of the text file submitted electronically herewith are incorporated herein by reference in their entirety. A computer readable format copy of the Sequence Listing (filename: LUBI_024_01WO_SeqList_ST25.txt, date recorded: May 17, 2019, file size≈124,316 bytes).

FIELD

The disclosure is directed to oral antigenic compositions. In particular, the disclosure provides oral antigenic compositions comprising recombinant *Spirulina*, wherein the recombinant *Spirulina* comprises one or more exogenous antigenic epitopes.

BACKGROUND

Vaccination is an efficient and cost-effective form of inducing immunity in an individual and a population, thereby saving lives and reducing morbidity and/or disability for billions of people. Despite the early success of the oral polio vaccine, most vaccines are delivered parenterally, and as such are associated with pain, non-compliance, biohazardous medical waste and strict requirements for expensive production, transport and storage logistics (the "cold chain") and for trained technical personnel. Oral/mucosal vaccines eliminate or significantly reduce these drawbacks. Oral vaccines have been attempted in numerous plant species as well as eukaryotic algae, various yeasts and some bacteria. These platforms have suffered from technical and logistical challenges, including but not limited to poor vaccine protein expression, inherent toxicity, unpalatability, poor IgG induction or expensive extraction/purification procedures. Thus, there is an unmet need to provide a delivery platform for the large-scale and cost-effective production of oral vaccines. The present disclosure provides a new oral vaccine platform that eliminates or reduces some of these drawbacks and serves as both, a production as well as a delivery platform, for oral vaccines. Specifically, the present disclosure provides *Arthrospira platensis*, commonly known as *Spirulina*, engineered to express high amounts of target antigens in a form that can be ingested orally without purification.

SUMMARY OF THE INVENTION

Provided herein are oral antigenic compositions comprising a recombinant *Spirulina*, wherein the recombinant *Spirulina* comprises at least one exogenous antigenic epitope. In some embodiments, the at least one exogenous antigenic epitope is comprised in an exogenous antigen expressed by *Spirulina*.

In some embodiments, the exogenous antigen is a naturally-occurring antigen. For example, a recombinant *Spirulina* may express one or more exogenous antigens such as circumsporozoite proteins or TRAP proteins from *Plasmodium* that contain one or more antigenic epitopes.

In some embodiments, the exogenous antigen is a fusion protein. In some embodiments, the fusion protein comprises a viral protein. In some embodiments, the viral protein is a virus-like particle (VLP)-forming protein.

In some embodiments, the fusion protein comprises a scaffold protein.

In some embodiments, at least 2, at least 3, at least 4, or at least 5 copies of a nucleic acid sequence encoding the at least one exogenous antigenic epitope are present in the recombinant *Spirulina.*

In some embodiments, 2, 3, 4, 5, 6, 8, 10, 15, 20, 25, 30, 40, or 50 copies of a nucleic acid sequence encoding the at least one exogenous antigenic epitope are present in the recombinant *Spirulina.*

In some embodiments, at least 2, at least 3, at least 4, or at least 5 copies of the at least one exogenous antigenic epitope are present in a single molecule of the exogenous antigen expressed in the recombinant *Spirulina.*

In some embodiments, 2, 3, 4, 5, 6, 8, 10, 15, 20, 25, 30, 40, or 50 copies of the at least one exogenous antigenic epitope are present in a single molecule of the exogenous antigen expressed in the recombinant *Spirulina.*

In some embodiments, within the molecule of the exogenous antigen, the copies of the exogenous antigenic epitope are linked in tandem.

In some embodiments, within the molecule of the exogenous antigen, the copies of the exogenous antigenic epitope are separated by a spacer sequence.

In some embodiments, within the molecule of exogenous antigen, some of the copies of the exogenous antigenic epitope are linked in tandem and the remaining copies of the exogenous antigenic epitope are separated by a spacer sequence.

In some embodiments, the spacer sequence is between about 1 and 50 amino acids long. In some embodiments, more than one spacer sequence is present within the molecule of the exogenous antigen.

In some embodiments, the recombinant *Spirulina* comprises at least 2, at least 3, at least 4, or at least 5 different antigenic epitopes.

In some embodiments, the at least one exogenous antigenic epitope present in a recombinant *Spirulina* is derived from an infectious microorganism, a tumor antigen or a self-antigen associated with an autoimmune disease.

In some embodiments, the infectious microorganism is a virus, bacterium, parasite, or fungus.

In some embodiments, the infectious microorganism is a bacterium selected from the group consisting of: *Mycobacterium, Streptococcus, Staphylococcus, Shigella, Campylobacter, Salmonella, Clostridium, Corynebacterium, Pseudomonas, Neisseria, Listeria, Vibrio, Bordetella, Helicobacter pylori*, and *Legionella.*

In some embodiments, the infectious microorganism is a virus selected from the group consisting of: bacteriophage, RNA bacteriophage (e.g. MS2, AP205, PP7 and Qβ), Infectious Haematopoietic Necrosis Virus, Parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, and White Spot Syndrome Virus.

In some embodiments, the infectious microorganism is a parasite selected from the group consisting of: *Plasmodium, Trypanosoma, Toxoplasma, Giardia, Leishmania Cryptosporidium*, helminthic parasites: *Trichuris* spp., *Enterobius* spp., *Ascaris* spp., *Ancylostoma* spp. and *Necator* spp., *Strongyloides* spp., *Dracunculus* spp., *Onchocerca* spp. and *Wuchereria* spp., *Taenia* spp., *Echinococcus* spp., and *Diphyllobothrium* spp., *Fasciola* spp., and *Schistosoma* spp.

In some embodiments, the infectious microorganism is a fungus selected from the group consisting of: *Aspergillus, Candida, Blastomyces, Coccidioides, Cryptococcus*, and *Histoplasma.*

In some embodiments, the infectious microorganism is a *Plasmodium*. In some embodiments, the *Plasmodium* is *P. falciparum, P. malariae, P. ovale* or *P. vivax*. In some embodiments, the *Plasmodium* is *Plasmodium falciparum.*

In some embodiments, the at least one exogenous antigenic epitope is from a *Plasmodium* antigen selected from the group consisting of: circumsporozoite protein, thrombospondin-related anonymous protein (TRAP), Apical Membrane Antigen 1 (AMA1), the major merozoite surface proteins 1-3 (MSP1-3), sexual stage antigen 25 (s25), and sexual stage antigen s230.

In some embodiments, the at least one exogenous antigenic epitope is from a circumsporozoite protein of a *Plasmodium.*

In some embodiments, the at least one exogenous antigenic epitope comprises the sequence of NANP.

In some embodiments, the recombinant *Spirulina* comprises at least 2 exogenous antigenic epitopes, wherein one of the exogenous antigenic epitope comprises the sequence of NANP and the second exogenous antigenic epitope comprises the sequence of NVDP.

In some embodiments, the recombinant *Spirulina* comprises at least 3 exogenous antigenic epitopes, wherein one of the exogenous antigenic epitope comprises the sequence of NANP, the second exogenous antigenic epitope comprises the sequence of NVDP, and the third exogenous antigenic epitope comprises the sequence of NPDP.

In some embodiments, the at least one exogenous antigenic epitope is from a glycoprotein (SEQ ID NO: 68) of IHNV.

In some embodiments, the at least one exogenous antigenic epitope is from a viral capsid protein of canine parvovirus. In some embodiments, the at least one exogenous antigenic epitope is from a viral capsid protein of canine parvovirus having SEQ ID NO: 69.

In some embodiments, the at least one exogenous antigenic epitope is from the gp41 subunit of an envelope glycoprotein of HIV. In some embodiments, the at least one exogenous antigenic epitope is from the gp41 subunit of an envelope glycoprotein of HIV having SEQ ID NO: 70.

In some embodiments, the at least one exogenous antigenic epitope is comprised in a fusion protein comprising an amino acid sequence derived from a capsid protein of a virus.

In some embodiments, the capsid protein is Hepadnaviridae core antigen (HBcAg).

In some embodiments, the capsid protein is woodchuck hepadnaviridae core antigen (WHcAg).

In some embodiments, the fusion protein comprises an amino acid sequence derived from WHcAg and an at least one exogenous antigenic epitope from the circumsporozoite protein of *Plasmodium*. In some embodiments, the at least one exogenous antigenic epitope from the circumsporozoite (CSP) protein of *Plasmodium* is from the CSP sequence listed in Table 3.

In some embodiments, the fusion protein comprises an amino acid sequence derived from WHcAg and an at least one exogenous antigenic epitope from a glycoprotein of IHNV having SEQ ID NO: 68.

In some embodiments, the fusion protein comprises an amino acid sequence derived from WHcAg and an at least one exogenous antigenic epitope from a viral capsid protein of canine parvovirus. In some embodiments, the at least one exogenous antigenic epitope is from a viral capsid protein of canine parvovirus having SEQ ID NO: 69.

In some embodiments, the fusion protein comprises an amino acid sequence derived from WHcAg and an at least one exogenous antigenic epitope from the gp41 subunit of an envelope glycoprotein of HIV. In some embodiments, the at least one exogenous antigenic epitope is from the gp41 subunit of an envelope glycoprotein of HIV having SEQ ID NO: 70.

In some embodiments, the fusion protein comprises an amino acid sequence derived from WHcAg and the at least one exogenous antigenic epitope selected from the group consisting of: NANP, NVDP, NPDP, and a combination thereof.

In some embodiments, the fusion protein comprises an amino acid sequence derived from WHcAg and an at least one exogenous antigenic epitope selected from Table 1.

In some embodiments, the at least one exogenous antigenic epitope is comprised in a fusion protein comprising a scaffold protein.

In some embodiments, the at least one exogenous antigenic epitope is linked to a scaffold protein at the N-terminus or the C-terminus, or in the body of the scaffold protein.

In some embodiments, the scaffold protein is selected from the oligomerization domain of C4b-binding protein (C4BP), cholera toxin b subunit, or oligomerization domains of extracellular matrix proteins.

In some embodiments, in a fusion protein comprising the at least one exogenous antigenic epitope and the scaffold protein, the at least one exogenous antigenic epitope and the scaffold protein are separated by about 1 to about 50 amino acids.

In some embodiments, at least 2, at least 3, at least 4, or at least 5 copies of the at least one exogenous antigenic epitope are present in a fusion protein expressed by recombinant *Spirulina.*

In some embodiments, the fusion protein comprises 2-1000 copies of the at least one exogenous antigenic epitope.

In some embodiments, the copies of the at least one exogenous antigenic epitope present in a fusion protein are linked in tandem and/or separated by a spacer sequence of between about 1 to about 50 amino acids.

In some embodiments, in a fusion protein comprising the at least one exogenous antigenic epitope and the scaffold protein, the fusion protein comprises multiple copies of the at least one exogenous antigenic epitope, wherein the at least one exogenous antigenic epitope and the scaffold protein are arranged in any one of the following patterns: (E)n-(SP), (SP)-(E)n, (SP)-(E)n-(SP), (E)$n_1$-(SP)-(E)$n_2$, (SP)-(E)$n_1$-(SP)-(E)$n_2$, and (SP)-(E)$n_1$-(SP)-(E)$n_2$-(SP), wherein E is the at least one exogenous antigenic epitope, SP is the scaffold protein, n, $n_1$, and $n_2$ represent the number of copies of the at least one exogenous antigenic epitope.

In some embodiments, the recombinant *Spirulina* comprises a fusion protein comprising one or more antigenic epitopes selected from Table 1.

In some embodiments, the recombinant *Spirulina* comprises a fusion protein comprising a sequence selected from Table 2.

In some embodiments, the recombinant *Spirulina* comprises a fusion protein comprising one or more antigenic epitopes from the sequences listed in Table 3.

In some embodiments, the recombinant *Spirulina* is non-living.

In some embodiments, the recombinant *Spirulina* is dried, spray dried, freeze-dried, or lyophilized.

In some embodiments, the oral antigenic composition comprises a pharmaceutically acceptable excipient.

In some embodiments, provided herein are methods of inducing an immune response in a subject in need thereof, comprising administering to the subject an oral antigenic composition described herein.

In some embodiments, methods of the disclosure induce a humoral immune response.

In some embodiments, methods of the disclosure induce a cellular immune response.

In some embodiments, methods of the disclosure induce an innate immune response.

In some embodiments, provided herein are methods of reducing the severity of an infection in a subject in need thereof, comprising administering to the subject an oral antigenic composition described herein, wherein the composition comprises at least one exogenous antigenic epitope derived from a microorganism causing the infection.

In some embodiments, methods of the disclosure reduce the severity of a viral, bacterial, parasitic, or fungal infection in a subject in need thereof.

In some embodiments, methods of the disclosure reduce the severity of malaria in a subject in need thereof.

In some embodiments, methods of the disclosure reduce the severity of an infection selected from tetanus, diphtheria, pertussis, pneumonia, meningitis, campylobacteriosis, mumps, measles, rubella, polio, flu, hepatitis, chickenpox, malaria, toxoplasmosis, giardiasis, or leishmaniasis.

In some embodiments, methods of the disclosure reduce the severity of an infection caused by a bacterium selected from the group consisting of: *Mycobacterium, Streptococcus, Staphylococcus, Shigella, Campylobacter, Salmonella, Clostridium, Corynebacterium, Pseudomonas, Neisseria, Listeria, Vibrio, Bordetella, Helicobacter pylori*, and *Legionella*.

In some embodiments, methods of the disclosure reduce the severity of an infection caused by a virus selected from the group consisting of: bacteriophage, RNA bacteriophage (e.g. MS2, AP205, PP7 and Qβ), Infectious Haematopoietic Necrosis Virus, Parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, and Poliovirus, Norovirus, Zika virus, Denge Virus, Rabies Virus, Newcastle Disease Virus, and White Spot Syndrome Virus.

In some embodiments, methods of the disclosure reduce the severity of an infection caused by a parasite selected from the group consisting of: *Plasmodium, Trypanosoma, Toxoplasma, Giardia, Leishmania, Cryptosporidium*, helminthic parasites: *Trichuris* spp., *Enterobius* spp., *Ascaris* spp., *Ancylostoma* spp. and *Necator* spp., *Strongyloides* spp., *Dracunculus* spp. *Onchocerca* spp. and *Wuchereria* spp., *Taenia* spp., *Echinococcus* spp., and *Diphyllobothrium* spp., *Fasciola* spp., and *Schistosoma* spp.

In some embodiments, methods of reducing the severity of an infection in a subject in need thereof comprise administering a priming dose of an oral antigenic composition described herein and subsequently administering one or more booster doses of the oral antigenic composition.

In some embodiments, methods of reducing the severity of an infection in a subject in need thereof comprise administering a priming dose of an antigenic composition that is different from the oral antigenic composition and subsequently administering one or more booster doses of the oral antigenic composition.

In some embodiments, the booster dose is administered about two weeks, 1 month, 2 months, 3 months, 4 months, 6 months, 1 year, 2 years, and/or 5 years after the priming dose.

In some embodiments, provided herein are methods of making the oral antigenic composition described herein, the method comprising introducing a nucleic acid sequence encoding the at least one exogenous antigenic epitope into a *Spirulina*.

In some embodiments, provided herein are oral antigenic compositions comprising a recombinant *Spirulina*, wherein the recombinant *Spirulina* comprises at least one exogenous antigenic epitope, wherein a nucleic acid sequence encoding the at least one exogenous antigenic epitope is integrated into the *Spirulina* via homologous recombination.

In some embodiments, provided herein are oral antigenic compositions prepared by a method comprising: introducing a nucleic acid sequence encoding at least one exogenous antigenic epitope into a *Spirulina* and integrating the nucleic acid sequence into the *Spirulina* via homologous recombination.

BRIEF DESCRIPTION OF THE DRAWINGS

FIG. 14 shows a ribbon diagram of GCN4-pII coiled-coil trimerization domain.

FIG. 15 shows a ribbon diagram of GCN4-pII coiled-coil trimerization domain with mutations from HIV gp41.

FIG. 16 shows a ribbon diagram of N-terminal of HIV gp41-derived.

DETAILED DESCRIPTION

Figure 1A:
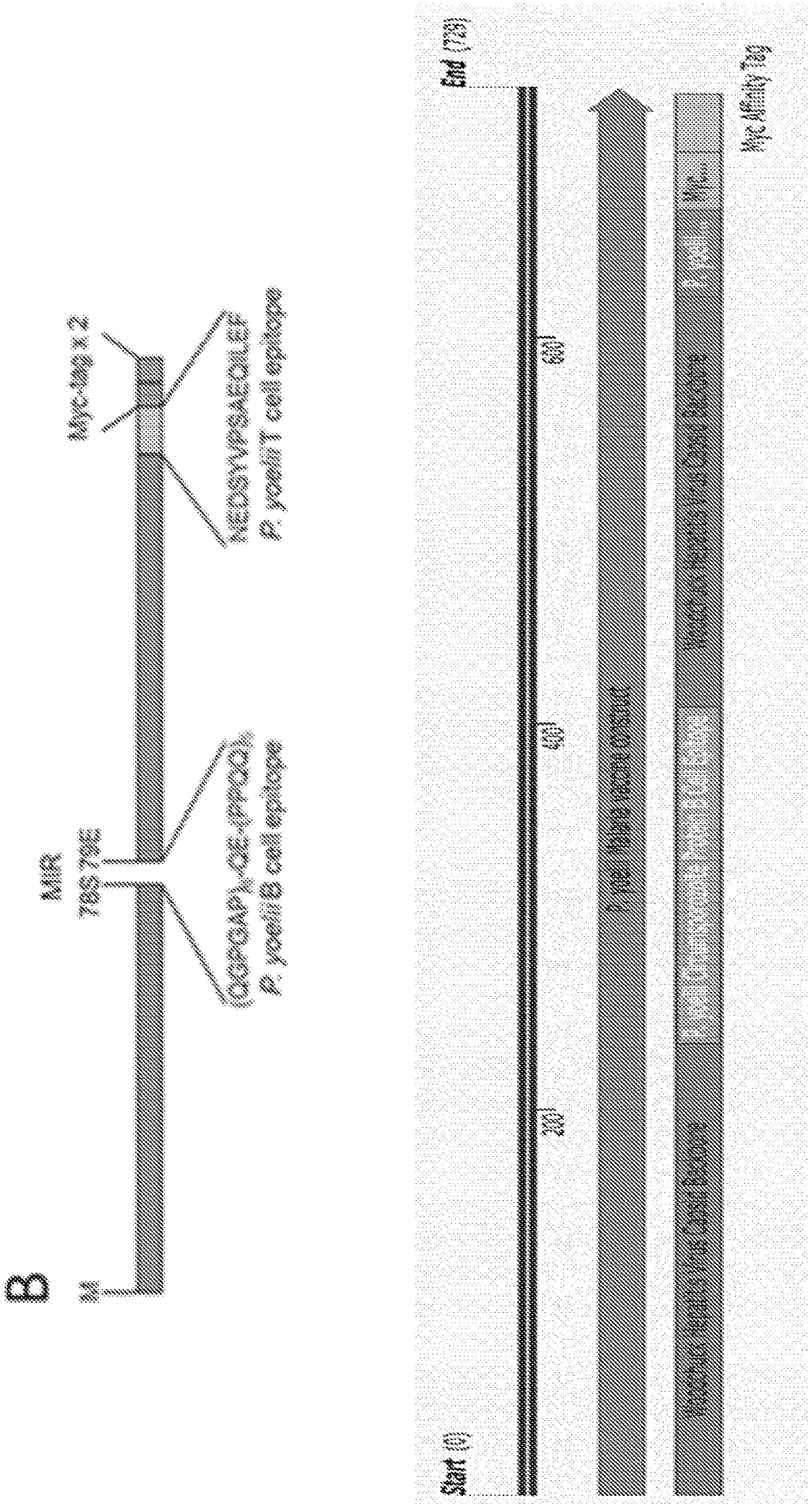
FIG. 1A shows a schematic of the fusion protein described in Example 1 comprising Woodchuck Hepatitis Virus Capsid protein (WHcAg) and *Plasmodium yoelii* circumsporozoite (CSP) protein B cell epitopes and CSP T cell epitopes.

Oral vaccines are safe, easy to administer and convenient for all ages. Various recombinant or attenuated viral or bacterial strains have been developed as carriers for oral delivery of vaccines. For example, both *Salmonella typhimurium* and *Salmonella enterica* have been engineered to express *Plasmodium* antigens or antigenic epitopes for oral vaccination (Schorr, J., et al., Surface expression of malarial antigens in *Salmonella typhimurium*: induction of serum antibody response upon oral vaccination of mice. Vaccine, 1991. 9(9): p. 675-81; Ruiz-Perez, F., et al., Expression of the *Plasmodium falciparum* immunodominant epitope (NANP)(4) on the surface of *Salmonella enterica* using the autotransporter MisL. Infect Immun, 2002. 70(7): p. 3611-20). While these studies induced protective antibodies and some T cell responses, they also required either extensive protein purification or use of live-attenuated organisms.

Another known vaccination strategy comprises the use of virus-like particles (VLPs), where antigenic targets are fused with VLPs. VLPs are non-infectious, robust and highly immunogenic nanoparticles that spontaneously form when viral capsid proteins are expressed in heterologous systems. Oral VLP delivery to healthy volunteers has been shown to be safe and effective. VLPs fused to malaria antigens have been expressed in plants (Jones, R. M., et al., A plant-produced Pfs25 VLP malaria vaccine candidate induces persistent transmission blocking antibodies against *Plasmodium falciparum* in immunized mice. PLoS One, 2013. 8(11): p. e79538). However, as with the *Salmonella*-based vaccines, these systems also require purification of the VLPs or use of live vectors for antigen delivery.

*Chlamydomonas reinhardtii* has been used to express blood-stage malarial proteins. When purified and admixed with recombinant heat labile toxin (LTB; homologous to cholera toxin B (CTB) in structure and function) and fed to mice, protective antibody responses were observed (Dauvillee, D., et al., Engineering the chloroplast targeted malarial vaccine antigens in *Chlamydomonas* starch granules. PLoS One, 2010. 5(12): p. e15424). In a different study, a Pfs25-CTB fusion was similarly expressed in *C. reinhardtii* and shown to be protective when purified and injected intraperitoneally (i.p.) (Gregory, J. A., et al., Algae-produced Pfs25 elicits antibodies that inhibit malaria transmission. PLoS One, 2012. 7(5): p. e37179). However when tested orally, non-purified *Chlamydomonas*/CTB-Pfs25 biomass induced Pfs25-specific non-protective IgA only, but not systemic IgG (Gregory, J. A., et al., Alga-produced cholera toxin-Pfs25 fusion proteins as oral vaccines. Appl Environ Microbiol, 2013. 79(13): p. 3917-25). In this study, whole recombinant biomass was tested orally; however, a protective immune response to the Pfs25 target antigen was not observed. The low expression (0.09% of total soluble protein) and/or degradation in the stomach were invoked as possible explanations for failure of whole recombinant biomass as a vaccine.

The present disclosure is the first in which *Plasmodium* antigens are expressed in edible prokaryotic algae and then administered to a subject, and where administration of the algae induces protective serum anti-parasite IgG antibodies. Furthermore, the expression levels of the exogenous antigens or the antigenic epitopes in the *Spirulina* delivery systems of the present disclosure are 10 to 100-fold higher compared to other systems.

Provided herein are oral antigenic compositions comprising a recombinant *Spirulina* comprising at least one exogenous antigenic epitope, methods of making, and use thereof.

Before describing certain embodiments in detail, it is to be understood that this disclosure is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this disclosure and in the specific context where each term is used. Certain terms are discussed below or elsewhere in the specification, to provide additional guidance to the practitioner in describing the compositions and methods of the disclosure and how to make and use them. The scope and meaning of any use of a term will be apparent from the specific context in which the term is used. As such, the definitions set forth herein are intended to provide illustrative guidance in ascertaining particular embodiments of the disclosure, without limitation to particular compositions or biological systems.

Following long-standing patent law convention, the terms “a”, “an”, and “the” refer to “one or more” when used in this application, including the claims, unless clearly indicated otherwise. By way of example, “an antigenic epitope” means one epitope or more than one epitope.

As use herein, the term “antigenic composition” refers to a preparation which, when administered to a subject will induce a protective immune response that provides immunity to a disease or disorder, or can be used to treat a disease or disorder as described herein.

The term “antigen” as used herein refers to a protein or a peptide that binds to a receptor of an immune cell and induces an immune response in a human or an animal. The antigen can be from infectious microorganisms including viruses, bacteria, parasite, or fungi or the antigen can be a tumor antigen or a self-antigen associated with an autoimmune disease.

The term “antigenic epitope” as used herein refers to a short amino acid sequence, for example, of about 4 to 1000 amino acids, of an antigen that is recognized by, and binds to, a receptor of an immune cell and induces an immune response in a human or an animal. The antigenic epitopes of the present disclosure are from the antigens described above.

The term “subject” as used herein refers to a vertebrate or an invertebrate, and includes mammals, birds, fish, reptiles, and amphibians. Subjects include humans and other primates, including non-human primates such as chimpanzees and other apes and monkey species. Subjects include farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like; and aquatic animals such as fish, shrimp, and crustaceans.

Oral Antigenic Compositions

Provided herein are oral antigenic compositions comprising a recombinant *Spirulina*, wherein the *Spirulina* is engineered to express at least one exogenous antigenic epitope.

In some embodiments, the at least one exogenous antigenic epitope is expressed in *Spirulina* by itself, i.e., the antigenic epitope is not fused to another protein.

In some embodiments, the at least one exogenous antigenic epitope expressed in *Spirulina* is comprised in an exogenous antigen. In some embodiments, the exogenous antigen is a natural antigen. For example, a recombinant *Spirulina* may express the entire circumsporozoite protein containing one or more antigenic epitopes or a portion or a domain of the circumsporozoite protein that contains one or more antigenic epitopes. In this case, the exogenous antigen is considered a natural antigen. Other examples of natural antigens that can be expressed in *Spirulina* to prepare oral antigenic compositions include hemagglutinin (HA), neuraminidase (NA), and matrix (M1) proteins of an influenza virus.

In addition to immunogenic epitopes, the present disclosure provides structures and/or ligands to stimulate the innate immune system (e.g. by engineering the epitopes into VLP structures). The innate immune system can be activated by adjuvant-like properties inherent in the VLP and/or adjuvants added to vaccine compositions. In some embodiments, these structures and/or ligands that stimulate the innate immune system include, but are not limited to, fragments of *Salmonella* flagellin, fliC, human and mouse TNF-alpha, and human and mouse CD40-Ligand.

In some embodiments, the exogenous antigen is a fusion protein. For example, in some embodiments, a recombinant *Spirulina* may express a fusion protein comprising at least one exogenous antigenic epitope and a portion of another protein such as a viral protein or a scaffold protein.

In some embodiments, at least one exogenous epitope is expressed in *Spirulina* as a fusion protein, wherein the fusion protein forms a three-dimensional structure (sometimes referred to herein as “particles”) that presents the at least one antigenic epitope in a spatially recognizable form that can elicit an innate and adaptive immune response. In some embodiments, the fusion protein that forms a three-dimensional structure may comprise multiple functional domains and one or more exogenous antigenic epitopes. Such fusion proteins can be engineered in a number of ways. In some embodiments, a fusion protein is a single polypeptide with multiple modular domains. An example of this is the woodchuck hepadnavirus core antigen (WHcAg) engineered with a B cell antigen at the Major Insertion Region/spike position, and a T cell epitope at the C-terminus. Another example is an RNA bacteriophage (ie, MS2, PP7, AP205 or $Q_\beta$), engineered to be a tandem dimer, with an antigen at the N-terminus, and a fragment of *Salmonella* flagellin at the C-terminus, thus combining an immunogenic epitope with an innate immune system stimulant to act as an intrinsic adjuvant, which self-organizes into a three-dimensional structure with two functional domains displayed on its surface. In some embodiments, recombinant *Spirulina* may express two heterologous polypeptides. For example, a recombinant *Spirulina* may express one gene that encodes a tandem RNA bacteriophage capsid protein dimer with an N-terminal antigenic structure, and a second gene that encodes an identical capsid dimer but with an adjuvant like *Salmonella* flagellin at its C-terminus. These two nearly identical polypeptides expressed in *Spirulina* can cooperatively form a three-dimensional mosaic particle in which the two polypeptides contribute to the “tiling” that forms a VLP capsid. Another example of this is to express a gene encoding a viral capsid protein like WHcAg or one of the RNA phage particles with an antigen genetically linked, and a second gene with the native viral protein. This allows for the avoidance of stearic conflicts that might arise if every particle had a bulky hybrid partner attached. The particles formed in this example can self-organize forming further higher-order structures.

In some embodiments, the recombinant *Spirulina* comprises a fusion protein comprising at least one exogenous antigenic epitope and a trimerization domain of certain proteins that naturally exist as trimers. Exemplary proteins that comprise trimerization domains are described below. For example, the HA protein from influenza virus (either the whole ectodomain or the minimal stem region) naturally forms trimers, and interfaces between monomeric subunits are considered to be important immunodominant epitopes.

The fusion protein (F protein) from respiratory syncytial virus (RSV) is an obligate trimer. Similarly, Tumor Necrosis Factor alpha (TNFα) and the ligand for CD40 (CD40L) are obligate trimers. A recombinant *Spirulina* comprising a fusion protein comprising at least one exogenous antigenic epitope and a trimerization domain of any of these proteins is encompassed by the present disclosure. In exemplary embodiments, to facilitate trimerization, the inventors have genetically linked the WHcAg monomer to a number of coiled-coil domains that both facilitate trimer formation and situate bulky domains like influenza HA away from the potential stearic interference by the spike domains of the WHcAg. The inventors have used a trimerization derivative of the *Saccharomyces cerevisiae* transcription factor GCN4, a parallel trimeric-coiled coil, and a related structure based on CGN4 with the addition of mutations informed by the HIV GP41 trimer structure. The inventors have genetically linked these two trimers, with varying length linker sequences, to WHcAg, as well as to a number of RNA bacteriophages.

In an exemplary embodiment, as illustrated in FIGS. 11-17, the inventors have examined the geometry of the WHcAg VLP particle, and engineered the above-noted coiled coil structures to fit in the "canyon" between the spikes of the native WHcAg particle.

In some embodiments, the recombinant *Spirulina* comprises a fusion protein comprising at least one exogenous antigenic epitope and a viral protein capable of forming a virus-like particle (VLP). In these embodiments, the exogenous antigenic epitope is expressed in *Spirulina* as a protein macromolecular particle, such as virus-like particles (VLPs). VLPs mimic the overall structure of a virus particle by retaining the three-dimensional structure of a virus without containing infectious material. VLPs have the ability to stimulate B-cell and T-cell mediated responses. When viral proteins are expressed in a heterologous system, such as *Spirulina*, they can spontaneously form VLPs. Accordingly, in some embodiments, the at least one exogenous antigenic epitope is fused to a VLP-forming viral protein. When this fusion protein is expressed in *Spirulina*, it forms a VLP.

In some embodiments, tethering the exogenous antigenic epitope to a VLP-forming viral protein (or other protein that forms tertiary structures) allows the expression of hundreds of monomer proteins per VLP (e.g. 180-240 monomer proteins per VLP when using the hepatitis VLP). This allows the expression of thousands of millions of VLPs per cell. In some embodiments, the exogenous antigenic epitope is tethered to a VLP-forming viral protein. In some embodiments, the exogenous antigenic epitope is tethered to a VLP-forming viral protein at the C-terminus or the N-terminus of the viral protein. That is, the amino acid sequence for the antigen or the antigenic epitope is preceded by (attachment of the viral protein at the N-terminus of the antigen or the epitope), or followed by (attachment of the viral protein at the N-terminus of the antigen or the epitope), the amino acid sequence of the viral protein. In some other embodiments, the exogenous antigenic epitope is inserted into a VLP-forming viral protein. For example, the at least one exogenous antigenic epitope can be inserted between two adjacent amino acid residues of the viral protein. Alternatively, a region of the viral protein that is not required for the formation of a VLP can be replaced by inserting the at least one exogenous antigenic epitope in that region. Throughout this disclosure, when it is said that the at least one exogenous antigenic epitope is comprised in a VLP or is present in a VLP, it refers to the fusion protein comprising at least one exogenous antigenic epitope and a VLP-forming viral protein described herein.

Viral proteins that can be used to form antigenic epitope-containing VLPs of the present disclosure include capsid proteins of various viruses. Exemplary capsid proteins that can be used in the VLPs of the present disclosure include capsid proteins of viruses from the Hepadnaviridae family, papillomaviruses, picornaviruses, caliciviruses, rotaviruses, and reoviruses. In some embodiments, viral proteins that can be used to form antigen- or antigenic epitope-expressing VLPs of the present disclosure include the Hepadnaviridae core antigen (HBcAg). An exemplary HBcAg that can be used in the present disclosure is Woodchuck Hepadnaviral core antigen (WHcAg) from the Woodchuck Hepadnavirus (also referred to herein as Woodchuck Hepatitis Virus).

In some embodiments, the recombinant *Spirulina* comprises a fusion protein comprising at least one exogenous antigenic epitope and a protein that forms a trimer. In some embodiments, the trimer-forming protein is from an RNA bacteriophage or *Helicobacter pylori*. In some embodiments, the trimer-forming protein is the *Helicobacter pylori* ferritin protein. The at least one exogenous antigenic epitope can be attached at the C-terminus or the N-terminus, or within the body of the protein that forms a trimer. In some embodiments, these proteins that form a trimer include but are not limited to, GCN4 polypeptides from *S. cerevisiae* and/or HIV or fragments, mutants or variants thereof.

In some embodiments, the recombinant *Spirulina* comprises a fusion protein comprising at least one exogenous antigenic epitope and a scaffold protein. The term "scaffold protein" as used herein refers to a protein that acts as a docking protein and facilitates the interaction between two or more proteins. For example, a fusion protein comprising at least one exogenous antigenic epitope and a scaffold protein can facilitate the binding of the exogenous antigenic epitope with a receptor on an immune cell. In some embodiments, the exogenous antigenic epitope is tethered to a scaffold protein at the C-terminus or the N-terminus of the scaffold protein. In some other embodiments, the exogenous antigenic epitope is inserted into a scaffold protein (e.g. in the body of the scaffold protein). For example, the at least one exogenous antigenic epitope can be inserted between two adjacent amino acid residues of the scaffold protein. Alternatively, a region of the scaffold protein that is not required for the scaffolding function can be replaced by inserting the at least one antigenic epitope in that region. For example, in a recombinant *Spirulina* comprising multiple copies of the exogenous antigenic epitope and a scaffold protein, the exogenous antigenic epitope and the scaffold protein can be arranged in any one of the following patterns: (E)n-(SP), (SP)-(E)n, (SP)-(E)n-(SP), (E)$n_1$-(SP)-(E)$n_2$, (SP)-(E)$n_1$-(SP)-(E)$n_2$, and (SP)-(E)$n_1$-(SP)-(E)$n_2$-(SP), wherein E is the exogenous antigenic epitope, SP is the scaffold protein, and n, $n_1$, and $n_2$ represent the number of copies of the exogenous antigenic epitope. It is understood that the recombinant *Spirulina* may comprise more than one exogenous antigenic epitope and one or more scaffold proteins, where the multiple exogenous antigenic epitopes and the scaffold proteins can be arranged in various patterns as described above.

In some embodiments, recombinant *Spirulina* may comprise a fusion protein comprising at least one exogenous antigenic epitope, a scaffold protein, a VLP-forming viral protein, and/or a trimer-forming protein. In these embodiments, the at least one exogenous antigenic epitope can be tethered to or inserted into one or more scaffold proteins as described above and the fusion protein comprising the scaffold proteins and the at least one exogenous antigenic epitopes is tethered to or inserted into a VLP-forming viral protein and/or the trimer-forming protein.

Exemplary scaffold proteins include the oligomerization domain of C4b-binding protein (C4BP), a cholera toxin b subunit, or oligomerization domains of extracellular matrix proteins. In some embodiments, a scaffold protein used in the oral antigenic compositions of the present disclosure comprises a sequence from the oligomerization domain of C4BP selected from the group consisting of:

SAGAHAGWET-PEGCEQVLTGKRLMQCLPNPEDVKMA-LEVYKLSLEIEQLELQRDSA RQSTLDKEL (SEQ ID NO: 1),

WVIPEGCGHVLAGRKVMQCLPNPEDVKMA-LEVYKLSLEIELLEIQRDKARDPAMD (SEQ ID NO: 2),

WEYAEGCEQVVKGKKLMQCLPTPEEVRLA-LEVYKLYLEIQKLELQKDEAKQA (SEQ ID NO: 3), and

WVVPAGCEQVIAGRELTQCLPSVEDVKMALE-LYKLSLEIELLELQKDKAKKSTLESP L (SEQ ID NO: 4).

The recombinant *Spirulina* present in the oral antigenic compositions of the present disclosure can comprise multiple copies of the at least one exogenous antigenic epitope. In some embodiments, the recombinant *Spirulina* expresses an exogenous antigen (natural antigen or a fusion protein as described above), wherein the exogenous antigen comprises at least 1, 2, 3, 4, 5, 6, 7, 8, 9, or 10 copies of the at least one exogenous antigenic epitope per single molecule of the exogenous antigen. In some embodiments, the recombinant *Spirulina* expresses an exogenous antigen, wherein the exogenous antigen comprises 1-5, 2-5, 2-4, 3-6, 3-8, or 4-5 copies of the at least one exogenous antigenic epitope per single molecule of the exogenous antigen. In some embodiments, the recombinant *Spirulina* comprises at least 1, 2, 3, 4, 5, 6, 7, 8, 9, 10, 15, 20, 25, 30, 35, 40, 45, 50, 55, or 60 copies of the at least one exogenous antigenic epitope per single molecule of the exogenous antigen. In some embodiments, the recombinant *Spirulina* expresses an exogenous antigen, wherein the exogenous antigen comprises 1-10, 1-15, 1-20, 1-25, 1-30, 1-40, 1-50, 5-10, 5-15, 5-20, 5-25, 5-30, 5-40, 5-50, 10-25, 10-50, 10-60, 15-30, 15-45, 15-60, 20-50, 20-60, 20-70, 25-50, 25-60, 30-60, or 2-100 copies of the at least one exogenous antigenic epitope per single molecule of the exogenous antigen. In some embodiments, the recombinant *Spirulina* cell can comprise thousands of copies of the at least one exogenous antigenic epitope (e.g. by expressing the corresponding nucleic acid sequences via one or more vectors in the cell or via integration into the *Spirulina* genome).

The recombinant *Spirulina* present in the oral antigenic compositions of the present disclosure can comprise multiple copies of a nucleic acid sequence encoding the at least one exogenous antigenic epitope. The multiple copies of the nucleic acid sequence encoding the at least one exogenous antigenic epitope can be integrated into the genome of the *Spirulina* or can be present on one or more vectors introduced into the *Spirulina*. In some embodiments, the recombinant *Spirulina* comprises between 2 and 100 copies of the nucleic acid sequence encoding the at least one exogenous antigenic epitope. In some embodiments, the recombinant *Spirulina* comprises at least 1, 2, 3, 4, 5, 6, 7, 8, 9, or 10 copies of a nucleic acid sequence encoding the at least one exogenous antigenic epitope integrated into its genome or present on one or more vectors. In some embodiments, the recombinant *Spirulina* comprises 1-5, 2-5, 2-4, 3-6, 3-8, or 4-5 copies of a nucleic acid sequence encoding the at least one exogenous antigenic epitope integrated into its genome or present on one or more vectors. In some embodiments, the recombinant *Spirulina* comprises at least 1, 2, 3, 4, 5, 6, 7, 8, 9, 10, 15, 20, 25, 30, 35, 40, 45, 50, 55, or 60 copies of a nucleic acid sequence encoding the at least one exogenous antigenic epitope integrated into its genome or present on one or more vectors. In some embodiments, the recombinant *Spirulina* comprises 1-10, 1-15, 1-20, 1-25, 1-30, 1-40, 1-50, 5-10, 5-15, 5-20, 5-25, 5-30, 5-40, 5-50, 10-25, 10-50, 10-60, 15-30, 15-45, 15-60, 20-50, 20-60, 20-70, 25-50, 25-60, or 30-60 copies of a nucleic acid sequence encoding the at least one exogenous antigenic epitope integrated into its genome or present on one or more vectors.

In some embodiments, multiple copies of the at least one exogenous antigenic epitope present, for example, in the exogenous antigen, are linked in tandem, i.e., the first copy is immediately followed by the second copy without being separated by any amino acids, the second copy is immediately followed by the third copy, and so on. For example, if NANP (SEQ ID NO: 6) represents an antigenic epitope and at least 4 copies of this epitope linked in tandem are present in an exogenous antigen expressed in the recombinant *Spirulina*, then the recombinant *Spirulina* comprises a protein or a peptide comprising a sequence of —NANPNANPNANPNANP—(SEQ ID NO: 5). In some embodiments, the repeating antigenic epitope can be comprised in an exogenous antigen expressed by recombinant *Spirulina*, where the exogenous antigen can be a natural antigen (e.g., CSP protein from *Plasmodium*), a fusion protein, or natural or fusion peptides. In some embodiments, where the recombinant *Spirulina* comprises more than one exogenous antigenic epitope, the individual antigenic epitope can be similarly linked in tandem to the other antigenic epitope. For example, in a recombinant *Spirulina* comprising E1 and E2 as exogenous antigenic epitopes, these two epitopes can be linked in tandem in the following ways: (E1E2)x, (E2E1)x, (E1)x(E2)y, (E1)x(E2)y(E1)z, (E2)x(E1)y(E2)z, where x, y, and z represent the number of copies of the epitopes. Similar arrangement patterns for more than two exogenous antigenic epitopes are contemplated.

In some embodiments, multiple copies of the at least one exogenous antigenic epitope present in a protein can be separated by spacer sequences. In some embodiments, multiple copies of the exogenous antigenic epitope can be separated by about 1 to about 50 amino acid space sequences. For example, in some embodiments, multiple copies of the exogenous antigenic epitope can be separated by about 1, 2, 3, 4, 5, 6, 7, 8, 9, 10, 15, 20, 30, 40, or 50 amino acid spacer sequences. It is understood that in these embodiments, when more than 2 copies of the exogenous antigenic epitope are present, some copies can be linked in tandem and some copies can be separated by spacer sequences. For example, in a recombinant *Spirulina* comprising multiple copies of E1 as the at least one exogenous antigenic epitope, the multiple copies of this epitope can be separated in the following ways: (E1)x-S-(E1)y, (E1)(E1)x-S-(E1)y, (E1)x-S-(E1)y-S-(E1)z, where S represents the spacer sequence and x, y, and z represent the number of copies of the exogenous epitope. When multiple spacer sequences are present, these sequences can be identical or different in length and/or the amino acid sequence.

In embodiments, where the recombinant *Spirulina* comprises a protein comprising more than one exogenous antigenic epitope, the first exogenous antigenic epitope can be separated from the other exogenous antigenic epitope by spacer sequences of about 1, 2, 3, 4, 5, 6, 7, 8, 9, 10, 15, 20, 30, 40, or 50 amino acids. If multiple copies of each of the exogenous antigenic epitopes are present, some of the copies can be linked in tandem with the other epitope while some copies can be separated by spacer sequences; alternatively, all copies of one epitope can be linked in tandem followed by a spacer sequence followed by all copies of the second epitope, and the like. For example, in a recombinant *Spirulina* comprising E1 and E2 as exogenous antigenic epitopes, the two epitopes can be arranged in the following ways: (E1)x-S-(E2)y, (E2)x-S-(E1)y, (E1)x-S-(E2)y-S(E1)z-S-(E2)v, (E1)x-S-(E2)y(E1)z, (E1)x-S-(E2)y-S-(E1)z, (E2)x-S-(E1)y(E2)z, and the like, where v, x, y, and z represent the number of copies of the epitopes.

In some embodiments, a recombinant *Spirulina* may comprise one or more exogenous antigenic epitopes and multiple copies thereof in the arrangement patterns described above directly, i.e., without being part of or fused to another protein. In some embodiments, the one or more exogenous antigenic epitopes can be from the same antigen. In some embodiments, the one or more exogenous antigenic epitopes can be from different antigens. In some other embodiments, one or more exogenous antigenic epitopes and multiple copies thereof can be comprised in an exogenous antigen in the arrangement patterns described above. The exogenous antigen can be a natural antigen or a fusion protein as discussed above.

In some embodiments, the exogenous antigenic epitopes can be from different antigens that activate different types of immunity (e.g. innate, cellular, or humoral). In some embodiments, the one or more exogenous antigenic epitopes from different antigens are from at least one B-cell antigen and at least one T-cell antigen. In some embodiments, the one or more exogenous antigenic epitopes are in a fusion protein with a viral protein (e.g. a coronavirus spike protein). In some embodiments, the one or more exogenous antigenic epitopes are in a fusion protein with a viral protein (e.g. a coronavirus spike protein) with one epitope at either terminus. In some embodiments, the one or more exogenous antigenic epitopes are a B-cell epitope fused to one terminus of a virus protein and a T-cell epitope fused to the other terminus of the virus protein.

In some embodiments, recombinant *Spirulina* comprises a fusion protein comprising a VLP-forming viral protein or a trimer-forming protein and one or more exogenous antigenic epitopes, where the exogenous antigenic epitopes and multiple copies thereof, if present, can be arranged within the fusion protein in various patterns as described above. In some other embodiments, recombinant *Spirulina* may comprise a fusion protein comprising a scaffold protein and one or more exogenous antigenic epitopes, where the exogenous antigenic epitopes and multiple copies thereof, if present, can be arranged within the fusion protein in various patterns as described above. In some other embodiments, recombinant *Spirulina* may comprise a fusion protein comprising a VLP-forming viral protein, a trimer-forming protein, and/or a scaffold protein, and one or more exogenous antigenic epitopes, where the exogenous antigenic epitopes and multiple copies thereof, if present, can be arranged within the fusion protein in various patterns as described above.

The oral antigenic compositions provided by the present disclosure comprise a recombinant *Spirulina*, wherein the recombinant *Spirulina* comprises at least one exogenous antigenic epitope in any of the ways described above.

In various embodiments, oral antigenic compositions of the present disclosure comprise a recombinant *Spirulina* comprising at least one exogenous antigenic epitope derived from (e.g. a portion or fragment thereof, or antigenic variant thereof) an infectious microorganism, a tumor antigen or a self-antigen associated with an autoimmune disease.

In some embodiments, oral antigenic compositions comprise a recombinant *Spirulina* comprising at least one exogenous antigenic epitope derived from an infectious microorganism such as a virus, bacterium, parasite, or fungus. The infectious microorganism can be a microorganism that causes infections in a human or an animal such as a species of livestock, poultry, and fish.

In some embodiments, oral antigenic compositions of the present disclosure comprise a recombinant *Spirulina* comprising at least one antigenic epitope from a virus including but not limited to, bacteriophage, RNA bacteriophage (e.g. MS2, AP205, PP7 and Qβ), *Helicobacter pylori*, infectious haematopoietic necrosis virus (IHNV), parvovirus, Herpes Simplex Virus, Hepatitis A virus, Hepatitis B virus, Hepatitis C virus, Measles virus, Mumps virus, Rubella virus, Human Immunodeficiency Virus (HIV), Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, and White Spot Syndrome Virus. In some embodiments, oral antigenic compositions of the present disclosure comprise a recombinant *Spirulina* comprising at least one antigenic epitope from IHNV. In some embodiments, oral antigenic compositions of the present disclosure comprise a recombinant *Spirulina* comprising at least one antigenic epitope from a parvovirus, e.g., canine parvovirus.

In some embodiments, oral antigenic compositions comprise a recombinant *Spirulina* comprising at least one antigenic epitope from a bacterium including but not limited to, *Mycobacterium, Streptococcus, Staphylococcus, Shigella, Campylobacter, Salmonella, Clostridium, Corynebacterium, Pseudomonas, Neisseria, Listeria, Vibrio, Bordetella, E. coli* (including pathogenic *E. coli*), and *Legionella.*

In some embodiments, oral antigenic compositions comprise a recombinant *Spirulina* comprising at least one antigenic epitopes from a parasite including but not limited to, *Plasmodium, Trypanosoma, Toxoplasma, Giardia*, and *Leishmania, Cryptosporidium*, helminthic parasites: *Trichuris* spp. (whipworms), *Enterobius* spp. (pinworms), *Ascaris* spp. (roundworms), *Ancylostoma* spp. and *Necator* spp. (hookworms), *Strongyloides* spp. (threadworms), *Dracunculus* spp. (Guinea worms), *Onchocerca* spp. and *Wuchereria* spp. (filarial worms), *Taenia* spp., *Echinococcus* spp., and *Diphyllobothrium* spp. (human and animal cestodes), *Fasciola* spp. (liver flukes) and *Schistosoma* spp. (blood flukes).

In some embodiments, oral antigenic compositions comprise a recombinant *Spirulina* comprising at least one antigenic epitope from a *Plasmodium* selected from the group consisting of: *P. falciparum, P. malariae, P. ovale* and *P. vivax.*

In some embodiments, oral antigenic compositions comprise a recombinant *Spirulina* comprising at least one antigenic epitope from a fungus including but not limited to, *Aspergillus, Candida, Blastomyces, Coccidioides, Cryptococcus*, and *Histoplasma*. In some embodiments, oral antigenic compositions comprise a recombinant *Spirulina* comprising at least one antigenic epitope from *Candida albicans* or *Candida* auris.

In some embodiments, provided herein are oral antigenic compositions comprising a recombinant *Spirulina*, wherein the recombinant *Spirulina* comprises at least one antigenic epitope from a *Plasmodium*. In some embodiments, provided herein are oral antigenic composition comprising a recombinant *Spirulina*, wherein the recombinant *Spirulina* comprises at least one antigenic epitope derived from a *Plasmodium* antigen selected from the group consisting of: circumsporozoite protein (CSP or CS), thrombospondin-related anonymous protein (TRAP), Apical Membrane Antigen 1 (AMA1), the major merozoite surface proteins 1-3 (MSP1-3), sexual stage antigen 25 (s25), and sexual stage antigen s230. In some embodiments, the at least one *Plasmodium* antigenic epitope is comprised in a VLP. In some embodiments, the VLP comprises the sequence of a capsid protein of a virus. In an exemplary embodiment, the capsid protein is woodchuck hepadnaviral core antigen (WHcAg).

In some embodiments, provided herein are oral antigenic compositions comprising a recombinant *Spirulina*, wherein the recombinant *Spirulina* comprises at least one antigenic epitope derived from a circumsporozoite protein of *Plasmodium*. In some embodiments, provided herein are oral antigenic compositions comprising a recombinant *Spirulina*, wherein the recombinant *Spirulina* comprises a VLP containing at least one antigenic epitope derived from a circumsporozoite protein of *Plasmodium*. In some embodiments, the VLP comprises the sequence of a capsid protein of a virus. In an exemplary embodiment, the capsid protein is woodchuck hepadnaviral core antigen (WHcAg).

In some embodiments, oral antigenic compositions of the present disclosure comprise a recombinant *Spirulina*, wherein the recombinant *Spirulina* comprises one or more antigenic epitopes from Table 1 or a fusion protein comprising an epitope-containing sequence selected from Table 1.

TABLE 1

| Epitope | Epitope containing sequence | SEQ ID NO |
|---|---|---|
| *P. falciparum* CSP | NANP | 6 |
| *P. falciparum* CSP | NVDP | 7 |
| *P. falciparum* CSP | NPDP | 8 |
| *P. falciparum* CSP | KLKQPGDG**NPDP**NA**NPN**VDPNANPNVDPNANPNVDPNANP | 9 |
| *P. falciparum* CSP | EYLKKIQNSLSTEWSPCSVT | 10 |
| *P. falciparum* CSP | NANPNANPNANPNANPNANPNANPNANPNANPNANPNANPNANPNANPNANPNANPNANP | 11 |
| *P. falciparum* CSP | GDGN**PDP**NA**NPN**VDPNANPNVDPNANPNVDPNANP | 12 |
| *P. falciparum* CSP | GDGNPDPNANPNVDPNANPNVDPNANPNVDPNANPNANPNANPNANPNANPNANPNANPNANPNANPNANPNANPNANPNANPNANPNANP | 13 |
| *P. falciparum* CSP | DGNNEDNEKLRKPKHKKLKQPGDGNPDPNANPNVDPNANPNVDPNANPNVDPNANPNANPNANPNANPNANPNANPNANPNANPNANPNANPNANPNANPNANPNANP | 14 |
| *P. falciparum* TRAP | HPSDGKC | 15 |
| *P. falciparum* TRAP | DRYI | 16 |
| *P. falciparum* TRAP | TRPHGR | 17 |
| *P. yoelii* CSP | QGPGAPQGPGAPQGPGAPQGPGAPQGPGAPQGPGAPQEPPQQPPQQPPQQPPQQPPQQ | 18 |
| *P. yoelii* CSP | NEDSYVPSAEQILEF | 19 |
| *P. falciparum* CSP | EEGNANPNANPNANPNANPNANPNANPNANPNANPNANPNANPNANPNANPNANPNANPNANPGEE | 20 |
| Canine parvovirus 2L21 peptide epitope | SDGAVQPDGGQPAVRNERATG | 21 |
| Canine parvovirus 3L17 peptide epitope | DGAVQPDGGQPAVRNER | 22 |
| IHNV E1 + E2 epitopes | DDENRGLIAYPTSIRSLSVGGSGGSDLISVVYNSGSEILSF | 23 |

TABLE 1-continued

| Epitope | Epitope containing sequence | SEQ ID NO |
|---|---|---|
| IHNV DIII epitope | DDENRGLIAYPTSIRSLSVGNDGGSGGSSQEIK<br>AHLFVDKISNRVVKATSYGHHPWGLHQACMI<br>EFCGQQWIRTDLGDLISVVYNSGSEILSFPKCE<br>DKTVGPAEGGG | 24 |
| IHNV DIII epitope | DDENRGLIAYPTSIRSLSVGNDGGSGGSSQEIK<br>GHLFVDKISNRVVKATSYGHHPWGLHQACMI<br>EFCGQQWIRTDLGDLISVVYNSGSEILSFPKCE<br>DKTVG | 64 |
| HIV gp41 fusion peptide A epitope | AVGIGAVF | 65 |
| HIV gp41 fusion peptide B epitope | AVGLGAVF | 66 |
| HIV gp41 fusion peptide C epitope | AVGIGAMI | 67 |

In some embodiments, oral antigenic compositions of the present disclosure comprise a recombinant *Spirulina*, wherein the recombinant *Spirulina* comprises a fusion protein comprising one or more antigenic epitopes, wherein the fusion protein comprises a sequence selected from Table 2.

TABLE 2

| Description of the fusion protein | Sequence | SEQ ID NO |
|---|---|---|
| *P. yoelii* CSP B cell epitope in monomer WHcAg | MDIDPYKEFGSSYQLLNFLPLDFFPDLNALVD<br>TATALYEEELTGREHCSPHHTAIRQALVCWD<br>ELTKLIAWMSSNITSQGPGAPQGPGAPQGPG<br>APQGPGAPQGPGAPQGPGAPQEPPQQPPQQP<br>PQQPPQQPPQQEQVRTIIVNHVNDTWGLKVR<br>QSLWFHLSCLTFGQHTVQEFLVSFGVWIRTP<br>APYRPPNAPILSTLPEHTVINEDSYVPSAEQIL<br>EFEQKLISEEDLEQKLISEEDL | 25 |
| *P. falciparum* CSP B cell epitope in tandem WHcAg dimer | MDIDPYKEFGSSYQLLNFLPLDFFPDLNALVD<br>TATALYEEELTGREHCSPHHTAIRQALVCWD<br>ELTKLIAWMSSNITSEQVRTIIVNHVNDTWGL<br>KVRQSLWFHLSCLTFGQHTVQEFLVSFGVWI<br>RTPAPYRPPNAPILSTLPEHTVIGGSGGSGGSG<br>GSGGSDIDPYKEFGSSYQLLNFLPLDFFPDLN<br>ALVDTATALYEEELTGREHCSPHHTAIRQAL<br>VCWDELTKLIAWMSSNITSEEGNANPNANPN<br>ANPNANPNANPNANPNANPNANPNANPNAN<br>PNANPNANPNANPNANPNANPGEEEQVRTII<br>VNHVNDTWGLKVRQSLWFHLSCLTFGQHTV<br>QEFLVSFGVWIRTPAPYRPPNAPILSTLPEHTV<br>IHHHHHH | 26 |
| *P. falciparum* CSP B cell epitope + Salmonella fliC sequences in tandem WHcAg dimer | MDIDPYKEFGSSYQLLNFLPLDFFPDLNALVD<br>TATALYEEELTGREHCSPHHTAIRQALVCWD<br>ELTKLIAWMSSNITSEQVRTIIVNHVNDTWGL<br>KVRQSLWFHLSCLTFGQHTVQEFLVSFGVWI<br>RTPAPYRPPNAPILSTLPEHTVIGGSGGSGGSG<br>GSGGSDIDPYKEFGSSYQLLNFLPLDFFPDLN<br>ALVDTATALYEEELTGREHCSPHHTAIRQAL<br>VCWDELTKLIAWMSSNITSEEGAQVINTNSLS<br>LLTQNNLNKSQSALGTAIERLSSGLRINSAKD<br>DAAGQAIANRFTANIKGLTQASRNANDGISIA<br>QTTEGALNEINNNLQRVRELAVQSANSTNSQ<br>SDLDSIQAEITQRLNEIDRVSGQTQFNGVKVL<br>AQDNTLTIQVGANDGETIDIDLKQINSQTLGL<br>DTLNVQGSNANPNANPNANPNANPNANPNA<br>NPNANPNANPNANPNANPNANPNANPNANP<br>NANPNANPGSTTTENPLQKIDAALAQVDTLR<br>SDLGAVQNRFNSAITNLGNTVNNLTSARSRIE<br>DSDYATEVSNMSRAQILQQAGTSVLAQANQ<br>VPQNVLSLLRGEEEQVRTIIVNHVNDTWGLK<br>VRQSLWFHLSCLTFGQHTVQEFLVSFGVWIR<br>TPAPYRPPNAPILSTLPEHTVIHHHHHH | 27 |

TABLE 2-continued

| Description of the fusion protein | Sequence | SEQ ID NO |
|---|---|---|
| Canine parvovirus 2L21 peptide epitope in 2x configuration; monomer WhcAg | MDIDPYKEFGSSYQLLNFLPLDFFPDLNALVD<br>TATALYEEELTGREHCSPHHTAIRQALVCWD<br>ELTKLIAWMSSNITSEEGSDGAVQPDGGQPA<br>VRNERATGGGSSDGAVQPDGGQPAVRNERA<br>TGGEEEQVRTIIVNHVNDTWGLKVRQSLWFH<br>LSCLTFGQHTVQEFLVSFGVWIRTPAPYRPPN<br>APILSTLPEHTVIHHHHHH | 28 |
| Canine parvovirus 3L17 peptide epitope in 4x configuration; monomer WhcAg | MDIDPYKEFGSSYQLLNFLPLDFFPDLNALVD<br>TATALYEEELTGREHCSPHHTAIRQALVCWD<br>ELTKLIAWMSSNITSEEGDGAVQPDGGQPAV<br>RNERGGSDGAVQPDGGQPAVRNERGGSDGA<br>VQPDGGQPAVRNERGGSDGAVQPDGGQPAV<br>RNERGEEEQVRTIIVNHVNDTWGLKVRQSL<br>WFHLSCLTFGQHTVQEFLVSFGVWIRTPAPY<br>RPPNAPILSTLPEHTVIHHHHHH | 29 |
| IHNV E1 + E2 epitopes in tandem WHcAg dimer | MDIDPYKEFGSSYQLLNFLPLDFFPDLNALVD<br>TATALYEEELTGREHCSPHHTAIRQALVCWD<br>ELTKLIAWMSSNITSEQVRTIIVNHVNDTWGL<br>KVRQSLWFHLSCLTFGQHTVQEFLVSFGVWI<br>RTPAPYRPPNAPILSTLPEHTVIGGSGGSGGSG<br>GSGGSDIDPYKEFGSSYQLLNFLPLDFFPDLN<br>ALVDTATALYEEELTGREHCSPHHTAIRQAL<br>VCWDELTKLIAWMSSNITSPGGSGDDENRGL<br>IAYPTSIRSLSVGGSGGSDLISVVYNSGSEILSF<br>PGGSGEQVRTIIVNHVNDTWGLKVRQSLWFH<br>LSCLTFGQHTVQEFLVSFGVWIRTPAPYRPPN<br>APILSTLPEHTVIEQKLISEEDLEQKLISEEDL | 30 |
| IHNV DIII epitope in tandem WHcAg dimer | MDIDPYKEFGSSYQLLNFLPLDFFPDLNALVD<br>TATALYEEELTGREHCSPHHTAIRQALVCWD<br>ELTKLIAWMSSNITSEQVRTIIVNHVNDTWGL<br>KVRQSLWFHLSCLTFGQHTVQEFLVSFGVWI<br>RTPAPYRPPNAPILSTLPEHTVIGGSGGSGGSG<br>GSGGSDIDPYKEFGSSYQLLNFLPLDFFPDLN<br>ALVDTATALYEEELTGREHCSPHHTAIRQAL<br>VCWDELTKLIAWMSSNITSPGGSGDDENRGL<br>IAYPTSIRSLSVGNDGGSGGSSQEIKAHLFVD<br>KISNRVVKATSYGHHPWGLHQACMIEFCGQ<br>QWIRTDLGDLISVVYNSGSEILSFPKCEDKTV<br>GPAEGGGPAGGSGEQVRTIIVNHVNDTWGLK<br>VRQSLWFHLSCLTFGQHTVQEFLVSFGVWIR<br>TPAPYRPPNAPILSTLPEHTVIEQKLISEEDLEQ<br>KLISEEDL | 31 |

In some embodiments, oral antigenic compositions of the present disclosure comprise a recombinant *Spirulina*, wherein the recombinant *Spirulina* expresses a protein comprising a sequence selected from Table 3. In some embodiments, recombinant *Spirulina* expresses a fusion protein comprising one or more antigenic epitopes from the proteins listed in Table 3.

TABLE 3

| *P. falciparum* CSP sequences | |
|---|---|
| CSP Accession Number | CSP sequence |
| FJ232362 | MRKLAILSVSSFLFVEALFQEYQCYGSSSNTRVLNELNYDNAGTNLY<br>NELEMNYYGKQE NWYSLKKNSRSLGENDDGNNNNGDNGREGKDE<br>DKRDGNNEDNEKLRKPKHK**KLKQP**GDGN**PDP**N**ANPNV**DPNANPNV<br>DPNANPNVDPNANPNANPNANPNANPNANPNANPNANPNANPNANP<br>NANPNANPNANPNANPNANPNANPNANPNANPNANPNANPNANPN<br>ANPNANPNANPNANPNANPNANPNANPNANPNANPNANPNANPNA<br>NPNANPNANPNANPNANPNANPNANPNANPNANPNANPNKNNQGNGQGH<br>NMPNDPNRNVDENANANNDVKNNNNEEPSDKHIEEYLKKIQNSLSTE<br>WSPCSVTCGNGIQVRIKPGSANKPKDELNYENDIEKKICKMEKCSSVF<br>NVV NSSIGLIMVLSFLFLN (SEQ ID NO: 32) |

TABLE 3-continued

| | |
|---|---|
| GQ890770 | MRKLAILSVSSFLFVEALFQEYQCYGSSSNTRVLNELNYDNAGTNLY<br>NELEMNYYGKQE NWYSLKKNSRSLGENDDGNNNNGDNGREGKDE<br>DKRDGNNEDNEKLRKPKHKKLKQPGDGNPDPNANPNVDPNANPNV<br>DPNANPNVDPNANPNANPNANPNANPNANPNANPNANPNANPNANP<br>NANPNANPNANPNANPNANPNANPNVDPNANPNANPNANPNANPN<br>ANPNANPNANPNANPNANPNANPNANPNANPNANPNANPNANPNA<br>NPNANPNANPNANPNANPNANPNANPNANPNANPNANPNKNNQGN<br>GQGHNMPNDPNRNVDENANANNDENNNNEEPSDKHIEQYLKKIQY<br>SLSTEWSPCSVTCGNGIQVRIKPGSADKPKDQLDYENDIEKKICKMEK<br>CSSVFNVV NSSIGLIMVLSFLFLN (SEQ ID NO: 33) |
| FJ232364 | MRKLAILSVSSFLFVEALFQEYQCYGSSSNTRVLNELNYDNAGTNLY<br>NELEMNYYGKQENWYSLKKNSRSLGENDDGNNNNGDNGREGKDE<br>DKRDGNNEDNEKLRKPKHKKLKQPGDGNPDPNANPNVDPNANPNV<br>DPNANPNVDPNANPNANPNANPNANPNANPNANPNANPNANPNANP<br>NANPNANPNANPNANPNANPNANPNANPNANPNANPNANPNANPN<br>ANPNANPNANPNANPNANPNANPNANPNANPNANPNANPNANPNA<br>NPNANPNANPNANPNANPNANPNANPNKNNQGNGQGHNMPNDPNR<br>NVDENANANNAVKNNNNEEPSDKHIEQYLKKIQNSLSTEWSPCSVTC<br>GNGIQVRIKPGSANKPKDELDYENDIEKKICKMEKCSSVFNVVNSSIG<br>LIMVLSFLFLN (SEQ ID NO: 34) |
| M22982.1 | MMRKLAILSVSSFLFVEALFQEYQCYGSSSNTRVLNELNYDNAGTNL<br>YNELEMNYYGKQENWYSLKKNSRSLGENDDGNNEDNEKLRKPKH<br>KKLKQPADGNPDPNANPNVDPNANPNVDPNANPNVDPNANPNANP<br>NANPNANPNANPNANPNANPNANPNANPNANPNANPNANPNANPN<br>ANPNANPNANPNANPNANPNANPNVDPNANPNANPNANPNANPNA<br>NPNANPNANPNANPNANPNANPNANPNANPNANPNANPNANPNAN<br>PNANPNANPNKNNQGNGQGHNMPNDPNRNVDENANANSAVKNNN<br>NEEPSDKHIKEYLNKIQNSLSTEWSPCSVTCGNGIQVRIKPGSANKPK<br>DELDYANDIEKKICKMEKCSSVFNVVNSSIGLIMVLSFLFLN (SEQ ID<br>NO: 35) |
| FJ232355 | MRKLAILSVSSFLFVEALFQEYQCYGSSSNTRVLNELNYDNAGTNLY<br>NELEMNYYGKQENWYSLKKNSRSLGENDDGNNNNGDNGREGKDED<br>KRDGNNEDNEKLRKPKHKKLKQPGDGNPDPNANPNVDPNANPNVDP<br>NANPNVDPNANPNANPNANPNANPNANPNANPNANPNANPNANPN<br>ANPNANPNANPNANPNANPNANPNANPNANPNANPNANPNANPNA<br>NPNANPNANPNANPNANPNANPNANPNANPNANPNANPNANPNAN<br>PNANPNANPNANPNANPNANPNANPNANPNKNNQGNGQGHNMPND<br>PNRNVDENANANNAVKNNNNEEPSDKHIEQYLKKIQNSLSTEWSPCS<br>VTCGNGIQVRIKPGSANKPKDELDYENDIEKKICKMEKCSSVFNVV<br>NSSIGLIMVLSFLFLN (SEQ ID NO: 36) |
| AB502949 | MMRKLAILSVSSFLFVEALFQEYQCYGSSSNTRVLNELNYDNAGTNL<br>YNELEMNYYGKQENWYSLKKNSRSLGENDDGNNNNGDNGREGKDE<br>DKRDGNNEDNEKLRKPKHKKLKQPGDGNPDPNANPNVDPNANPNV<br>DPNANPNVDPNANPNVDPNANPNANPNANPNANPNANPNANPNANP<br>NANPNANPNANPNANPNANPNANPNANPNANPNANPNANPNANPN<br>ANPNANPNANPNANPNANPNANPNANPNANPNANPNANPNANPNA<br>NPNANPNANPNANPNANPNANPNANPNKNNQGNGQGHNMPN<br>DPNRNVDENANANNAVKNNNNEEPSDKHIEQYLKKIQNSLSTEWSPC<br>SVTCGNGIQVRIKPGSANKPKDELDYENDIEKKICKMEKCSSVFNVV<br>NSSIGLIMVLSFLFLN (SEQ ID NO: 37) |
| AB715565 | MMRKLAILSVSSFLFVEALFQEYQCYGSSSNTRVLNELNYDNAGTNL<br>YNELEMNYYGKQENWYSLKKNSRSLGENDDGNNNNGDNGREGKD<br>EDKRDGNNEDNEKLRKPKHKKLKQPGDGNPDPNANPNVDPNANPN<br>VDPNANPNVDPNANPNANPNANPNANPNANPNANPNANPNANPNA<br>NPNANPNANPNANPNANPNANPNANPNANPNANPNANPNANPNAN<br>PNANPNANPNANPNANPNANPNANPNANPNANPNANPNANPNANPN<br>ANPNANPNANPNANPNANPNKNNQGNGQGHNMPNDPNRNVDENAN<br>ANNAVKNNNNEEPSDKHIEQYLKKIQNSLSTEWSPCSVTCGNGIQVRI<br>KPGSANKPKDELDYENDIEKKICKMEKCSSVFNVV NSSIGLIMVLSFL<br>FLN (SEQ ID NO: 38) |
| AB116603 | MMRKLAILSVSSFLFVEALFQEYQCYGSSSNTRVLNELNYDNAGTNL<br>YNELEMNYYGKQENWYSLKKNSRSLGENDDGNNNNGDNGREGKDE<br>DKRDGNNEDNEKLRKPKHKKLKQPGDGNPDPNANPNVDPNANPNV<br>DPNANPNVDPNANPNANPNANPNANPNANPNANPNANPNANPNANP<br>NANPNANPNANPNANPNANPNANPNANPNANPNANPNANPNANPN<br>ANPNANPNANPNANPNANPNANPNANPNANPNANPNANPNANPNA<br>NPNANPNANPNANPNANPNKNNQGNGQGHNMPNDPNRNVDENAN<br>ANNAVKNNNNEEPSDKHIEQYLK KIQNSLSTEWSPCSVTCGNGIQV<br>RIKPGSANKPKDELDYENDIEKKICKMEKCSSVFNVV NSSIGLIMVL<br>SFLFLN (SEQ ID NO: 39) |
| AB503046 | MMRKLAILSVSSFLFVEALFQEYQCYGSSSNTRVLNELNYDNAGTNL<br>YNELEMNYYGKQENWYSLKKNSRSLGENDDGNNNNGDNGREGKD<br>EDKRDGNNEDNEKLRKPKHKKLKQPGDGNPDPNANPNVDPNANP |

TABLE 3-continued

| | |
|---|---|
| | NVDPNANPNVDPNANPNANPNANPNANPNANPNANPNANPNANPN ANPNANPNANPNANPNANPNANPNANPNVDPNANPNANPNANPN ANPNANPNANPNANPNANPNANPNANPNANPNANPNANPNANPNA NPNANPNANPNANPNANPNKNNQGNGQGHNMPNDPNRNVDENANA NNAVKNNNNEEPSDKHIEQYLKKIQNSLSTEWSPCSVTCGNGIQVRIK PGSADKPKDQLDYENDIEKKICKMEKCSSVFNVVNSSIGLIMVLSFLF LN (SEQ ID NO: 40) |

*P. falciparum* TRAP sequences

| TRAP accession number | TRAP Sequence |
|---|---|
| AB807859 | MNHLGNVKYLVIVFLIFFDLFLVNGRDVQNNIVDEIKYREEVCNDEV DLYLLMDCSGSIRRHNWVKHAVPLAMKLIQQLNLNENAIHLYLNIFS NAREIIRLHSDASKNKEKALIIIKSLLNTNLPYGRTNLTDALLQVRKHL NDRINRENANQLVVILTDGIPDSIQDSLKESRKLNDRGVKIAVFGIGQG INVAFNRFLVGCHPSDGKCNLYADSAWENVKNVIGPFMKAVCVEVE KTASCGVWDEWSPCSVTCGKGTRSRKREILHEGCTSELQEQCEEERC PPKREPLDVPDEPEDDQPRPRGDNFAVEKPEENIIDNNPQEPSPNPEEG KGENPNGFDLDENPENPPNPPNPPNPDIPEQEPNIPEDSEKEVPSDVPK NPEDDREENFDIPKKPENKHDNQNNLPNDKSDRYIPYSPLPPKVLDNE RKQSDPQSQDNNGNRHVPNSEDRETRPHGRNNENRSYNRKHNNTPK HPEREEHEKPDNNKKKGGSDNKYKIAGGIAGGLALLACAGLAYKFV VPGAATPYAGEPAPFDETLGEEDKDLDEPEQFRLPEENEWN (SEQ ID NO: 41) |
| AB807845 | MNHLGNVKYLVIVFLIFFDLFLVNGRDVQNNIVDEIKYREEVCNDEV DLYLLMDCSGSIRRHNWVKHAVPLAMKLIQQLNLNENAIHLYVNIFS NNAKEIIRLHSDASKNKEKALIIIKSLLSTNLPYGRTNLSDALLQVRKH LNDRINRENANQLVVILTDGIPDSIQDSLKESRKLNDRGVKIAVFGIGQ GINVAFNRFLVGCHPSDGKCNLYADSAWENVKNVIGPFMKAVCVEV EKTASCGVWDEWSPCSVTCGKGTRSRKREILHEGCTSELQEQCEEER CPPKREPLDVPDEPEDDQPRPRGDNFAVEKPEENIIDNNPQEPSPNPEE GKGENPNGFDLDENPENPPNPDIPEQEPNIPEDSEKEVPSDVPKNPEDD REENFDIPKKPENKHDNQNNLPNDKSDRSIPYSPLPPKVLDNERKQSD PQSQDNNGNRHVPNSEDRETRPHGRNNENRSYNRKYNDTPKHPEREE HEKPDNNKKKGGSDNKYKIAGGIAGGLALLACAGLAYKFVVPGAAT PYAGEPAPFDETLGEEDKDLDEPEQFRLPEENEWN (SEQ ID NO: 42) |
| X13022 | MNHLGNVKYLVIVFLIFFDLFLVNGRDVQNNIVDEIKYSEEVCNDQV DLYLLMDCSGSIRRHNWVNHAVPLAMKLIQQLNLNDNAIHLYVNVF SNNAKEIIRLHSDASKNKEKALIIIRSLLSTNLPYGRINLTDALLQVRK HLNDRINRENANQLVVILTDGIPDSIQDSLKESRKLSDRGVKIAVFGIG QGINVAFNRFLVGCHPSDGKCNLYADSAWENVKNVIGPFMKAVCVE VEKTASCGVWDEWSPCSVTCGKGTRSRKREILHEGCTSEIQEQCEEER CPPKWEPLDVPDEPEDDQPRPRGDNSSVQKPEENIIDNNPQEPSPNPEE GKDENPNGFDLDENPENPPNPDIPEQKPNIPEDSEKEVPSDVPKNPEDD REENFDIPKKPENKHDNQNNLPNDKSDRNIPYSPLPPKVLDNERKQSD PQSQDNNGNRHVPNSEDRETRPHGRNNENRSYNRKYNDTPKHPEREE HEKPDNNKKKGESDNKYKIAGGIAGGLALLACAGLAYKFVVPGAAT PYAGEPAPFDETLGEEDKDLDEPEQFRLPEENEWN (SEQ ID NO: 43) |
| AB807836 | MNHLGNVKYLVIVFLIFFDLFLVNGRDVQNNIVDEIKYREEVCNDEV DLYLLMDCSGSIRRHNWVKHAVPLAMKLIQQLNLNESAIHLYVNIFS NNAREIIRLHSDASKNKEKALIIIKSLLSTNLPYGRINLTDALLQVRKH LNDRINRENASQLVVILTDGIPDSIQDSLKESRKLNDLGVKIAVFGIGQ GINVAFNRFLVGCHPSDGKCNLYADSAWENVKNVIGPFMKAVCVEV EKTASCGVWDEWSPCSVTCGKGTRSRKREILHEGCTSELQEQCEEER CPPKREPLDVPHEPEDDQPRPRGDNFAVEKPKENIIDNNPQEPSPNPEE GKGENPNGFDLDENPENPPNPDIPEQEPNIPEDSEKEVPSDVPKNPEDD REENFDIPKKPENKHDNQNNLPNDKSDRSIPYSPLPPKVLDNERKQSD PQSQDNNGNRHVPNSEDRETRPHGRNNENRSYNRKYNDTPKHPEREE HEKPDNNKKKGGSDNKYKIAGGIAGGLALLACAGLAYKFVVPGAAT PYAGEPAPFDETLGEEDKDLDEPEQFRLPEENEWN (SEQ ID NO: 44) |
| AB807839 | MNHLGNVKYLVIVFLIFFDLFLVNGRDVQNNIVDEIKYREEVCNDEV DLYLLMDCSGSIRRHNWVNHAVPLAMKLIQQLNLNESAIHLYLNIFS NNAREIIRLHSDASKNKEKALIIIKSLLNTNLPYGRTNLTDALLQVRKH LNDRINRENANQLVVILTDGIPDSIQDSLKESRKLNDRGVKIAVFGIGQ GINVAFNRFLVGCHPSDGKCNLYADSAWENVKNVIGPFMKAVCVEV EKTASCGVWDEWSPCSVTCGKGTRSRKREILHEGCTSELQEQCEEER CPPKREPLDVPHEPEDDQPRPRGDNFVVEKPEENIIDNNPQEPSPNPEE GKGENPNGFDLDENPENPPNPPNPPNPPNPDIPEQEPNIPEDSEKEVPSD VPKNPEDDREENFDIPKKPENKHDNQNNLPNDKSDRYIPYSPLPPKVL DNERKQSDPQSQDNNGNRHVPNSEDRETRPHGRNNENRSYNRKHNN TPKHPEREEHEKPDNNKKKGGSDNKYKIAGGIAGGLALLACAGLAY KFVVPGAATPYAGEPAPFDETLGEEDKDLDEPEQFRLPEENEWN (SEQ ID NO: 45) |

TABLE 3-continued

| | Sequences of other exogenous antigens |
|---|---|
| IHNV Glycoprotein | MDTMITTPLILILITCGANSQTVKPDTASESDQPTWSNPLFTYPEGCTL<br>DKLSKVNASQLRCPRIFDDENRGLIAYPTSIRSLSVGNDLGEIHTQGNH<br>IHKVLYRTICSTGFFGGQTIEKALVEMKLSTKEAGAYDTTTAAALYFP<br>APRCQWYTDNVQNDLIFYYTTQKSVLRDPYTRDFLDSDFIGGKCTKS<br>PCQTHWSNVVWMGDAGIPACDSSQEIKGHLFVDKISNRVVKATSYG<br>HHPWGLHQACMIEFCGQQWIRTDLGDLISVVYNSGSEILSFPKCEDKT<br>VGMRGNLDDFAYLDDLVKASESREECLEAHAEIISTNSVTPYLLSKFR<br>SPHPGINDVYAMHKGSIYHGMCMTVAVDEVSKDRTTYRAHRATSFT<br>KWERPFGDEWEGFHGLHGNNTTIIPDLEKYVAQYKMSMMEPMSIKS<br>VPHPSILALYNETDVSGISIRKLDSFDLQSLHWSFWPTISALGGIPFVLL<br>LAVAACCCWSGRPPTPSVPQSIPMYHLANRS (SEQ ID NO: 68) |
| Canine parvovirus VP2 capsid | MSDGAVQPDGGQPAVRNERATGSGNGSGGGGGGGSGGVGISTGTFN<br>NQTEFKFLENGWVEITANSSRLVHLNMPESENYRRVVVNNLDKTAV<br>NGNMALDDTHAQIVTPWSLVDANAWGVWFNPGDWQLIVNTMSELH<br>LVSFEQEIFNVVLKTVSESATQPPTKVYNNDLTASLMVALDSNNTMPF<br>TPAAMRSETLGFYPWKPTIPTPWRYYFQWDRTLIPSHTGTSGTPTNIY<br>HGTDPDDVQFYTIENSVPVHLLRTGDEFATGTFFFDCKPCRLTHTWQT<br>NRALGLPPFLNSLPQAEGGTNFGYIGVQQDKRRGVTQMGNTNIITEAT<br>IMRPAEVGYSAPYYSFEASTQGPFKTPIAAGRGGAQTDENQAADGDP<br>RYAFGRQHGQKTTTTGETPERFTYIAHQDTGRYPEGDWIQNINFNLPV<br>TNDNVLLPTDPIGGKTGINYTNIFNTYGPLTALNNVPPVYPNGQIWDK<br>EFDTDLKPRLHVNAPFVCQNNCPGQLFVKVAPNLTNEYDPDASANM<br>SRIVTYSDFWWKGKLVFKAKLRASHTWNPIQQMSINVDNQFNYVPS<br>NIGGMKIVYEKSQLAPRKLY (SEQ ID NO: 69) |
| HIV envelope glycoprotein GP41 | MRVRGMQRNWQHLGKWGFLFLGILIICNAEDNLWVTVYYGVPVWK<br>EATTTLFCASDAKGYEREVHNVWATHACVPTDPSPQEMVLENVTEN<br>FNMWKNEMVEQMHTDIISLWDQSLKPCVKLTPLCVTLNCTDVDTNR<br>TQNDNMTEERGVLKNCSFNMTTEVKDKRLKVSALFYRLDVVPISNNS<br>NSSEYRLINCNTSTIKQACPKVSWDPIPIHYCAPAGYAILQCRDKQFNG<br>TGPCKNVSTVQCTHGIKPVVSTQLLLNGSLAEKDIIIRCQNISDNTKTII<br>VHLNESVQINCTRPNNNVVESIHLGPGQAFYATRRITGNIRKAYCNIN<br>GTQWNNTLERVKTKLKTYFNKTITFNSASGGDLEVTMHSFNCRGEFF<br>YCNTSELFKNAITPNVTIILQCRIKQIINMWQGVGQAMYASPIAGSITC<br>NSSITGLLLTRDGGNDNVSTEEIFRPGGGNMKDNWRSELYKYKVVKI<br>EPLGVAPTRAKRQVVKRDKRAVGLGAVFLGFLGAAGSTMGAASITL<br>MVQARQLLSGIVQQQNNLLRAIEAQQHMLQLTVWGIKQLQARLLAV<br>ERYLKDQQLLGIWGCSGKLICTTNVPWNSSWSNKSQEEIWGNMTWM<br>EWEKEISNYSSTIYSLIEQSQNQQEKNEQELLALDKWTSLWNWFDISN<br>WLWYIKIFIMIVGGLIGLRIVFAVLSIVNRVRKGYSPLSLQTLIPSPRGP<br>DRPEGIEEGGGEQNRDRSVRLVNGFLALVWDDLRNLCLFSYRHLRDF<br>ILIAARTVDRGLRRGWEALKYLWNLIQYWSRELKNSTTSLLDTTAVV<br>VAEGTDRVIEALQRAGRAVLNVPRRIRQGAERALL (SEQ ID NO: 70) |

In some embodiments, oral antigenic compositions comprise a recombinant *Spirulina*, wherein the recombinant *Spirulina* a comprises at least one exogenous antigenic epitope having a sequence selected from the group consisting of: NANP (SEQ ID NO: 6), NVDP (SEQ ID NO: 7), NPDP (SEQ ID NO: 8), and a combination thereof. In some embodiments, multiple copies of these epitopes can be present in the recombinant *Spirulina* without being linked to any other protein; or as a part of a circumsporozoite protein containing these epitopes; or in the form of a fusion protein comprising one or more of these epitopes. Multiple copies of these epitopes can be present in the recombinant *Spirulina* in a variety of arrangement patterns, e.g., tandem and/or separated by spacer sequences, as described herein.

In some embodiments, oral antigenic compositions comprise a recombinant *Spirulina* comprising at least one antigenic epitope from a tumor antigen. The term "tumor antigen" as used herein refers to an antigen expressed on a cancer cell. In some embodiments, the recombinant *Spirulina* comprises at least one antigenic epitope from a tumor antigen expressed on a cancer cell including but not limited to, breast cancer cell, colon cancer cell, brain cancer cell, pancreatic cancer cell, lung cancer cell, cervical cancer cell, uterine cancer cell, prostate cancer cell, ovarian cancer cell, melanoma cancer cell, lymphoma cancer cell, myeloma cancer cell, and/or leukemic cancer cell.

In some embodiments, oral antigenic compositions comprise a recombinant *Spirulina* comprising at least one antigenic epitope from a self-antigen. The term "self-antigen" as used herein refers to an antigen associated with an autoimmune disease. In some embodiments, the recombinant *Spirulina* comprises at least one antigenic epitope from a self-antigen associated with an autoimmune disease including but not limited to, ulcerative colitis, rheumatoid arthritis, systemic lupus erythematosus (SLE), celiac disease, inflammatory bowel disease, Hashimoto's disease, Addison's disease, Grave's disease, type I diabetes, autoimmune thrombocytopenic purpura (ATP), idiopathic pulmonary fibrosis, idiopathic thrombocytopenia purpura (ITP), Crohn's disease, multiple sclerosis, and myasthenia gravis.

Oral antigenic compositions of the present disclosure comprise recombinant *Spirulina* in a non-living form. These non-living *Spirulina* containing an expressed exogenous antigen or epitope are then administered to a subject to elicit an immune response in the subject. In some embodiments, non-living recombinant *Spirulina* comprising at least one exogenous antigen or at least one exogenous antigenic epitope is prepared by drying the live culture of the recombinant *Spirulina*. Methods of drying include heat drying, e.g., drying in an oven; air-drying, spray drying, lyophilizing, or freeze-drying. Accordingly, in some embodiments, oral antigenic compositions of the present disclosure comprise a dried biomass of a recombinant *Spirulina* comprising at least one exogenous antigen or at least one exogenous antigenic epitope as described herein.

As used herein "*Spirulina*" is synonymous with "*Arthrospira*." Oral antigenic compositions of the present disclosure can comprise any one of the following species of *Spirulina: A. amethystine, A. ardissonei, A. argentina, A. balkrishnanii, A. baryana, A. boryana, A. braunii, A. breviarticulata, A. brevis, A. curta, A. desikacharyiensis, A. funiformis, A. fusiformis, A. ghannae, A. gigantean, A. gomontiana, A. gomontiana* var. *crassa, A. indica, A. jenneri* var. *platensis, A. jenneri Stizenberger, A. jennerif purpurea, A. joshii, A. khannae, A. laxa, A. laxissima, A. laxissima, A. leopoliensis, A. major, A. margaritae, A. massartii, A. massartii* var. *indica, A. maxima, A. meneghiniana, A. miniata* var. *constricta, A. miniata, A. miniata* f. *acutissima, A. neapolitana, A. nordstedtii, A. oceanica, A. okensis, A. pellucida, A. platensis, A. platensis* var. *non-constricta, A. platensis f. granulate, A. platensis* f. *minor, A. platensis* var. *tenuis, A. santannae, A. setchellii, A. skujae, A. spirulinoides* f. *tenuis, A. spirulinoides, A. subsalsa, A. subtilissima, A. tenuis, A. tenuissima*, and *A. versicolor.*

In some embodiments, oral antigenic compositions of the present disclosure can comprise one or more pharmaceutically acceptable excipients. Pharmaceutically acceptable carriers include but are not limited to saline, buffered saline, dextrose, water, glycerol, sterile isotonic aqueous buffer, and combinations thereof. In some embodiments, a pharmaceutically acceptable excipient is sodium bicarbonate.

In some embodiments, oral antigenic compositions of the present disclosure may comprise an adjuvant. As known in the art, the immunogenicity of a particular composition can be enhanced by the use of non-specific stimulators of the immune response, known as adjuvants. Exemplary adjuvants include a water-in-oil (W/O) emulsion composed of a mineral oil and a surfactant from the mannide monooleate family (e.g. MONTANIDE™ class of adjuvants) and flagellin adjuvants.

In some embodiments, oral antigenic compositions of the present disclosure comprise about 0.1% to about 5% of the total *Spirulina* biomass. In some embodiments, oral antigenic compositions of the present disclosure comprise about 1 mg to about 50 mg of the exogenous antigenic epitope per gram of dried *Spirulina* biomass. In some embodiments, oral antigenic compositions of the present disclosure comprise at least about 1 mg, 5 mg, 10 mg, 25 mg, 50 mg, 100 mg, 200 mg, 300 mg, 500 mg, 750 mg, 1 mg, 5 mg, 10 mg, or 50 of the exogenous antigenic epitope per gram of dried *Spirulina* biomass.

Uses of Oral Antigenic Compositions

Oral antigenic compositions of the present disclosure can be used as a vaccine. In some embodiments, oral antigenic compositions can be used to induce an immune response in a subject. For example, oral antigenic compositions can be used to induce an immune response directed to an infectious microorganism, a tumor antigen, or a self-antigen. In some embodiments, oral antigenic compositions can be used to reduce the severity of an infection in a subject in need thereof. In some embodiments, oral antigenic compositions can be used to prevent infection in a subject. In some embodiments, oral antigenic compositions can be used to prevent disease in a subject. In some embodiments, oral antigenic compositions can be used to reduce the severity of a disease in a subject. In some embodiments, oral antigenic compositions can be used to prevent or delay recurrence of a disease in a subject. In some embodiments, oral antigenic compositions can be used to prevent or delay recurrence of a cancer in a subject.

In some embodiments, provided herein are methods of inducing an immune response in a subject in need thereof comprising administering to the subject any of the oral antigenic compositions described herein. Without wishing to be bound to a theory, it is expected that when the oral antigenic composition of the present disclosure is administered to a subject, the at least one exogenous antigenic epitope is recognized by immune cells of the subject, such as T cells or B cells, thereby activating an immune response against the exogenous antigenic epitope. In some embodiments, administration of oral antigenic compositions described herein can induce a humoral immune response and/or a cellular immune response.

Oral antigenic compositions of the present disclosure can be administered according to a schedule, for example, administering a priming dose of the antigenic composition and subsequently administering one or more booster doses of the antigenic composition. In some embodiments, a first booster dose of the antigenic composition can be administered anywhere from about two weeks to about 10 years after the priming dose. In some embodiments, a first booster dose of the antigenic composition can be administered anywhere from about two weeks, 1 month, 2 months, 3 months, 4 months, 6 months, 9 months, 1 year, 2 years, 3 years, or 5 years after the priming dose. A second booster dose of the antigenic composition can be administered after the first booster dose and anywhere from about 3 months to about 10 years after the priming dose. In some embodiments, a second booster dose of the antigenic composition can be administered after the first booster dose and from about 3 months, 4 months, 6 months, 9 months, 1 year, 2 years, 3 years, or 5 years after the priming dose. The third booster dose may be optionally administered when no or low levels of specific immunoglobulins are detected in the serum and/or other bodily fluids of the subject after the second booster dose.

In some embodiments, antigenic compositions other than the oral antigenic compositions of the present disclosure can be administered prior to the administration of the present compositions to prime the subject's immune response. In these embodiments, methods of the present disclosure comprise administering an antigenic composition other than the present oral antigenic composition as a priming dose and subsequently administering one or more booster doses of the present oral antigenic composition.

Oral antigenic compositions of the present disclosure can be used to induce an immune response to and/or prevent or reduce the severity of a disease or an infection caused by a virus, bacterium, parasite, or fungus.

In some embodiments, oral antigenic compositions can be used as a vaccine for, or to induce an immune response to and/or reduce the severity of malaria.

In some embodiments, oral antigenic compositions can be used as a vaccine for, or to induce an immune response to and/or reduce the severity of an infection such as tetanus, diphtheria, pertussis, pneumonia, meningitis, campylobacteriosis, mumps, measles, rubella, polio, flu, hepatitis, chickenpox, malaria, toxoplasmosis, giardiasis, or leishmaniasis.

In some embodiments, oral antigenic compositions described herein can be used to induce an immune response to and/or reduce the severity of an infection caused by a virus including, but not limited to, bacteriophage, RNA bacteriophage (e.g. MS2, AP205, PP7 and Qβ), *Helicobacter pylori*, infectious haematopoietic necrosis virus (IHNV), parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Denge Virus, Rabies Virus, Newcastle Disease Virus, and White Spot Syndrome Virus.

In some embodiments, oral antigenic compositions described herein can be used to induce an immune response to and/or reduce the severity of an infection caused by IHNV.

In some embodiments, oral antigenic compositions described herein can be used to induce an immune response to and/or reduce the severity of an infection caused by a parvovirus, e.g., canine parvovirus.

In some embodiments, oral antigenic compositions described herein can be used to induce an immune response to and/or reduce the severity of an infection caused by a bacterium including, but not limited to, *Mycobacterium, Streptococcus, Staphylococcus, Shigella, Campylobacter, Salmonella, Clostridium, Corynebacterium, Pseudomonas, Neisseria, Listeria, Vibrio, Bordetella*, and *Legionella*.

In some embodiments, oral antigenic compositions described herein can be used to induce an immune response to and/or reduce the severity of an infection caused by a parasite including, but not limited to, *Plasmodium, Trypanosoma, Toxoplasma, Giardia*, and *Leishmania, Cryptosporidium*, helminthic parasites: *Trichuris* spp. (whipworms), *Enterobius* spp. (pinworms), *Ascaris* spp. (roundworms), *Ancylostoma* spp. and *Necator* spp. (hookworms), *Strongyloides* spp. (threadworms), *Dracunculus* spp. (Guinea worms), *Onchocerca* spp. and *Wuchereria* spp. (filarial worms), *Taenia* spp., *Echinococcus* spp., and *Diphyllobothrium* spp. (human and animal cestodes), *Fasciola* spp. (liver flukes) and *Schistosoma* spp. (blood flukes).

In some embodiments, oral antigenic compositions described herein can be used to induce an immune response to and/or reduce the severity of an infection caused by *Plasmodium*. In some embodiments, oral antigenic compositions of the present disclosure can be used to induce an immune response to and/or reduce the severity of an infection caused by a *Plasmodium* selected from the group consisting of: *P. falciparum, P. malariae, P. ovale* and *P. vivax*.

In some embodiments, oral antigenic compositions described herein can be used to induce an immune response to and/or reduce the severity of an infection caused by a fungus including but not limited to *Aspergillus, Candida, Blastomyces, Coccidioides, Cryptococcus*, and *Histoplasma*. In some embodiments, oral antigenic compositions can be used to induce an immune response to and/or reduce the severity of a *Candida albicans* or a *Candida* auris infection.

In some embodiments, oral antigenic compositions described herein can be used to induce an immune response to a tumor antigen. In some embodiments, the oral antigenic compositions can be used to induce an immune response to a tumor antigen expressed on a cancer cell including but not limited to breast cancer cell, colon cancer cell, brain cancer cell, pancreatic cancer cell, lung cancer cell, cervical cancer cell, uterine cancer cell, prostate cancer cell, ovarian cancer cell, melanoma cancer cell, lymphoma cancer cell, myeloma cancer cell, and leukemic cancer cell.

In some embodiments, oral antigenic compositions described herein can be used to induce an immune response to a self-antigen. In some embodiments, the oral antigenic compositions can be used to induce an immune response to a self-antigen associated with an autoimmune disease including but not limited to ulcerative colitis, rheumatoid arthritis, systemic lupus erythematosus (SLE), celiac disease, inflammatory bowel disease, Hashimoto's disease, Addison's disease, Grave's disease, type I diabetes, autoimmune thrombocytopenic purpura (ATP), idiopathic pulmonary fibrosis, idiopathic thrombocytopenia purpura (ITP), Crohn's disease, multiple sclerosis, and myasthenia gravis.

It is understood that antigenic compositions of the present disclosure are administered orally.

The dosage of the oral antigenic composition can be determined readily by the skilled artisan, for example, by first identifying doses effective to elicit a prophylactic or therapeutic immune response, e.g., by measuring the serum titer of specific immunoglobulins or by measuring the inhibitory ratio of antibodies in serum samples, or bodily fluid samples. Said dosages can be determined from animal studies. A non-limiting list of animals used to study the efficacy of vaccines include the guinea pig, hamster, ferrets, chinchilla, mouse and cotton rat. Study animals may not be the natural hosts to infectious agents but can still serve in studies of various aspects of the disease. For example, any of the above animals can be dosed with an oral antigenic composition of the present disclosure, e.g. a recombinant *Spirulina* comprising a VLP comprising *Plasmodium* antigen/antigenic epitope, to partially characterize the immune response induced, and/or to determine if any neutralizing antibodies have been produced.

In addition, human clinical studies can be performed to determine the preferred effective dose for humans by a skilled artisan. Such clinical studies are routine and well known in the art. Effective doses may be extrapolated from dose-response curves derived from in vitro studies, animal studies, and/or clinical studies.

Methods of Making Oral Antigenic Compositions

Provided are methods of making oral antigenic compositions described herein. Methods of making oral antigenic compositions comprise introducing into a *Spirulina* a a nucleic acid sequence encoding the at least one exogenous antigenic epitope. In some embodiments, the nucleic acid sequence encodes for an exogenous antigen comprising the at least one exogenous antigenic epitope. In some embodiments, the nucleic acid sequence encodes for a fusion protein comprising the at least one exogenous antigenic epitope.

In some embodiments, methods of making oral antigenic compositions comprise introducing into a *Spirulina* a nucleic acid sequence comprising a sequence selected from Table 4.

TABLE 4

| Description of the fusion protein | Sequence |
|---|---|
| *P. yoelii* CSP B cell epitope in monomer WHcAg | atggacatagatccctataaagaatttggttcatcttatcagttgttgaattttcttcctttggacttctt tcctgaccttaatgctttggtggacactgctactgccttgtatgaagaagagctaacaggtaggg aacattgctctccgcaccatacagctattagacaagctttagtatgctgggatgaattaactaaatt |

TABLE 4-continued

| Description of the fusion protein | Sequence |
|---|---|
| | gatagcttggatgagctctaacataacttctCAGGGTCCAGGTGCTCCACAA<br>GGACCTGGAGCACCTCAGGGCCCTGGCGCTCCCCAAGGG<br>CCTGGAGCCCCTCAGGGACCCGGTGCACCGCAAGGTCCG<br>GGCGCTCCCCAAGAACCACCTCAACAGCCTCCACAGCAA<br>CCTCCTCAGCAGCCACCACAACAGCCCCCTCAGCAAgaaca<br>agtaagaacaatcatagtaaatcatgtcaatgatacctggggacttaaggtgagacaaagtttat<br>ggtttcatttgtcatgtctcacttttggacaacatacagttcaagaatttttagtaagttttggagtatg<br>gatcagaactccagctccatatagacctcctaatgcacccattctctcgactcttccggaacatac<br>agtcattAATGAAGATAGTTATGTTCCTTCTGCTGAACAAATT<br>TTAGAATTTGAGCAAAAATTAATTAGCGAGGAAGACCTA<br>GAACAAAAACTGATCTCTGAAGAGGATCTGTAA (SEQ ID<br>NO: 46) |
| *P. falciparum* CSP B cell epitope in tandem WHcAg dimer | ATGGACATAGATCCCTATAAAGAATTTGGTTCATCTTATC<br>AGTTGTTGAATTTTCTACCTTTGGACTTCTTTCCTGACCTA<br>AATGCTTTGGTGGACACTGCTACTGCCTTGTATGAAGAAG<br>AGCTAACAGGTCGAGAACATTGCTCTCCGCACCATACAG<br>CTATTAGACAAGCTTTAGTATGCTGGGATGAATTAACTAA<br>ATTGATAGCTTGGATGAGCTCTAACATAACTTCTGAACAA<br>GTAAGAACAATCATAGTAAATCATGTCAATGATACCTGG<br>GGATTAAAGGTGAGACAAAGTTTATGGTTTCATTTGTCAT<br>GTTTGACTTTTGGACAACATACAGTTCAAGAATTTTTAGT<br>AAGTTTTGGAGTATGGATCAGAACTCCAGCTCCATATAG<br>ACCTCCTAATGCACCCATTCTCTCCACTCTTCCCGAACAT<br>ACAGTCATTGGTGGAAGTGGAGGGTCTGGTGGGTCCGGG<br>GGTAGTGGTGGGTCTGATATCGATCCCTACAAAGAATTC<br>GGCAGTTCTTATCAGTTACTAAATTTCCTGCCGCTGGATT<br>TTTTTCCCGATCTGAACGCCTTGGTCGATACTGCCACCGC<br>CTTGTACGAGGAAGAGCTAACCGGGCGAGAGCATTGTAG<br>TCCACATCATACTGCTATCCGCCAGGCTCTGGTCTGCTGG<br>GACGAATTGACCAAGTTAATTGCATGGATGAGCTCCAAT<br>ATTACTAGTgaagagggtAAtGCaAAcCCtAATGCgAACCCgAAc<br>GCtAACCCtAAtGCcAAtCCtAACGCTAAtCCcAAtGCcAAcCCg<br>AATGCaAAcCCaAAtGCgAATCCgAATGCtAAcCCgAAcGCtA<br>AcCCgAATGCgAATCCaAACGCgAAcCCcAAcGCaAATCCgA<br>AtGCaAACCCtAATGCaAAtCCaggtgaagagGAGCAGGTCCGCA<br>CGATCATTGTTAACCACGTCAACGATACCTGGGGCCTAA<br>AGGTTCGCCAATCTTTGTGGTTCCATCTGTCGTGCCTGAC<br>CTTTGGGCAACACACCGTCCAGGAGTTCCTGGTGAGCTTC<br>GGCGTTTGGATCCGCACCCCAGCACCCTACCGCCCGCCA<br>AATGCTCCCATTTTAAGTACCTTGCCCGAACACACCGTGA<br>TTCACCACCATCATCACCACTAA (SEQ ID NO: 47) |
| *P. falciparum* CSP B cell epitope + Salmonella fliC sequences in tandem WHcAg dimer | ATGGACATAGATCCCTATAAAGAATTTGGTTCATCTTATC<br>AGTTGTTGAATTTTCTACCTTTGGACTTCTTTCCTGACCTA<br>AATGCTTTGGTGGACACTGCTACTGCCTTGTATGAAGAAG<br>AGCTAACAGGTCGAGAACATTGCTCTCCGCACCATACAG<br>CTATTAGACAAGCTTTAGTATGCTGGGATGAATTAACTAA<br>ATTGATAGCTTGGATGAGCTCTAACATAACTTCTGAACAA<br>GTAAGAACAATCATAGTAAATCATGTCAATGATACCTGG<br>GGATTAAAGGTGAGACAAAGTTTATGGTTTCATTTGTCAT<br>GTTTGACTTTTGGACAACATACAGTTCAAGAATTTTTAGT<br>AAGTTTTGGAGTATGGATCAGAACTCCAGCTCCATATAG<br>ACCTCCTAATGCACCCATTCTCTCCACTCTTCCCGAACAT<br>ACAGTCATTGGTGGAAGTGGAGGGTCTGGTGGGTCCGGG<br>GGTAGTGGTGGGTCTGATATCGATCCCTACAAAGAATTC<br>GGCAGTTCTTATCAGTTACTAAATTTCCTGCCGCTGGATT<br>TTTTTCCCGATCTGAACGCCTTGGTCGATACTGCCACCGC<br>CTTGTACGAGGAAGAGCTAACCGGGCGAGAGCATTGTAG<br>TCCACATCATACTGCTATCCGCCAGGCTCTGGTCTGCTGG<br>GACGAATTGACCAAGTTAATTGCATGGATGAGCTCCAAT<br>ATTACTAGTgaagagggtGCGCAGGTCATTAACACTAATTCGC<br>TGAGTTTACTAACACAGAATAATCTAAACAAGAGCCAAT<br>CCGCCCTTGGCACGGCGATCGAGCGGCTGAGTTCGGGGC<br>TGCGTATCAATAGTGCCAAAGATGACGCGGCCGGCCAGG<br>CGATTGCAAATCGTTTTACGGCCAATATAAAGGGGCTTAC<br>ACAGGCTTCTCGTAATGCCAACGACGGTATTTCCATTGCC<br>CAAACAACGGAAGGCGCGCTGAATGAAATCAATAATAAT<br>CTGCAGCGGGTCCGGGAGTTAGCGGTGCAGTCTGCCAAC<br>TCAACAAATTCTCAATCAGATCTGGATTCTATCCAGGCAG<br>AAATAACTCAGAGGCTTAATGAAATCGATCGTGTTTCTGG<br>ACAAACCCAGTTTAATGGTGTCAAGGTCCTTGCTCAGGAC<br>AACACCCTGACCATCCAGGTAGGCGCGAACGATGGAGAA<br>ACCATTGATATTGATCTGAAACAGATTAATTCTCAGACTC<br>TAGGTCTTGACACCTTGAATGTGCAGGGTTCTAAtGCaAAc<br>CCtAATGCgAACCCgAAcGCtAACCCtAAtGCcAAtCCtAACGC<br>TAAtCCcAAtGCcAAcCCgAATGCaAAcCCaAAtGCgAATCCgA |

TABLE 4-continued

| Description of the fusion protein | Sequence |
| --- | --- |
| | ATGCtAAcCCgAAcGCtAAcCCgAATGCgAATCCaAACGCgAA<br>cCCcAAcGCaAATCCgAAtGCaAACCCtAATGCaAAtCCaGGTT<br>CTACCACAACCGAGAATCCTCTGCAGAAAATCGATGCTG<br>CTCTCGCGCAAGTGGACACTTTGCGTTCAGATTTGGGAGC<br>TGTGCAAAATCGTTTCAACAGCGCGATTACAAACCTGGG<br>TAACACCGTAAACAATCTGACTAGTGCCCGGAGTCGGAT<br>TGAAGATAGCGATTATGCGACCGAAGTGTCTAACATGAG<br>CCGGGCCCAAATCTTGCAGCAAGCCGGCACTAGTGTTCT<br>GGCGCAAGCAAATCAGGTCCCCCAAAACGTTCTCAGCCT<br>TCTGCGGggtgaagagGAGCAGGTCCGCACGATCATTGTTAA<br>CCACGTCAACGATACCTGGGGCCTAAAGGTTCGCCAATC<br>TTTGTGGTTCCATCTGTCGTGCCTGACCTTTGGGCAACAC<br>ACCGTCCAGGAGTTCCTGGTGAGCTTCGGCGTTTGGATCC<br>GCACCCCAGCACCCTACCGCCCGCCAAATGCTCCCATTTT<br>AAGTACCTTGCCCGAACACACCGTGATTCACCACCATCAT<br>CACCACTAA (SEQ ID NO: 48) |
| Canine parvovirus 2L21 peptide epitope in 2x configuration; monomer WhcAg | ATGGACATAGATCCCTATAAAGAATTTGGTTCATCTTATC<br>AGTTGTTGAATTTTCTACCTTTGGACTTCTTTCCTGACCTA<br>AATGCTTTGGTGGACACTGCTACTGCCTTGTATGAAGAAG<br>AGCTAACAGGTCGAGAACATTGCTCTCCGCACCATACAG<br>CTATTAGACAAGCTTTAGTATGCTGGGATGAATTAACTAA<br>ATTGATAGCTTGGATGAGCTCTAACATAACTTCTgaagagggt<br>TCTGACGGTGCTGTGCAGCCCGATGGCGGTCAACCCGCT<br>GTTCGTAATGAACGTGCTACTGGTGGTGGCTCTAGTGATG<br>GTGCTGTTCAGCCTGACGGTGGTCAACCTGCTGTGCGCAA<br>CGAGCGTGCAACAGGAggtgaagagGAACAAGTAAGAACAA<br>TCATAGTAAATCATGTCAATGATACCTGGGGATTAAAGG<br>TGAGACAAAGTTTATGGTTTCATTTGTCATGTTTGACTTTT<br>GGACAACATACAGTTCAAGAATTTTTAGTAAGTTTTGGAG<br>TATGGATCAGAACTCCAGCTCCATATAGACCTCCTAATGC<br>ACCCATTCTCTCCACTCTTCCCGAACATACAGTCATTCAC<br>CACCATCATCACCACTAA (SEQ ID NO: 49) |
| Canine parvovirus 3L17 peptide epitope in 4x configuration; monomer WhcAg | ATGGACATAGATCCCTATAAAGAATTTGGTTCATCTTATC<br>AGTTGTTGAATTTTCTACCTTTGGACTTCTTTCCTGACCTA<br>AATGCTTTGGTGGACACTGCTACTGCCTTGTATGAAGAAG<br>AGCTAACAGGTCGAGAACATTGCTCTCCGCACCATACAG<br>CTATTAGACAAGCTTTAGTATGCTGGGATGAATTAACTAA<br>ATTGATAGCTTGGATGAGCTCTAACATAACTTCTgaagagggt<br>GACGGTGCTGTGCAGCCCGATGGCGGTCAACCCGCTGTT<br>CGTAATGAACGTGGTGGCTCTGATGGTGCTGTTCAGCCTG<br>ACGGTGGTCAACCTGCTGTGCGCAACGAGCGTGGTGGTT<br>CCGACGGTGCCGTTCAACCCGACGGTGGCCAACCCGCCG<br>TGCGTAATGAGCGCGGTGGTTCTGACGGCGCTGTGCAAC<br>CTGACGGCGGTCAGCCCGCCGTTCGTAACGAGCGTggtgaag<br>agGAACAAGTAAGAACAATCATAGTAAATCATGTCAATGA<br>TACCTGGGGATTAAAGGTGAGACAAAGTTTATGGTTTCAT<br>TTGTCATGTTTGACTTTTGGACAACATACAGTTCAAGAAT<br>TTTTAGTAAGTTTTGGAGTATGGATCAGAACTCCAGCTCC<br>ATATAGACCTCCTAATGCACCCATTCTCTCCACTCTTCCC<br>GAACATACAGTCATTCACCACCATCATCACCACTAA (SEQ<br>ID NO: 50) |
| IHNV vaccine; E1 + E2 epitopes in tandem WHcAg dimer | ATGGACATAGATCCCTATAAAGAATTTGGTTCATCTTATC<br>AGTTGTTGAATTTTCTACCTTTGGACTTCTTTCCTGACCTA<br>AATGCTTTGGTGGACACTGCTACTGCCTTGTATGAAGAAG<br>AGCTAACAGGTCGAGAACATTGCTCTCCGCACCATACAG<br>CTATTAGACAAGCTTTAGTATGCTGGGATGAATTAACTAA<br>ATTGATAGCTTGGATGAGCTCTAACATAACTTCTGAACAA<br>GTAAGAACAATCATAGTAAATCATGTCAATGATACCTGG<br>GGATTAAAGGTGAGACAAAGTTTATGGTTTCATTTGTCAT<br>GTTTGACTTTTGGACAACATACAGTTCAAGAATTTTTAGT<br>AAGTTTTGGAGTATGGATCAGAACTCCAGCTCCATATAG<br>ACCTCCTAATGCACCCATTCTCTCCACTCTTCCCGAACAT<br>ACAGTCATTGGTGGAAGTGGAGGGTCTGGTGGGTCCGGG<br>GGTAGTGGTGGGTCTGATATCGATCCCTACAAAGAATTC<br>GGCAGTTCTTATCAGTTACTAAATTTCCTGCCGCTGGATT<br>TTTTTCCCGATCTGAACGCCTTGGTCGATACTGCCACCGC<br>CTTGTACGAGGAAGAGCTAACCGGGCGAGAGCATTGTAG<br>TCCACATCATACTGCTATCCGCCAGGCTCTGGTCTGCTGG<br>GACGAATTGACCAAGTTAATTGCATGGATGAGCTCCAAT<br>ATTACTAGTCCTGGTGGAAGTGGAGACGATGAAAATCGT<br>GGCTTGATCGCTTATCCTACCAGTATCCGTTCCTTGAGTG<br>TCGGCGGAAGTGGAGGGTCTGATCTGATTAGCGTGGTTT<br>ACAACAGTGGAAGCGAGATCCTGTCGTTTCCTGGTGGAT<br>CAGGGGAGCAGGTCCGCACGATCATTGTTAACCACGTCA |

TABLE 4-continued

| Description of the fusion protein | Sequence |
| --- | --- |
| | ACGATACCTGGGGCCTAAAGGTTCGCCAATCTTTGTGGTT<br>CCATCTGTCGTGCCTGACCTTTGGGCAACACACCGTCCAG<br>GAGTTCCTGGTGAGCTTCGGCGTTTGGATCCGCACCCCAG<br>CACCCTACCGCCCGCCAAATGCTCCCATTTTAAGTACCTT<br>GCCCGAACACACCGTGATTGAGCAAAAATTAATTAGCGA<br>GGAAGACCTAGAACAAAAACTGATCTCTGAAGAGGATCT<br>GTAA (SEQ ID NO: 51) |
| IHNV vaccine; DIII epitope in tandem WHcAg dimer | ATGGACATAGATCCCTATAAAGAATTTGGTTCATCTTATC<br>AGTTGTTGAATTTTCTACCTTTGGACTTCTTTCCTGACCTA<br>AATGCTTTGGTGGACACTGCTACTGCCTTGTATGAAGAAG<br>AGCTAACAGGTCGAGAACATTGCTCTCCGCACCATACAG<br>CTATTAGACAAGCTTTAGTATGCTGGGATGAATTAACTAA<br>ATTGATAGCTTGGATGAGCTCTAACATAACTTCTGAACAA<br>GTAAGAACAATCATAGTAAATCATGTCAATGATACCTGG<br>GGATTAAAGGTGAGACAAAGTTTATGGTTTCATTTGTCAT<br>GTTTGACTTTTGGACAACATACAGTTCAAGAATTTTTAGT<br>AAGTTTTGGAGTATGGATCAGAACTCCAGCTCCATATAG<br>ACCTCCTAATGCACCCATTCTCTCCACTCTTCCCGAACAT<br>ACAGTCATTGGTGGAAGTGGAGGGTCTGGTGGGTCCGGG<br>GGTAGTGGTGGGTCTGATATCGATCCCTACAAAGAATTC<br>GGCAGTTCTTATCAGTTACTAAATTTCCTGCCGCTGGATT<br>TTTTTCCCGATCTGAACGCCTTGGTCGATACTGCCACCGC<br>CTTGTACGAGGAAGAGCTAACCGGGCGAGAGCATTGTAG<br>TCCACATCATACTGCTATCCGCCAGGCTCTGGTCTGCTGG<br>GACGAATTGACCAAGTTAATTGCATGGATGAGCTCCAAT<br>ATTACTAGTCCTGGTGGAAGTGGAgacgatgagaacagggggctaatt<br>gcctatcccacatccatccggtccctgtcagtcggaaacgacGGTGGCAGTGGAG<br>GGTCTagccaagagataaaagctcacctctttgttgataaaatctccaatcgagtcgtgaag<br>gcaacgagctacggacaccaccccctggggactgcatcaggcctgtatgattgaattctgtggg<br>caacagtggatacggacagatctcggtgacctaatatctgtcgtatacaattctggatcagaaat<br>cctctcgttcccgaagtgtgaagacaagaccgtgggaCCAGCAGAGGGTGGCG<br>GTCCAGCAGGTGGATCAGGGGAGCAGGTCCGCACGATCA<br>TTGTTAACCACGTCAACGATACCTGGGGCCTAAAGGTTCG<br>CCAATCTTTGTGGTTCCATCTGTCGTGCCTGACCTTTGGG<br>CAACACACCGTCCAGGAGTTCCTGGTGAGCTTCGGCGTTT<br>GGATCCGCACCCCAGCACCCTACCGCCCGCCAAATGCTC<br>CCATTTTAAGTACCTTGCCCGAACACACCGTGATTGAGCA<br>AAAATTAATTAGCGAGGAAGACCTAGAACAAAAACTGAT<br>CTCTGAAGAGGATCTGTAA (SEQ ID NO: 52) |

Any appropriate means for transforming *Spirulina* may be used in the present disclosure. Exemplary methods for transforming *Spirulina* to express a heterologous protein are described in U.S. Pat. No. 10,131,870, which is incorporated by reference herein in its entirety.

In some embodiments, methods of making an oral antigenic composition comprising introducing an expression vector having a nucleic acid sequence encoding the at least one exogenous antigenic epitope into a *Spirulina* cell. In some embodiments, the vector is not integrated into the *Spirulina* genome. In some embodiments, the vector is a high copy or a high expression vector. In some embodiments the nucleic acid sequence encoding the at least one exogenous antigenic epitope is under the control of a strong promoter. In some embodiments the nucleic acid sequence encoding the at least one exogenous antigenic epitope is under the control of a constitutive promoter. In some embodiments the nucleic acid sequence encoding the at least one exogenous antigenic epitope is under the control of an inducible promoter.

In some embodiments, methods of making an oral antigenic composition comprise introducing a vector having homology arms and a nucleic acid sequence encoding the at least one exogenous antigenic epitope into a *Spirulina* cell. Upon homologous recombination, the nucleic acid sequence encoding the at least one exogenous antigenic epitope is integrated into the *Spirulina* genome.

In some embodiments, a vector having homology arms and a nucleic acid sequence encoding the at least one exogenous antigenic epitope can be introduced into *Spirulina* using electroporation. The electroporation is preferably carried out in the presence of an appropriate osmotic stabilizer.

Prior to introduction of the vector into *Spirulina, Spirulina* may be cultured in any suitable media for growth of cyanobacteria such as SOT medium. SOT medium includes $NaHCO_3$ 1.68 g, $K_2HPO_4$ 50 mg, $NaNO_3$ 250 mg, $K_2 5 0_4$ 100 mg, NaCl 100 mg, $MgSO_4 \cdot 7H_2O$, 20 mg, $CaCl_2 \cdot 2H_2O$ 4 mg, $FeSO_4 \cdot 7H_2O$ 1 mg, $Na_2EDTA \cdot 2H_2O$ 8 mg, $A_5$ solution 0.1 mL, and distilled water 99.9 mL. $A_5$ solution includes $H_3BO_3$ 286 mg, $MnSO_4 \cdot 5H_2O$) 217 mg, $ZnSO_4 \cdot 7H_2O$ 22.2 mg, $CuSO_4 \cdot 5H_2O$ 7.9 mg, $Na2MoO_4 \cdot 2H_2O$ 2.1 mg, and distilled water 100 mL. Cultivation may occur with shaking (e.g., 100-300 rpm) at a temperature higher than room temperature (e.g. 25-37° C.) and under continuous illumination (e.g. 20-2,000, 50-500, or 100-200 mol photon $m^{-2}$ $s^{-1}$). The growing cells may be harvested when the optical density at 750 nm reaches a predetermined threshold (e.g., $OD_{750}$ of 0.3-2.0, 0.5-1.0, or 0.6-0.8). A volume of the harvested cells may be concentrated by centrifugation then resuspended in a solution of pH balancer and salt. The pH balancer may be any suitable buffer that maintains viability of *Spirulina* while keeping pH of the media between 6 and 9 pH, between 6.5 and 8.5 pH, or between 7 and 8 pH. Suitable pH balancers include HEPES, HEPES-NaOH, sodium or potassium phosphate buffer, and TES. The salt solution may be NaCl at a concentration of between 50 mM and 500 mM, between 100 mM and 400 mM, or between 200 mM and 300 mM. In an embodiment between 1-50 mL of 1-100 mM pH balance may be used to neutralize the pH.

Cells collected by centrifugation may be washed with an osmotic stabilizer and optionally a salt solution (e.g. 1-50 mL of 0.1-100 mM NaCl). Any amount of the culture may be concentrated by centrifugation. In an embodiment between 5-500 mL of the culture may be centrifuged. The osmotic stabilizer may be any type of osmotic balancer that stabilizes cell integrity of *Spirulina* during electroporation. In an embodiment, the osmotic stabilizer may be a sugar (e.g. w/v 0.1-25%) such as glucose or sucrose. In an embodiment the osmotic stabilizer may be a simple polyol (e.g. v/v 1-25%) including glycerine, glycerin, or glycerol. In an embodiment the osmotic stabilizer may be a polyether including (e.g. w/v 0.1-20%) polyethylene glycol (PEG), poly(oxyethylene), or poly(ethylene oxide) (PEO). The PEG or PEO may have any molecular weight from 200 to 10,000, from 1000 to 6000, or from 2000 to 4000. In an embodiment the pH balancer or buffer may be used instead of or in addition to the osmotic stabilizer.

A vector having homology arms and a nucleic acid sequence encoding the at least one exogenous antigenic epitope can be introduced into *Spirulina* cells that are cultured and washed with an osmotic stabilizer as described above. Electroporation can be used to introduce the vector.

Electroporation may be performed in a 0.1-, 0.2- or 0.4-cm electroporation cuvette at between 0.6 and 10 kV/cm, between 2.5 and 6.5 kV/cm, or between 4.0 and 5.0 kV/cm; between 1 and 100 μF, between 30 and 70 μF, or between 45 and 55 μF; and between 10 and 500 mΩ, between 50 and 250 mΩ, or between 90 and 110 mΩ. In some embodiments, electroporation may be performed at 4.5 kV/cm, 50 f, and 100 mΩ.

Following electroporation the cells may be grown in the presence of one or more antibiotics selected based on resistance conferred through successful transformation with the plasmid. Post-electroporation culturing may be performed at reduced illumination levels (e.g. 5-500, 10-100, or 30-60 mol photon $m^{-2}$ $s^{-1}$). The culturing may also be performed with shaking (e.g. 100-300 rpm). The level of antibiotics in the media may be between 5 and 100 g/mL. Post-electroporation culturing may be continued for 1-5 days or longer. Successful transformants identified by antibiotic resistance may be selected over a time course of 1 week to 1 month on plates or in 5-100 mL of SOT medium supplemented with 0.1-2.0 g of appropriate antibiotics.

A vector used in the methods can be a plasmid, bacteriophage, or a viral vector into which a nucleic acid sequence encoding the at least one exogenous antigen can be inserted or cloned. A vector may comprise one or more specific sequences that allow recombination into a particular, desired site of the *Spirulina*'s chromosome. These specific sequences may be homologous to sequences present in the wild-type *Spirulina*. A vector system can comprise a single vector or plasmid, two or more vectors or plasmids, some of which increase the efficiency of targeted mutagenesis, or a transposition. The choice of the vector will typically depend on the compatibility of the vector with the *Spirulina* cell into which the vector is to be introduced. The vector can include a reporter gene, such as a green fluorescent protein (GFP), which can be either fused in frame to one or more of the encoded antigenic epitopes, or expressed separately. The vector can also include a positive selection marker such as an antibiotic resistance gene that can be used for selection of suitable transformants. The vector can also include a negative selection marker such as the type II thioesterase (tesA) gene or the *Bacillus subtilis* structural gene (sacB). Use of a reporter or marker allows for identification of those cells that have been successfully transformed with the vector.

In some embodiments, the vector includes one or two homology arms that are homologous to DNA sequences of the *Spirulina* genome that are adjacent to the targeted locus. The sequence of the homology arms can be partially or fully complementary to the regions of *Spirulina* genome adjacent to the targeted locus.

The homology arms can be of any length that allows for site-specific homologous recombination. A homology arm may be any length between about 2000 bp and 500 bp. For example, a homology arm may be about 2000 bp, about 1500 bp, about 1000 bp, or about 500 bp. In some embodiments having two homology arms, the homology arms may be the same or different length. Thus, each of the two homology arms may be any length between about 2000 bp and 500 bp. For example, each of the two homology arms may be about 2000 bp, about 1500 bp, about 1000 bp, or about 500 bp.

A portion of the vector adjacent to one homology arm or flanked by two homology arms modifies the targeted locus in the *Spirulina* genome by homologous recombination. The modification may change a length of the targeted locus including a deletion of nucleotides or addition of nucleotides. The addition or deletion may be of any length. The modification may also change a sequence of the nucleotides in the targeted locus without changing the length. The targeted locus may be any portion of the *Spirulina* genome including coding regions, non-coding regions, and regulatory sequences.

EXAMPLES

Figure 1C:
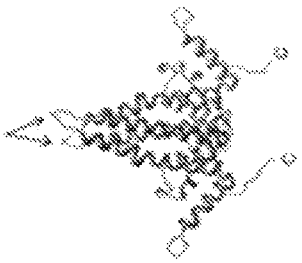
FIG. 1C shows a ribbon diagram of a WHcAg homodimer showing the spike (arrows) formed by the Major Insertion Region (MIR).
Figure 1B:
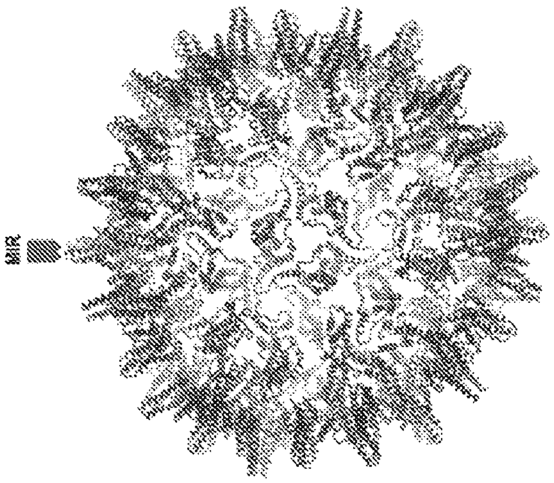
FIG. 1B shows a homodimer of WHcAg assembled into a virus-like particle (VLP).

Example 1: *Spirulina* Engineered to Express WHcAg VLPS with *Plasmodium* CSP Antigens A DNA construct comprising a sequence encoding a homodimeric woodchuck hepadnavirus core antigen (WHcAg) fusion protein containing tandem repeats of *P. yoelii* circumsporozoite protein (CSP) B cell epitopes, and a CSP T cell epitope at the C-terminus followed by tandem myc tags was synthesized. FIG. 1A shows a schematic of the construct. As shown in the schematic, tandem repeats of *P. yoelii* CSP B cell epitopes were inserted at the Major Insertion Region (MIR), which is the region between the amino acid residues S78 and E79 of the WHcAg. The CSP T cell epitope was added at the C-terminus of WHcAg followed by tandem myc tags. FIG. 1I shows the sequence of the construct. The DNA construct encoding the above-described WHcAg fusion protein was introduced into *Spirulina* using a homologous recombination method. WHcAg homodimers assemble into VLPs of 90 or 120 units (FIG. 1B) and form a 'spike' containing the MIR (FIG. 1C) where the CSP B cell epitopes were inserted (arrows). The recombinant *Spirulina* expressing the construct was cultivated.

Figure 1D:
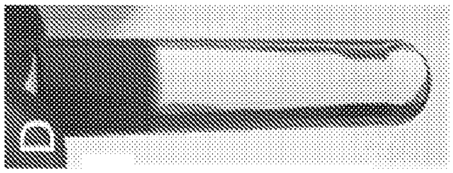
FIG. 1D shows a sonicated recombinant *Spirulina* culture comprising the fusion protein described in Example 1 before discontinuous sucrose density ultracentrifugation.
Figure 1E:
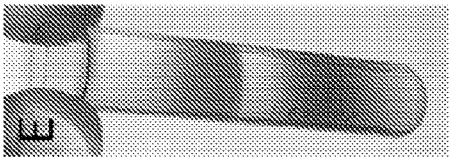
FIG. 1E shows a sonicated recombinant *Spirulina* culture comprising the fusion protein described in Example 1 after discontinuous sucrose density ultracentrifugation.
Figure 1F:
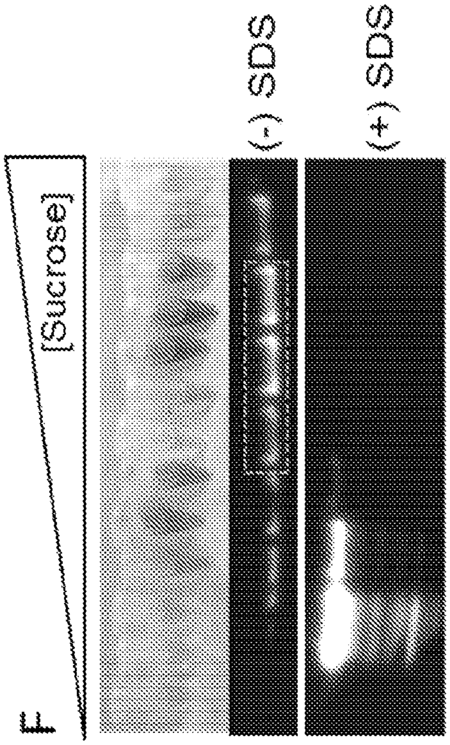
FIG. 1F shows the bottom fractions collected after discontinuous sucrose density ultracentrifugation of a sonicated recombinant *Spirulina* culture and resolved by native polyacrylamide gel electrophoresis (PAGE) or SDS-PAGE.
Figure 1G:
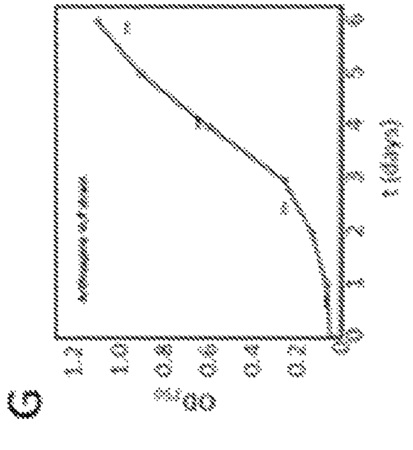
FIG. 1G shows a growth curve for a recombinant *Spirulina* culture described in Example 1.
Figure 1H:
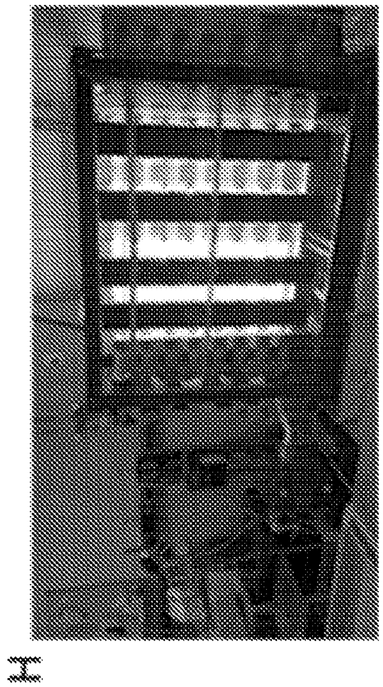
FIG. 1H shows a scale-up to small pilot scale (100 liters) using Fence-type bioreactor with full spectrum LED lighting, illuminated glass tubing, $O_2$ scrubbing and $CO_2$ injection.
Figure 1I:
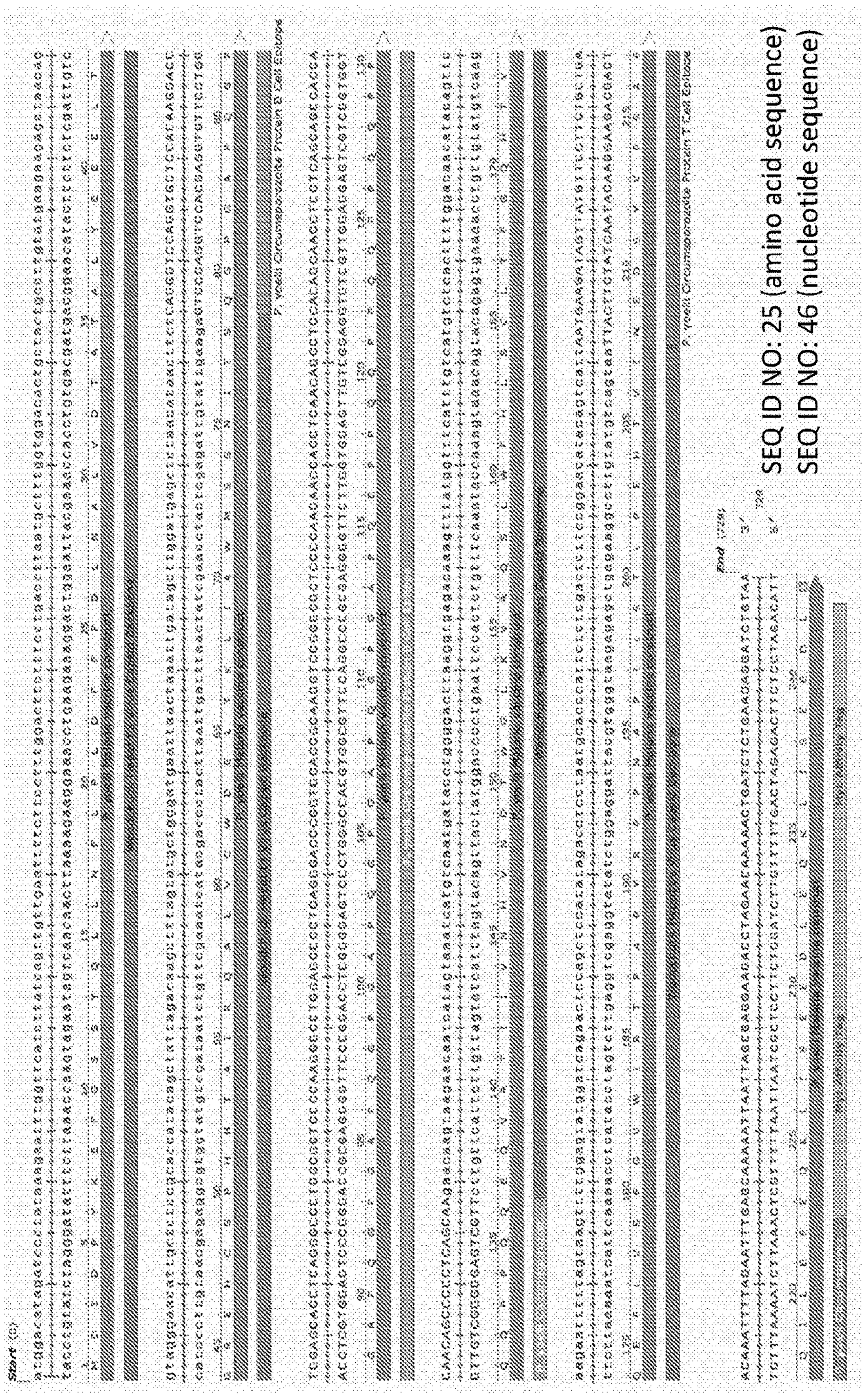
FIG. 1I shows an amino acid sequence of the fusion protein shown in FIG. 1A and the corresponding nucleotide sequence.

The *Spirulina* culture was sonicated and subjected to bioanalytical discontinuous sucrose density ultracentrifugation and fractionation (FIGS. 1D-F). Sonicated *Spirulina* culture before (FIG. 1D) and after (FIG. 1E) bioanalytical discontinuous sucrose density ultracentrifugation. After the centrifugation, the culture showed an orange carotenoid fraction (near the rim of the test tube), a blue phycocyanin fraction (in the middle) and a green chlorophyll pigments fraction (in the lower half of the test tube) with bottom drop fractions resolved by SDS-PAGE and Western blotted using anti-myc-HRP (FIG. 1F). Detergent-free CSP-containing VLPs sediment at 60% sucrose (dashed box) and are abolished by SDS pre-treatment. These VLPs could be detected by spz hyperimmune sera (not shown). Recombinant *Spirulina* grew with wild-type growth kinetics (FIG. 1G). The process is scalable from the 1.5 L scale used here to 200 L scale using Lumen Bioscience's culture facilities (FIG. 1H).

Example 2: Oral *Spirulina* Vaccination Induces Protective Anti-CSP IgG

Figure 2:
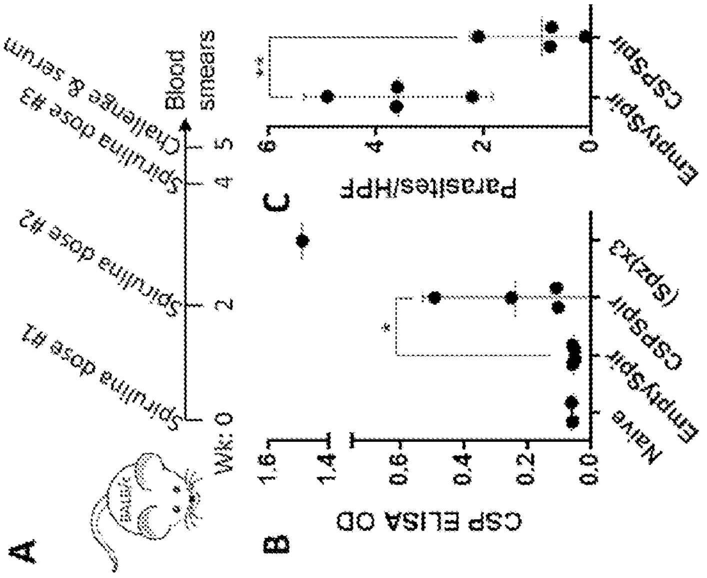
FIG. 2 shows a schematic of the experimental design (panel A); a graph summarizing the results of a CSP-ELISA assay (panel B); and a graph summarizing the results for a Day 5 blood smear data showing mean parasites per high powered field (panel C).

Naïve BALB/cj mice were vaccinated at 0, 2 and 4 weeks by oral gavage with 200 L of a slurry containing 10 mg of lyophilized whole *Spirulina* biomass carrying 40 g of the repeat domain of PyCSP in WHcAg VLPs described in Example 1 or empty WHcAg VLPs with Montanide IMS 1313 VG adjuvant in 0.2 M sodium bicarbonate. FIG. 2A shows the timeline for the experiment. Serum was collected at baseline and before each dose. One week after the third dose, serum was collected and mice intravenously (i.v.) challenged with 125 purified wild-type *P. yoelii* spz. Mice were followed post-challenge by thin blood smears for blood stage infection. A CSP ELISA assay was carried out on the serum. FIG. 2B shows the CSP ELISA data showing optical densities (OD) for serum from naïve mice or those immunized 3× with *Spirulina* carrying empty VLPs, *Spirulina* carrying CSP VLPs or attenuated spz. Half of *Spirulina* CSP-immunized mice seroconverted (FIG. 2B). FIG. 2C shows the Day 5 blood smear data showing mean parasites per high powered field; 50 HPF per mouse; *$p<0.05$; $p<0.01$ (t-tests). CSP-immunized mice had lower onset parasite densities than control mice, indicating partial liver stage protection (FIG. 2**C). *Spirulina*-primed antibodies were predominantly IgG (data not shown). These data is promising for two reasons. First, IgG was induced using an inert algae-based oral vaccine. Second, partial protection was observed despite using an i.v. challenge route that bypasses the opportunity for CSP-specific antibodies to block spz invasion of dermal blood vessels. Thus, this vaccination could be even more effective against intradermal or mosquito bite challenge.

Figure 3:
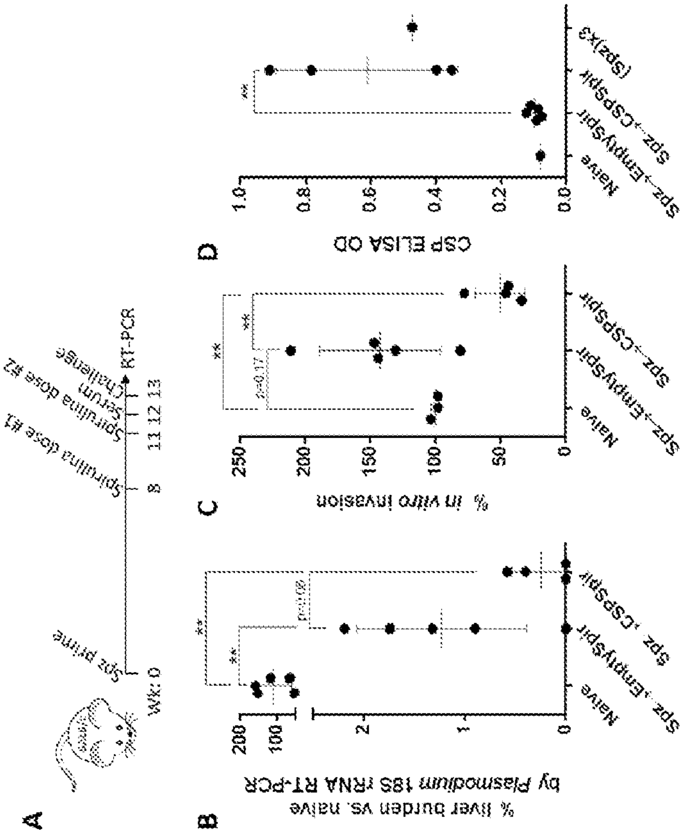
FIG. 3 shows a schematic of the experimental design (panel A); a graph summarizing results of liver burden as assessed by *Plasmodium* 18S rRNA RT-PCR (panel B); a graph summarizing results of an in vitro inhibition of spz invasion (ISI) assay; and a graph summarizing results of a CSP-ELISA assay (panel D).
Figure 4A:
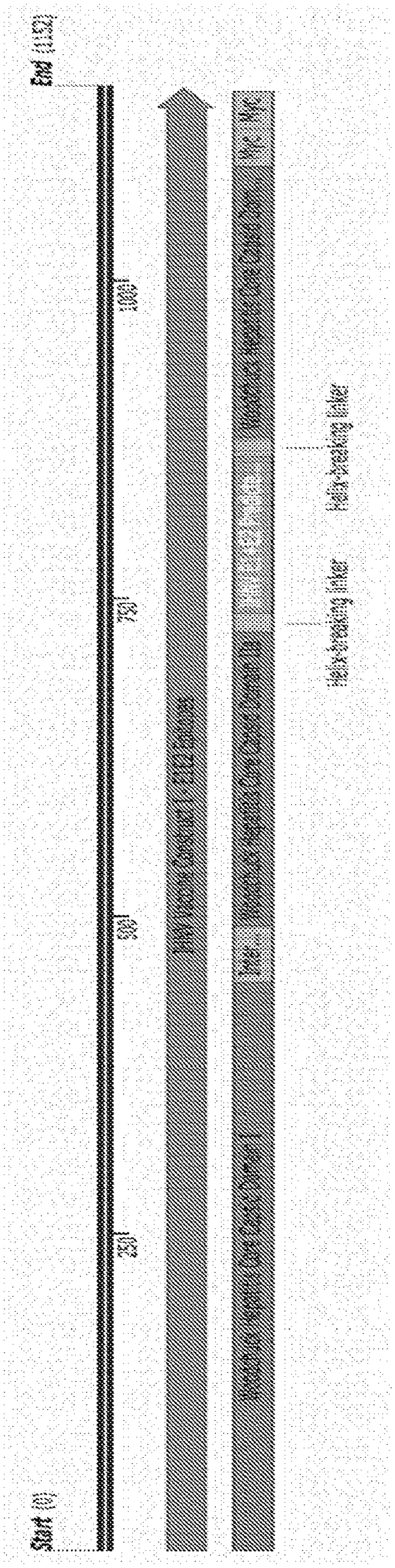
FIG. 4A shows a schematic of the fusion protein comprising WHcAg domains and E1E2 epitopes from infectious haematopoietic necrosis virus (IHNV).
Figure 4B:
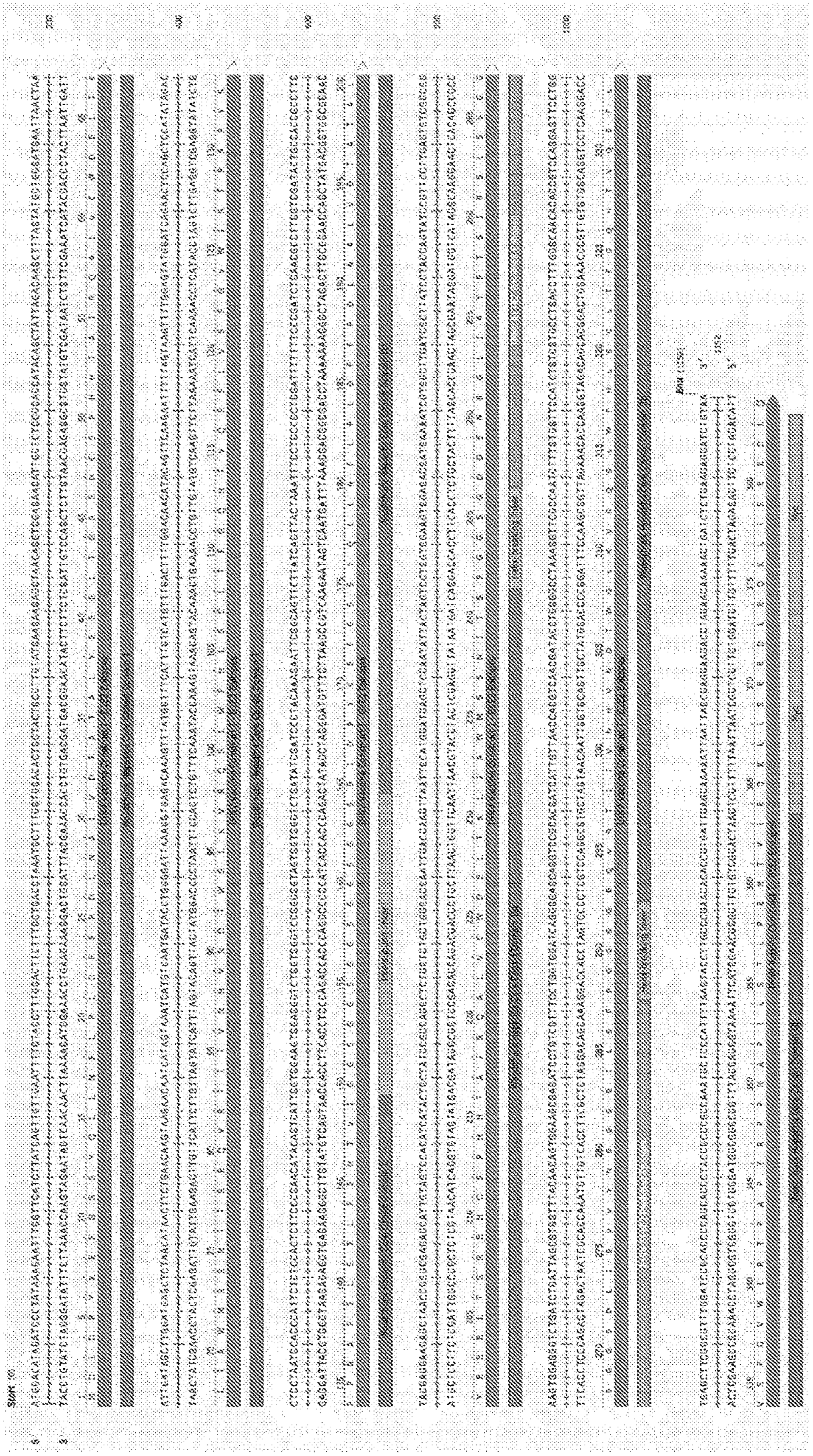
FIG. 4B shows an amino acid sequence of the fusion protein shown in FIG. 4A and the corresponding nucleotide sequence.
Figure 4C:
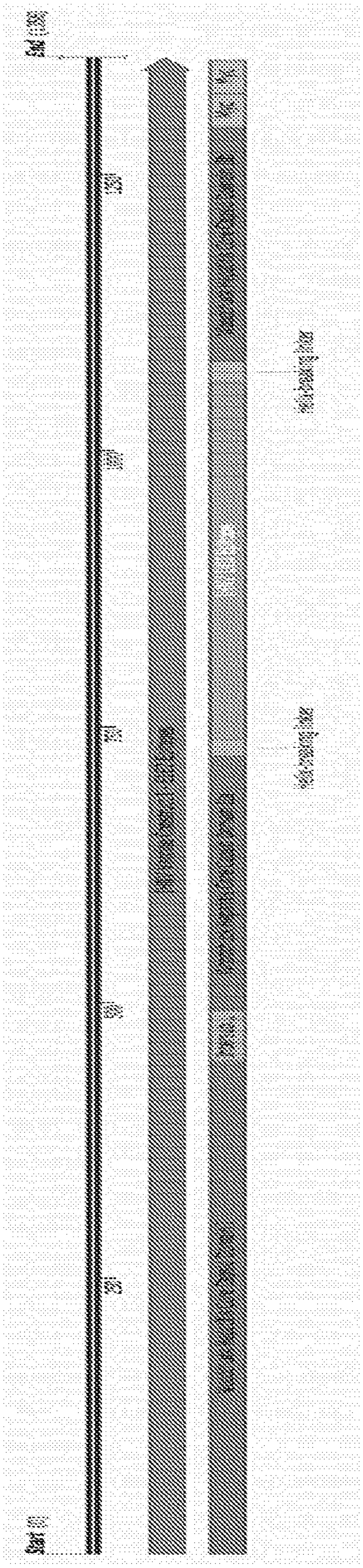
FIG. 4C shows a schematic of the fusion protein comprising WHcAg domains and DIII epitopes from IHNV.

Since the seroconversion was not obtained in all *Spirulina* CSP VLP-immunized mice, a second experiment was performed to examine *Spirulina*-mediated boosting of spz-primed CSP-specific antibodies (FIG. 3A). BALB/cj mice were primed with $2\times10^4$ purified irradiated *P. yoelii* spz and orally vaccinated with CSP- or empty *Spirulina* VLPs 8 and 11 wks later. Serum was collected throughout. Two weeks after the final *Spirulina* booster, mice (including a group of naïve infectivity control mice) were challenged i.v. with $2\times10^4$ purified wild-type *P. yoelii* spz and protection was assessed two days later by liver RT-PCR for *Plasmodium* 18S rRNA. Compared to naïve mice, all spz-primed mice showed substantial reductions in liver burden as expected (FIG. 3B). Mice boosted with *Spirulina* CSP VLPs contained 6.3-fold less *Plasmodium* 18S rRNA than control VLP-boosted mice ($p=0.06$) and two mice showed undetectable *Plasmodium* 18S rRNA (the "RT-PCR equivalent" of sterile protection). In addition, serum from one week after the final booster dose showed potent activity in in vitro inhibition of spz invasion (ISI) assays (FIG. 3C) that was comparable to that seen in mice that can be protected against mosquito-bite challenge (data not shown) although such studies were not performed in our proof-of-concept work. CSP-specific titers were significantly increased in all spz-primed/*Spirulina* CSP VLP-boosted mice compared to spz-primed/*Spirulina* or control *Spirulina*-boosted mice and were comparable to CSP titers achieved in mice repeatedly exposed to attenuated spz (FIG. 3D). As above, the boosted CSP-specific antibodies included IgG (not shown).

Example 3: *Spirulina* Vaccine Comprising Canine Parvovirus Epitopes Induces Immune Response in Mice

Figure 5A:
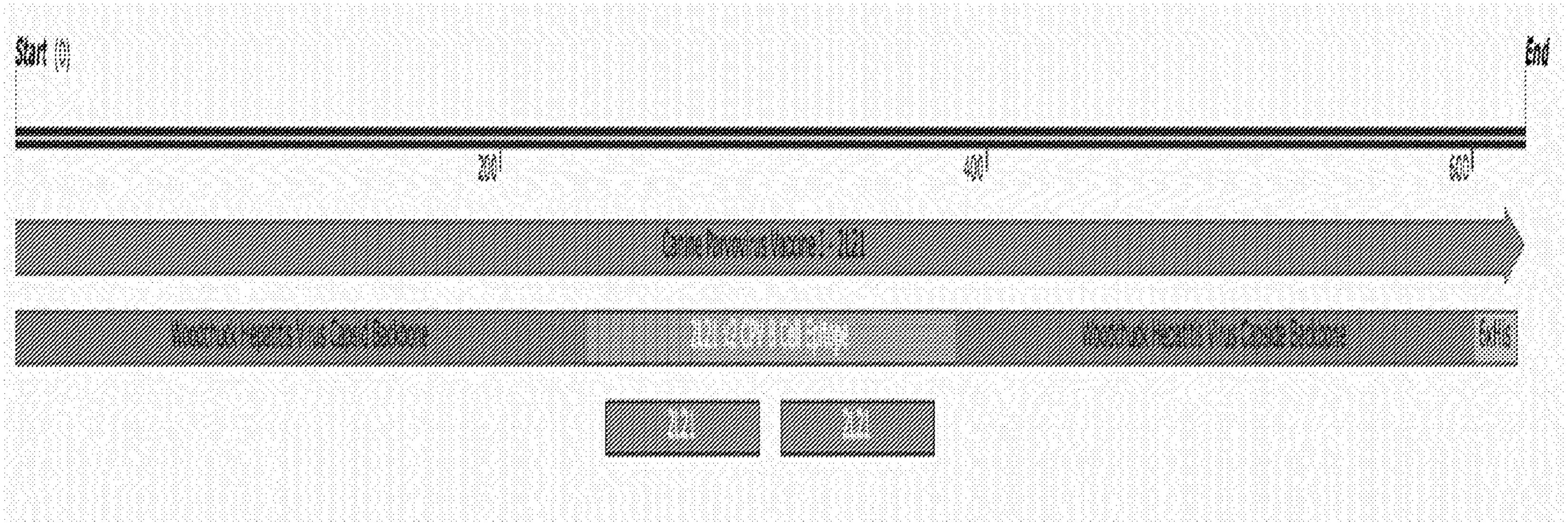
FIG. 5A shows a schematic of the fusion protein comprising WHcAg and 2L21 B cell epitopes from canine parvovirus.
Figure 5B:
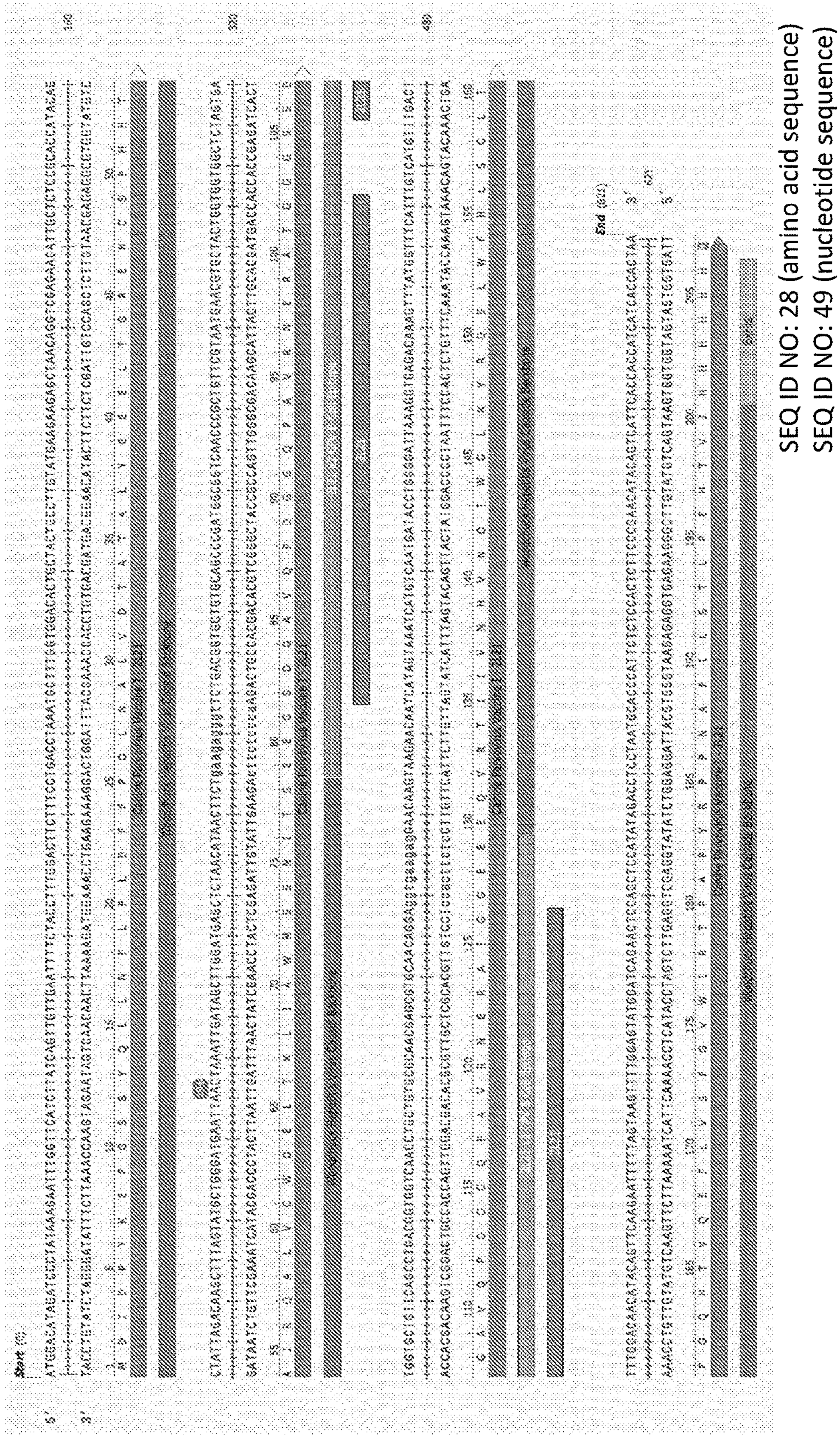
FIG. 5B shows an amino acid sequence of the fusion protein shown in FIG. 5A and the corresponding nucleotide sequence.
Figure 6A:
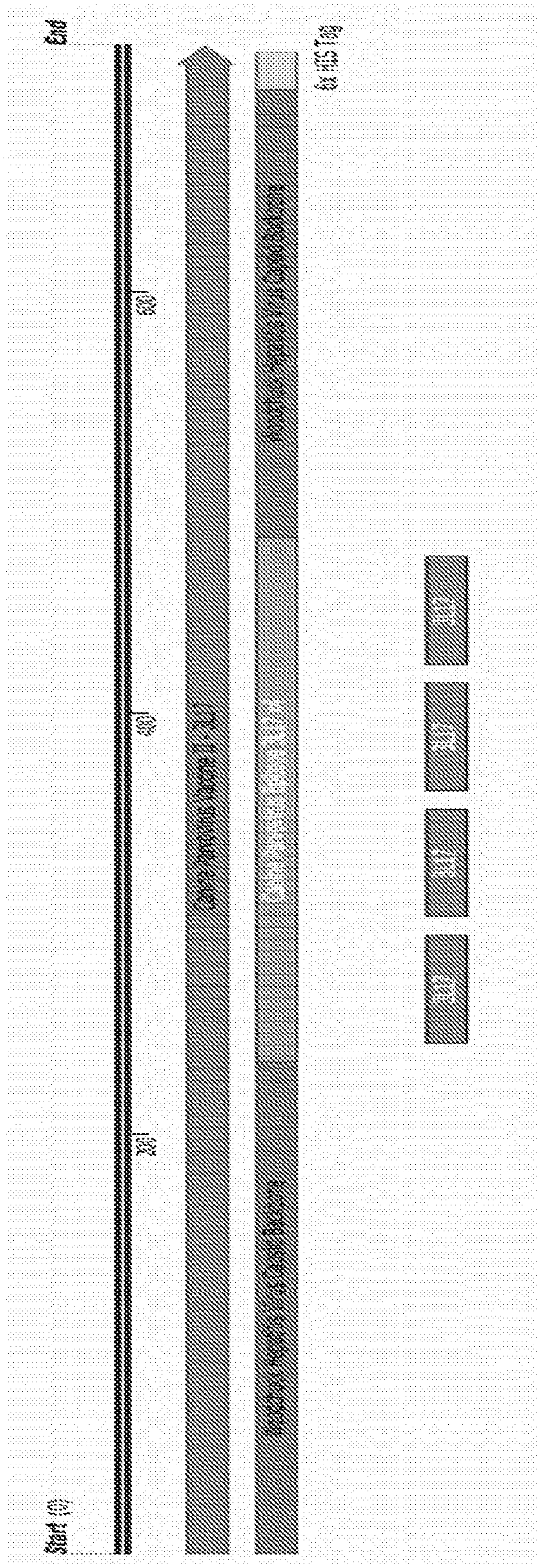
FIG. 6A shows a schematic of the fusion protein comprising WHcAg and 3L17 epitopes from canine parvovirus.
Figure 6B:
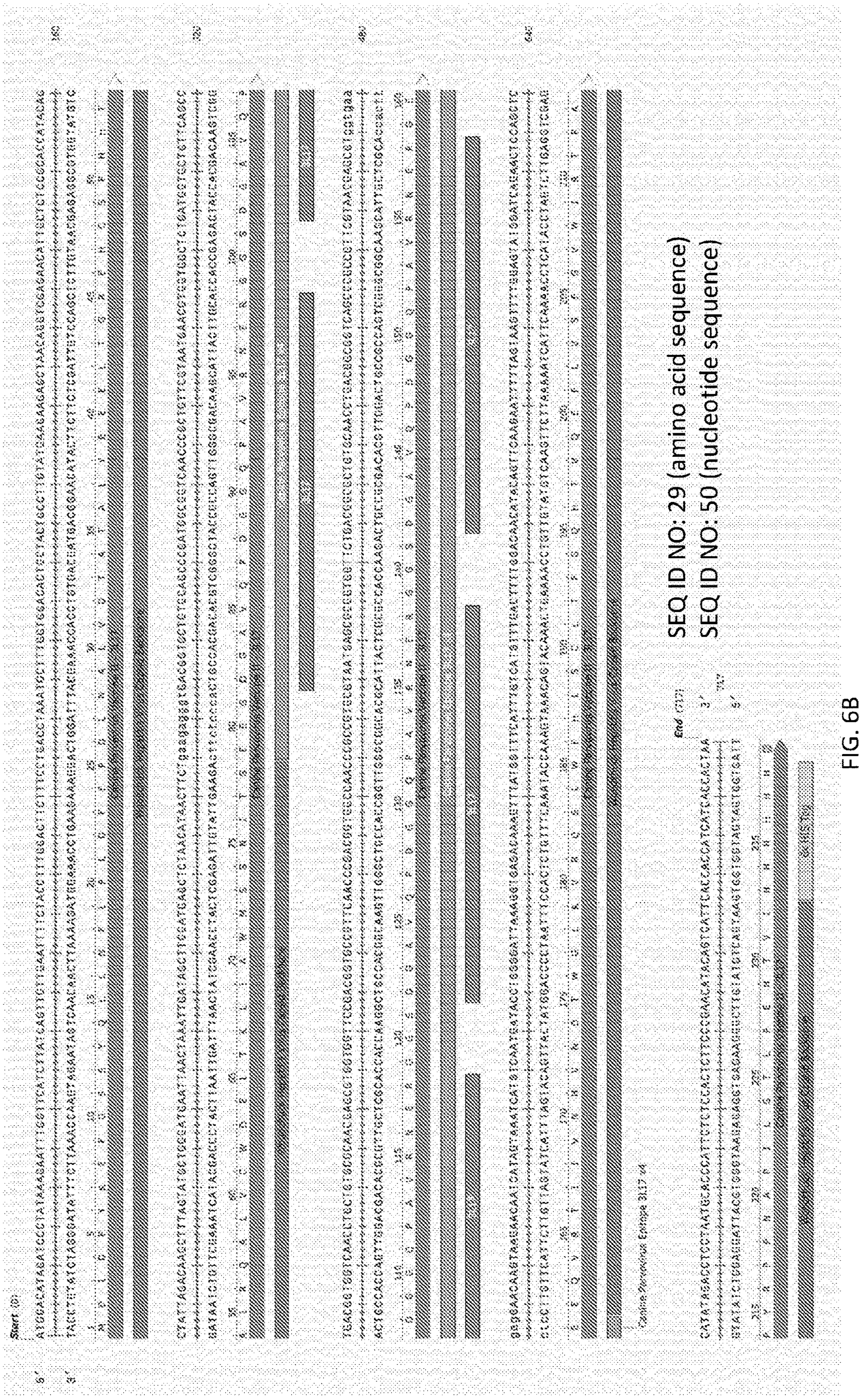
FIG. 6B shows an amino acid sequence of the fusion protein shown in FIG. 6A and the corresponding nucleotide sequence.
Figure 7:
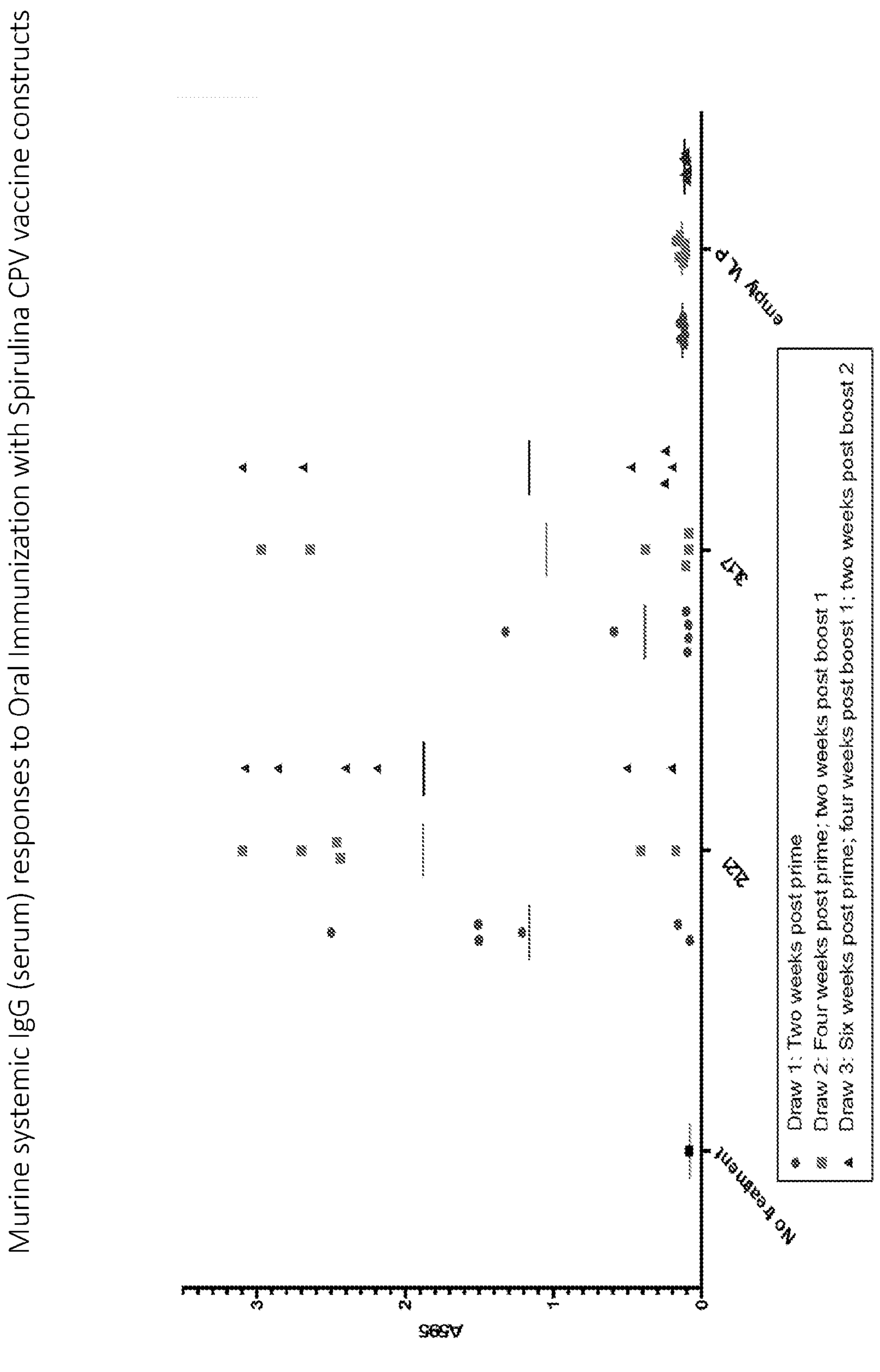
FIG. 7 shows a graph summarizing the results of a systemic IgG response to oral immunization of mice with recombinant *Spirulina* comprising the fusion proteins shown in FIGS. 5A and 6A.

*Spirulina* were transformed with a vector comprising WHcAg and 2L21 B cell epitopes or WHcAg and 3L17 canine parovivirus epitopes. See FIGS. 5 and 6. Mice were orally vaccinated with a recombinant *Spirulina* slurry as taught in Example 2. Blood was drawn and tested for the presence of anti-canine parvovirus antibodies in the serum at two weeks post-priming (Draw 1); four weeks post-priming (Draw 2); and six weeks post-priming (Draw 3). FIG. 7 shows the murine systemic IgG responses to these *Spirulina* CPV vaccine constructs. Both constructs containing canine parvoviruses induced the production of serum IgG antibodies. No serum IgG antibodies were detected in either the "no treatment" or "empty VLP" groups.

Example 4: *Spirulina* Vaccine Comprising *Plasmodium falciparum*: Epitopes Induces Immune Response in Mice

Figure 8A:
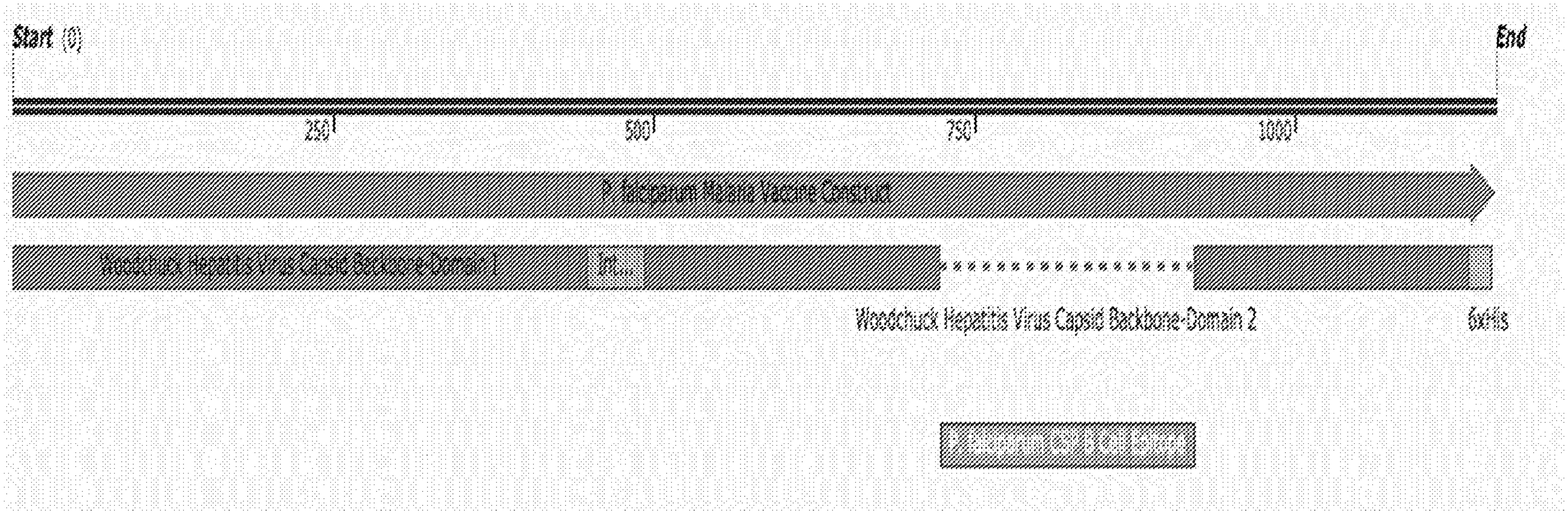
FIG. 8A shows a schematic of the fusion protein comprising WHcAg domains and CSP B cell epitopes from *Plasmodium falciparum.*
Figure 8B:
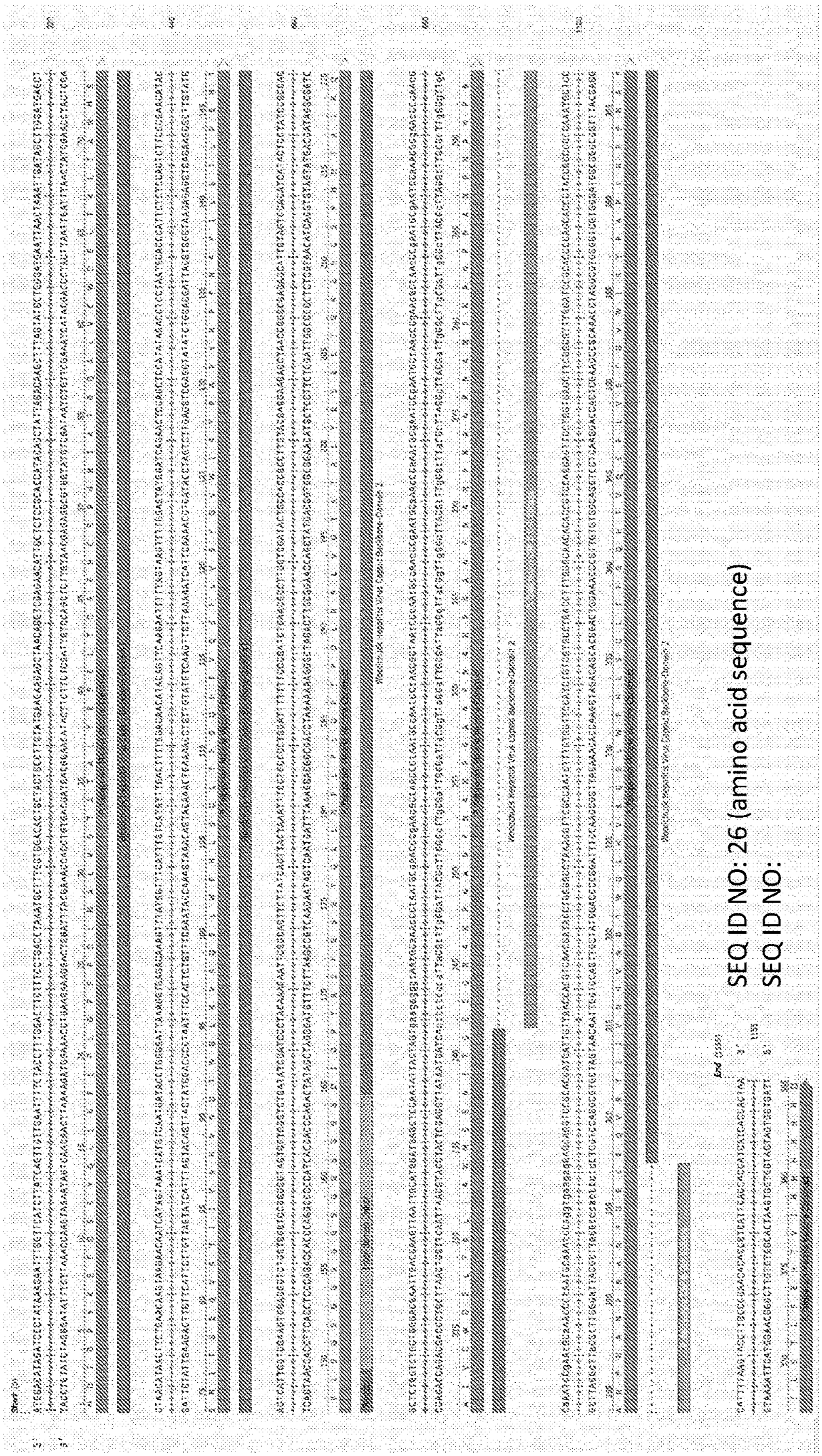
FIG. 8B shows an amino acid sequence of the fusion protein shown in FIG. 8A and the corresponding nucleotide sequence.
Figure 9:
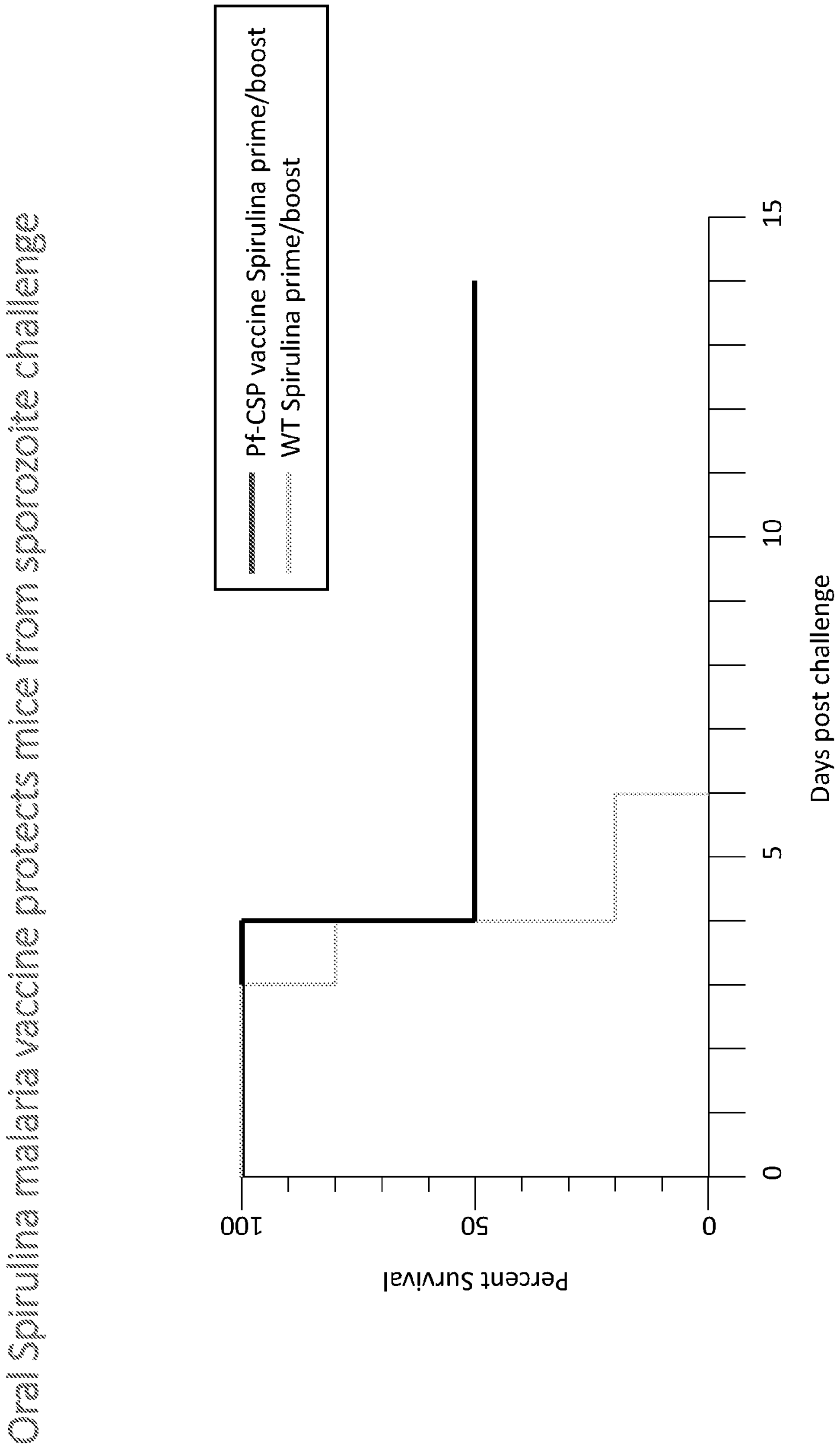
FIG. 9. shows murine survival after immunization with *P. falciparum* CSP *Spirulina* vaccine and subsequent sporozoite challenge.
Figure 10:
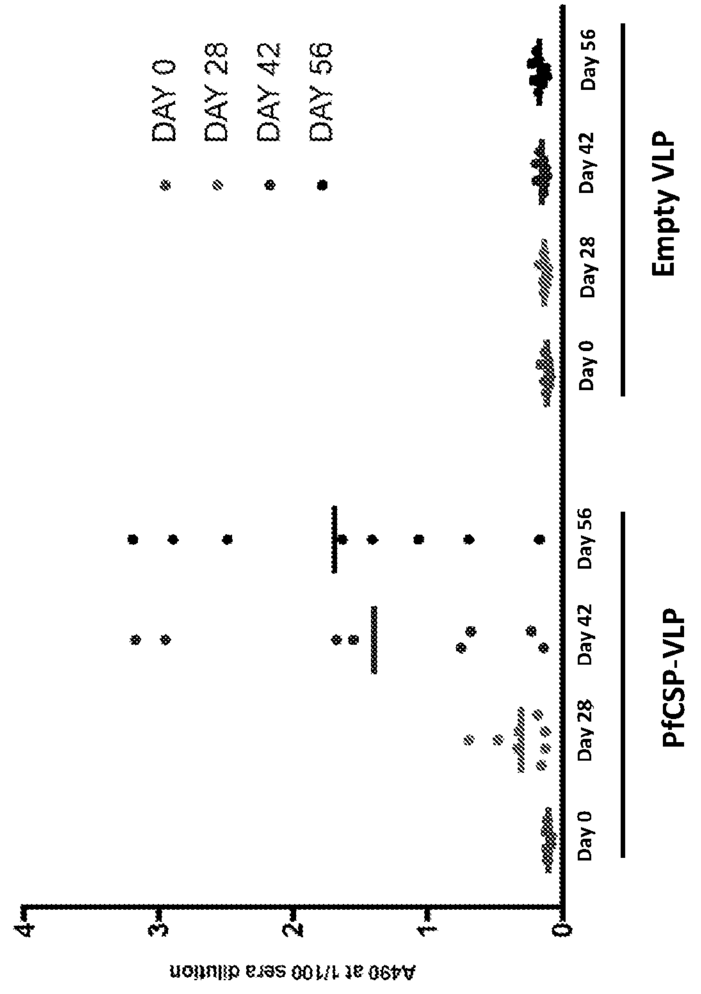
FIG. 10 shows a graph summarizing the results of an IgG response in mice, orally-dosed with *Spirulina* containing WHcAg nanoparticles with *P. falciparum* (NANPx) epitopes (PfCSP-VLP) and control mice orally dosed with *Spirulina* containing WHcAg nanoparticles without *P. falciparum* epitopes (empty VLP).
Figure 11:
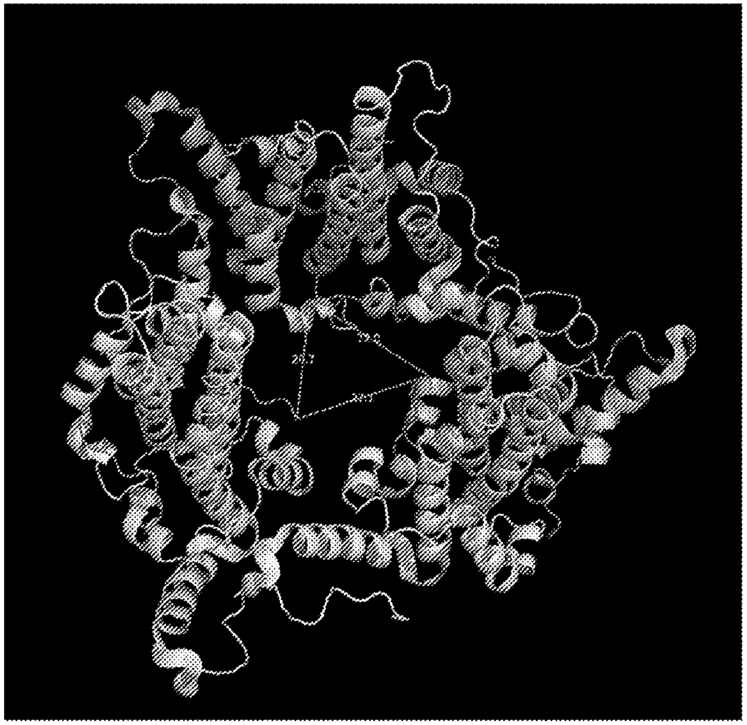
FIG. 11 shows a ribbon diagram of a human HepB core trimer of dimers.
Figure 12:
FIG. 12 shows a ribbon diagram showing a "canyon" from C-term to spike.
Figure 13:
FIG. 13 shows a ribbon diagram showing a "canyon" exit.
Figure 17:
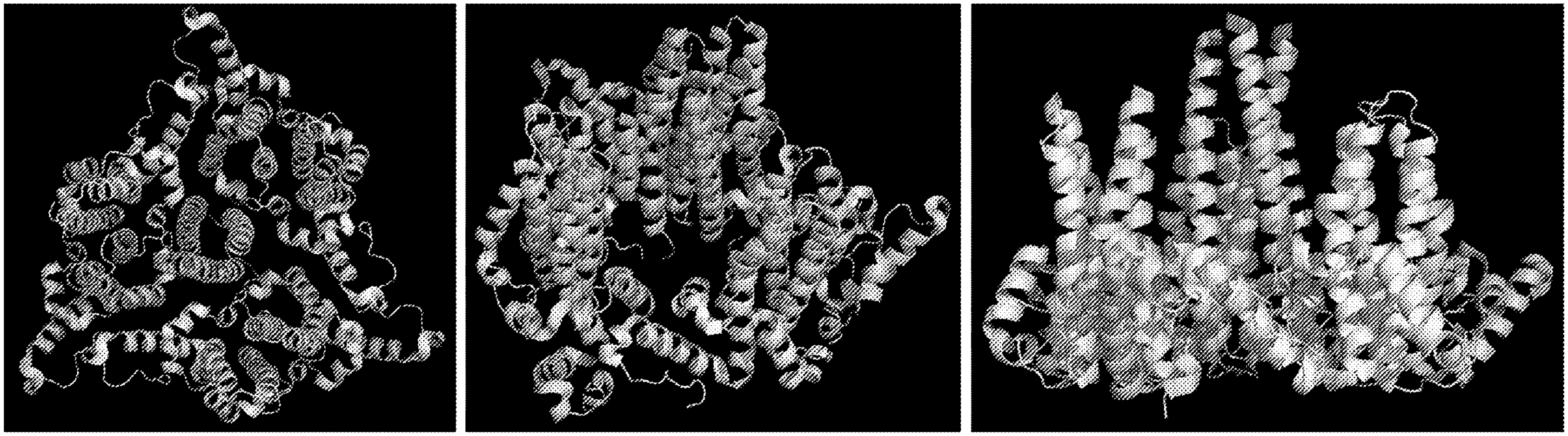
FIG. 17 shows a ribbon diagram of Juxtaposing GCN4-pII trimerization coiled-coil domain onto the Hepatitis B core protein VLP.

*Spirulina* were transformed with a vector comprising a nucleic acid sequence encoding a fusion protein comprising WHcAg domains and CSP B cell epitopes from *Plasmodium falciparum*. See FIG. 8. Mice were orally vaccinated with a wild type *Spirulina* or a recombinant *Spirulina* slurry as taught in Example 2. After the final boost, the mice were challenged (iv) with *P. falciparum* sporozoites, and the percent survival was measured up to 15 days post-challenge. The mice administered a wild type *Spirulina* were all dead by day 6. In contrast, those administered a Pf-CSP vaccine *Spirulina* showed greater survival, with 50% living for at least 15 days post-challenge. See FIG. 9. FIG. 10 shows that 7 out of 8 mice orally dosed with a *Spirulina* containing WHcAg particles with *P. falciparum* (NANPx) epitopes developed systemic IgG against *P. falciparum*, whereas mice orally dosed with a *Spirulina* containing empty WHcAg particles (without *P. falciparum* epitopes) did not develop any IgG response.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. An oral antigenic composition comprising:

a recombinant *Spirulina*, wherein the recombinant *Spirulina* comprises an exogenous nucleic acid sequence, encoding:

a chimeric protein comprising an antigenic epitope translationally fused to a viral protein or a virus-like particle (VLP)-forming protein wherein the exogenous nucleic acid sequence is stably integrated into an endogenous locus of the *Spirulina*; and one or more pharmaceutically acceptable excipients.

2. The oral antigenic composition of claim 1, wherein the antigenic epitope is a self-antigen associated with an autoimmune disease.

3. The oral antigenic composition of claim 1, wherein the antigenic epitope is from an infectious microorganism.

4. The oral antigenic composition of claim 3, wherein the infectious microorganism is a bacterium selected from the group consisting of: *Mycobacterium, Streptococcus, Staphylococcus, Shigella, Campylobacter, Salmonella, Clostridium, Corynebacterium, Pseudomonas, Neisseria, Listeria, Vibrio, Bordetella*, and *Legionella*.

5. The oral antigenic composition of claim 3, wherein the infectious microorganism is a virus selected from the group consisting of: bacteriophage, RNA bacteriophage, Infectious Haematopoietic Necrosis Virus, Parvovirus, Herpes Simplex Virus, Hepatitis A virus, Hepatitis B virus, Hepatitis C virus, Measles virus, Mumps virus, Rubella virus, HIV, Influenza virus, Rhinovirus, Rotavirus A, Rotavirus B, Rotavirus C, Respiratory Syncytial Virus (RSV), Varicella zoster, Poliovirus, Norovirus, Zika Virus, Dengue Virus, Rabies Virus, Newcastle Disease Virus, and White Spot Syndrome Virus.

6. The oral antigenic composition of claim 3, wherein the infectious microorganism is a parasite selected from the group consisting of: *Plasmodium, Trypanosoma, Toxoplasma, Giardia, Leishmania Cryptosporidium*, helminthic parasites: *Trichuris* spp., *Enterobius* spp., *Ascaris* spp., *Ancylostoma* spp., *Necator* spp., *Strongyloides* spp., *Dracunculus* spp., *Onchocerca* spp., *Wuchereria* spp., *Taenia* spp., *Echinococcus* spp., *Diphyllobothrium* spp., *Fasciola* spp., and *Schistosoma* spp.

7. The oral antigenic composition of claim 6, wherein the infectious microorganism is the *Plasmodium*, and wherein the *Plasmodium* is *P. falciparum, P. malariae, P. ovale* or *P. vivax*.

8. The oral antigenic composition of claim 1, wherein the antigenic epitope is from a *Plasmodium* antigen selected from the group consisting of: circumsporozoite protein, thrombospondin-related anonymous protein (TRAP), Apical Membrane Antigen 1 (AMA1), major merozoite surface proteins 1-3 (MSP1-3), sexual stage antigen 25 (s25), sexual stage antigen s230, and a sequence of NANP (SEQ ID NO: 6), NVDP (SEQ ID NO:7), or NPDP (SEQ ID NO: 8).

9. The oral antigenic composition of claim 1, wherein the viral protein or VLP-forming protein comprises a capsid protein of a virus.

10. The oral antigenic composition of claim 9, wherein the capsid protein is hepatitis B core antigen (HbcAg) or woodchuck hepadnaviridae core antigen (WhcAg).

11. The oral antigenic composition of claim 1, wherein the chimeric protein comprises a scaffold protein, and wherein the antigenic epitope is linked to the scaffold protein at the N-terminus or the C-terminus, or in the body of the scaffold protein.

12. The oral antigenic composition of claim 1, wherein the recombinant *Spirulina* is non-living, dried, spray dried, freeze-dried, or lyophilized.

* * * * *